US012751704B2

(12) United States Patent
White et al.

(10) Patent No.: US 12,751,704 B2
(45) Date of Patent: Oct. 6, 2026

(54) RETRACTOR SYSTEM

(71) Applicant: Thompson Surgical Instruments, Inc., Traverse City, MI (US)

(72) Inventors: William White, Traverse City, MI (US); Zach Beery, Traverse City, MI (US); Chris Martin, Cedar, MI (US); Dan Farley, Traverse City, MI (US)

(73) Assignee: Thompson Surgical Instruments, Inc., Traverse City, MI (US)

( * ) Notice: Subject to any disclaimer, the term of this patent is extended or adjusted under 35 U.S.C. 154(b) by 210 days.

(21) Appl. No.: 18/652,984

(22) Filed: May 2, 2024

(65) Prior Publication Data

US 2024/0366206 A1 Nov. 7, 2024

Related U.S. Application Data

(60) Provisional application No. 63/463,790, filed on May 3, 2023.

(51) Int. Cl.
*A61B 17/02* (2006.01)

(52) U.S. Cl.
CPC ................................ *A61B 17/0206* (2013.01)

(58) Field of Classification Search
CPC ................ A61B 17/0206; A61B 17/02; A61B 2017/0218; A61B 2017/0212; A61B 2017/0225; A61B 2017/0237; A61B 2017/0243; A61B 17/025; A61B 2017/0256; A61B 2017/0262; A61B 17/0281; A61B 2017/0287
USPC .................................................. 600/201-245
See application file for complete search history.

(56) References Cited

U.S. PATENT DOCUMENTS 5,616,117 A * 4/1997 Dinkler .............. A61B 17/0206 600/210
5,795,291 A * 8/1998 Koros .................... A61B 17/02 600/231
5,931,777 A * 8/1999 Sava ...................... A61B 17/02 600/210
6,033,363 A 3/2000 Farley et al.
6,511,423 B2 1/2003 Farley
6,746,467 B1 6/2004 Taylor
7,582,058 B1 9/2009 Miles
7,931,591 B2 4/2011 McCarthy et al.
(Continued)

FOREIGN PATENT DOCUMENTS

KR 20120075711 7/2012

OTHER PUBLICATIONS

International Search Report and Written Opinion for Application No. PCT/US2024/027608, mailed Sep. 11, 2024, 17 pages.
(Continued)

*Primary Examiner* — Eduardo C Robert
*Assistant Examiner* — Tara Rose E Carter
(74) *Attorney, Agent, or Firm* — McAndrews, Held & Malloy, Ltd.

(57) ABSTRACT

A retractor may include one or more racks and retractor blades coupled to the respective racks via respective carriages and retractor arms. The carriages may traverse respective racks to laterally position retractor blades. The retractor blades may include tracks which the retractor arms may traverse to longitudinally position retractor blades with respect to the racks.

20 Claims, 40 Drawing Sheets

(56) References Cited

U.S. PATENT DOCUMENTS

| | | | | |
|---|---|---|---|---|
| 7,981,031 | B2 * | 7/2011 | Frasier | A61B 17/02 600/224 |
| 8,062,218 | B2 | 11/2011 | Sebastian et al. | |
| 8,636,655 | B1 | 1/2014 | Childs | |
| 8,974,381 | B1 * | 3/2015 | Lovell | A61B 90/30 600/222 |
| 9,066,701 | B1 | 6/2015 | Finley et al. | |
| 9,095,301 | B2 | 8/2015 | Hamada | |
| 9,241,619 | B2 | 1/2016 | Nowak et al. | |
| 9,314,152 | B2 | 4/2016 | Pimenta et al. | |
| 9,351,718 | B1 | 5/2016 | Arambula et al. | |
| 9,380,932 | B1 | 7/2016 | Lynn et al. | |
| 9,622,732 | B2 | 4/2017 | Martinelli et al. | |
| 9,730,683 | B2 | 8/2017 | Reimels | |
| 9,826,966 | B2 | 11/2017 | Mast et al. | |
| 10,039,539 | B2 | 8/2018 | Friedrich et al. | |
| 10,357,238 | B2 | 7/2019 | Miles et al. | |
| 10,499,896 | B2 | 12/2019 | Abidin et al. | |
| 10,603,026 | B2 | 3/2020 | Cryder et al. | |
| 10,695,044 | B2 | 6/2020 | Miles et al. | |
| 10,869,657 | B2 | 12/2020 | Raymond et al. | |
| 10,980,576 | B2 | 4/2021 | Woolley et al. | |
| 11,103,227 | B2 | 8/2021 | Baudouin et al. | |
| 11,116,489 | B2 | 9/2021 | Kim | |
| 11,129,521 | B2 | 9/2021 | Tesar et al. | |
| 11,154,288 | B1 | 10/2021 | Lovell et al. | |
| 11,219,437 | B2 | 1/2022 | Miles et al. | |
| 11,224,415 | B1 | 1/2022 | Josse | |
| 11,272,912 | B2 | 3/2022 | Heiges et al. | |
| 11,399,816 | B2 | 8/2022 | O'Connell et al. | |
| 11,432,810 | B2 | 9/2022 | Gregersen et al. | |
| 11,452,514 | B2 | 9/2022 | Truckey et al. | |
| 11,457,907 | B2 | 10/2022 | Lee et al. | |
| 11,457,910 | B1 | 10/2022 | Lynch et al. | |
| 11,478,237 | B2 | 10/2022 | Spann et al. | |
| 11,504,107 | B2 | 11/2022 | Cianfrani et al. | |
| 11,564,674 | B2 | 1/2023 | Hill et al. | |
| 11,607,209 | B2 | 3/2023 | O'Connell et al. | |
| 11,627,952 | B2 | 4/2023 | Eckhof et al. | |
| 2002/0077531 | A1 | 6/2002 | Puchovsky | |
| 2004/0176665 | A1 | 9/2004 | Branch | |
| 2005/0070765 | A1 | 3/2005 | Abdelgany | |
| 2007/0021656 | A1 | 1/2007 | Martin | |
| 2008/0058606 | A1 | 3/2008 | Miles | |
| 2008/0214898 | A1 | 9/2008 | Warren | |
| 2009/0259107 | A1 | 10/2009 | Crenshaw | |
| 2009/0275804 | A1 | 11/2009 | Bertagnoli | |
| 2010/0217089 | A1 | 8/2010 | Farley | |
| 2010/0222644 | A1 | 9/2010 | Sebastian et al. | |
| 2011/0130793 | A1 * | 6/2011 | Woolley | A61B 17/7077 606/279 |
| 2012/0136215 | A1 | 5/2012 | Farley | |
| 2016/0287236 | A1 | 10/2016 | Garcia-Bengochea et al. | |
| 2017/0172556 | A1 * | 6/2017 | Bass | A61B 17/0293 |
| 2018/0206834 | A1 | 7/2018 | Villamil et al. | |
| 2018/0303473 | A1 | 10/2018 | Spann et al. | |
| 2019/0015089 | A1 * | 1/2019 | Rosenbaum | A61B 17/0206 |
| 2019/0142480 | A1 | 5/2019 | Woolley et al. | |
| 2019/0216450 | A1 | 7/2019 | Bjork et al. | |
| 2021/0220009 | A1 | 7/2021 | Heiges et al. | |
| 2021/0401423 | A1 * | 12/2021 | Eckhof | A61B 17/7077 |
| 2022/0079573 | A1 | 3/2022 | Ortiz et al. | |
| 2022/0202404 | A1 | 6/2022 | Rajek | |
| 2022/0265256 | A1 | 8/2022 | Villamil et al. | |
| 2022/0401092 | A1 | 12/2022 | Stiefferman et al. | |
| 2024/0173022 | A1 | 5/2024 | Beery et al. | |

OTHER PUBLICATIONS

PCT, Notification of the Transmittal of the International Search Report and the Written Opinion of the International Searching Authority, or the Declaration, in International application No. PCT/US2010/058839, dated Feb. 7, 2011.

PCT, Notification Concerning Transmittal of International Preliminary Report on Patentability (Chapeter I of the Patent Cooperation Treaty), in International application No. PCT/US2010/058839, dated Jun. 14, 2012.

Office Action in U.S. Appl. No. 12/959,701, dated Sep. 18, 2012, (13 pages).

* cited by examiner

RETRACTOR SYSTEM

CROSS-REFERENCE TO RELATED APPLICATIONS

This application claims the benefit of U.S. Provisional Application No. 63/463,790, filed May 3, 2023, the disclosure of which is incorporated herein by reference in its entirety.

BACKGROUND

The present disclosure relates to a surgical apparatus and in particular to a retractor system used to retract soft tissue about a surgical incision or other operative site.

Further limitations and disadvantages of conventional and traditional approaches will become apparent to one of skill in the art, through comparison of such approaches with the present disclosure as set forth in the remainder of the present application with reference to the drawings.

SUMMARY

Various aspects of this disclosure provide a retractor system that may retract soft tissue and/or anatomical structures. For example and without limitation, various aspects of the disclosure are directed to a retractor system comprising a rack assembly comprises multiple racks to which are attached retractor blades via respective retractor arms and carriages. The carriages may traverse along respective racks to position retractor arms and retractor blades coupled to such retractor arms.

One or more of the retractor blades may comprise a retractor blade track that runs longitudinally between an retractor blade proximal end and a retractor blade distal end. A retractor arm may be coupled to the retractor blade track, which may permit the retractor arm to traverse or translate longitudinally along the retractor blade. In various embodiments, the retractor blade track may permit the retractor arm to be selectively positioned longitudinally along the retractor blade and locked into such selected position.

Further aspects will become apparent to one of skill in the art through review of the present disclosure and referenced drawings.

BRIEF DESCRIPTION OF THE DRAWINGS

The figures provide various views of a retractor system in accordance with various aspects of the present disclosure.

DETAILED DESCRIPTION

Figure 1A:
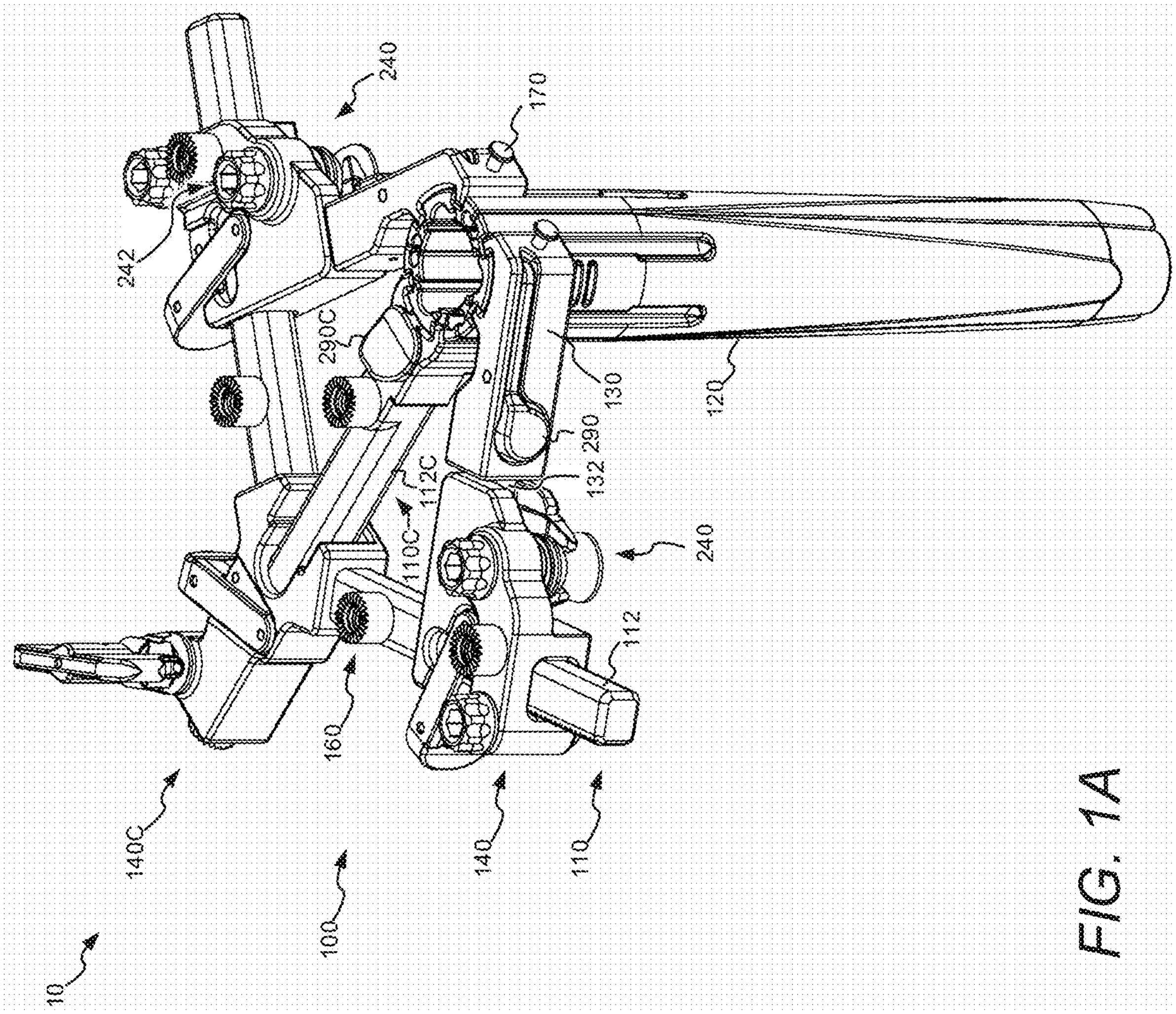
FIGS. 1A-1M provide various views of a retractor system in accordance with aspects of the present disclosure.

The following discussion presents various aspects of the present disclosure by providing examples thereof. Such examples are non-limiting, and thus the scope of various aspects of the present disclosure should not necessarily be limited by any particular characteristics of the provided examples. In the following discussion, the phrases "for example," "e.g.," and "exemplary" are non-limiting and are generally synonymous with "by way of example and not limitation," "for example and not limitation," and the like.

As utilized herein, "and/or" means any one or more of the items in the list joined by "and/or". As an example, "x and/or y" means any element of the three-element set {(x), (y), (x, y)}. In other words, "x and/or y" means "one or both of x and y." As another example, "x, y, and/or z" means any element of the seven-element set {(x), (y), (z), (x, y), (x, z), (y, z), (x, y, z)}. In other words, "x, y and/or z" means "one or more of x, y, and z."

The terminology used herein is for the purpose of describing particular examples only and is not intended to be limiting of the disclosure. As used herein, the singular forms are intended to include the plural forms as well, unless the context clearly indicates otherwise. It will be further understood that the terms "comprises," "includes," "comprising," "including," "has," "have," "having," and the like when used in this specification, specify the presence of stated features, integers, steps, operations, elements, and/or components, but do not preclude the presence or addition of one or more other features, integers, steps, operations, elements, components, and/or groups thereof.

It will be understood that, although the terms first, second, etc. may be used herein to describe various elements, these elements should not be limited by these terms. These terms are only used to distinguish one element from another element. Thus, for example, a first element, a first component or a first section discussed below could be termed a second element, a second component or a second section without departing from the teachings of the present disclosure. Similarly, various spatial terms, such as "upper," "lower," "side," and the like, may be used in distinguishing one element from another element in a relative manner. It should be understood, however, that components may be oriented in different manners, for example a semiconductor device may be turned sideways so that its "top" surface is facing horizontally and its "side" surface is facing vertically, without departing from the teachings of the present disclosure.

In the drawings, various dimensions (e.g., layer thickness, width, etc.) may be exaggerated for illustrative clarity.

Additionally, like reference numbers are utilized to refer to like elements throughout the discussions of various examples.

The discussion will now refer to various example illustrations provided to enhance the understanding of the various aspects of the present disclosure. It should be understood that the scope of this disclosure is not limited by the specific characteristics of the examples provided and discussed herein.

FIGS. 1A-1M provide various views of a retractor system 10. In particular, FIGS. 1A-1D, 1H, and 1J show a retractor system 10 in an initial position in which retractor blades 120 come together to form a closed circular cylinder. Conversely, FIGS. 1E-1G and 1K-1M show the retractor system 10 in a retracted position, in which the retractor blades 120 are positioned away from each other. In such a retracted position, back sides of the retractor blades 120 may hold back or retract soft tissue and/or other anatomical structures.

As depicted, the retractor system 10 may include a rack assembly 100 to which are attached retractor blades 120 via respective retractor arms 130, 130C and carriages 140, 140C. In various embodiments, the rack assembly 100, the retractor blades 120, the retractor arms 130, 130C and the carriages 140, 140C may be formed from surgical stainless steel. In some embodiments, various alternative materials may be used to form all or part of retractor system 10.

Figure 9:
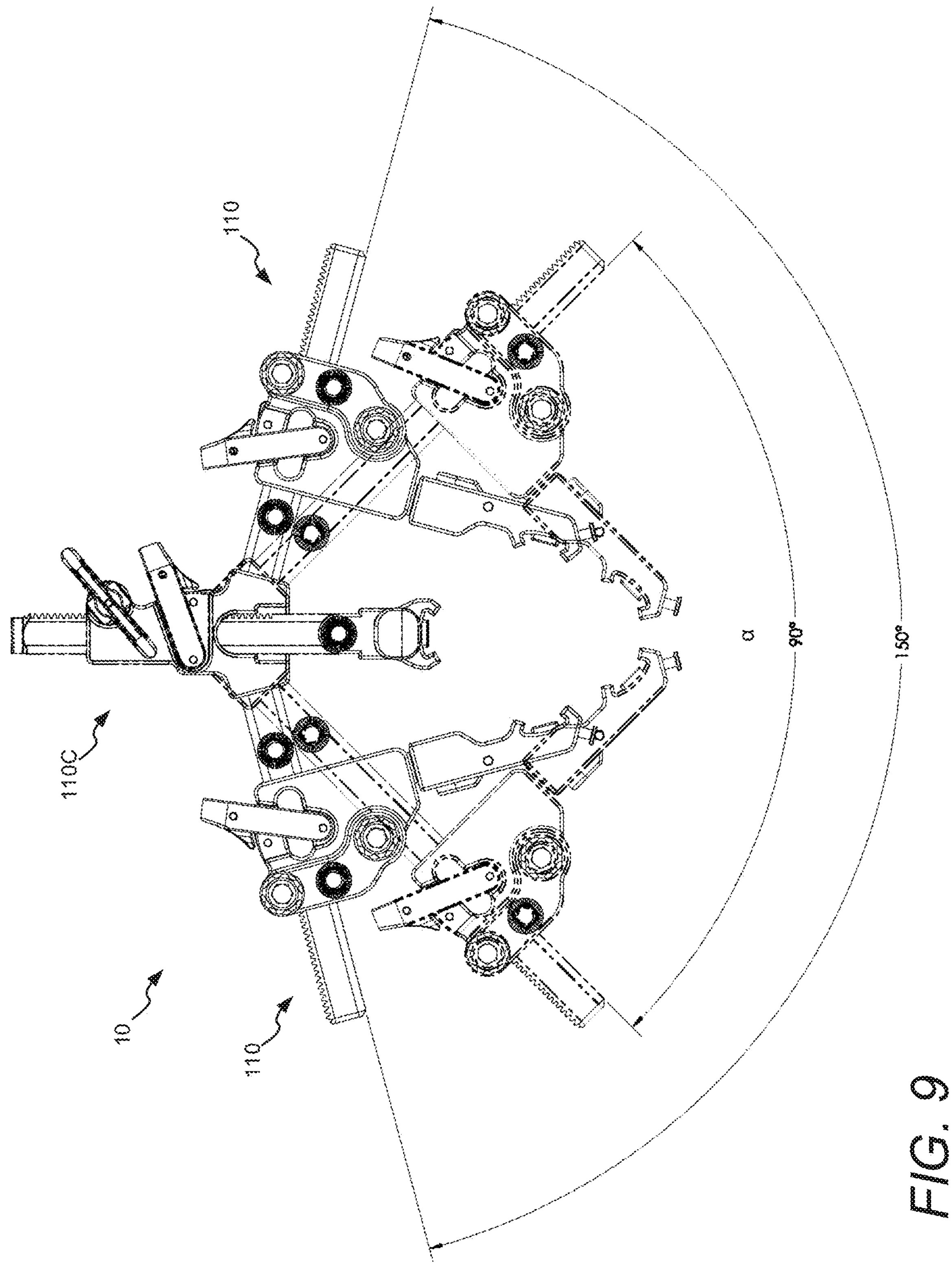
FIG. 9 depicts the outer racks of the retractor system of FIGS. 1A-1M and various angles formed by the outer racks in various embodiments.

As shown, the rack assembly 100 may include three racks 110, 110C, though various embodiments may include a greater number or a lesser number of racks. A proximal end of the each outer rack 110 may be coupled to the central carriage 140C. In one embodiment, proximal ends of outer racks 110 are affixed to lateral sides of the central carriage 140C. The outer racks 110 may extend from the central carriage 140C and form an internal angle $\alpha$ between 90° and 180° with respect to each other. Further, the central rack 110C may pass through the central carriage 140C and divide the internal angle $\alpha$ formed by the outer racks 110. See, e.g., FIG. 9. In various embodiments, the central rack 110C bisects the internal angle $\alpha$. Moreover, unlike the outer racks 110 which are coupled to the central carriage 140C in a fixed manner, the central carriage 140C may traverse the central rack 110C as explained further below.

A proximal portion of each outer retractor arm 130 may be coupled to a respective outer rack 110 via an angling assembly 240 of a respective carriage 140. Conversely, a proximal portion of the central retractor arm 130C may be affixed to a distal end of the central rack 110C. Further, a distal portion of each retractor arm 130, 130C may be coupled to a respective retractor blade 120 via a vertical retractor arm channel 270 through a distal end of each retractor arm 130, 130C. The vertical retractor arm channel 270 may permit the retractor arms 130, 130C to longitudinally traverse at least a portion of its respective retractor blade 120.

In various embodiments, the outer racks 110, outer retractor arms 130, and outer carriages 140 may essentially mirror each other. Thus, in the interest of brevity, separate detailed descriptions of the outer racks 110, outer retractor arms 130, and outer carriages 140 are not provide since their implementation and operation are readily discerned from the provided descriptions for the other outer rack 110, outer retractor arm 130, and outer carriage 140.

As shown, each rack 110, 110C may comprise a cylindrical rod or rail 112, 112C having a rectangular cross section. Moreover, each rail 112, 112C may include rack teeth 114, 114C spanning a longitudinal surface of the rail 112, 112C. While not depicted, one or more of the rails 112, 112C may include a stop toward a free end of the respective rail 112, 112C to prevent accidental removal of the rack 110, 110C from its respective carriage 140, 140C.

Each carriage 140, 140C may include a pinion 136, 136C. The pinion 136, 136C may include a head 137, 137C and teeth that engage the rack teeth 114, 114C of the rack 110, 110C. The head 137, 137C may include a socket 139 to receive a tool 200, which may rotate the pinion 136, 136C. Through rotation of the pinion 136, 136C and its engagement with rack teeth 114, 114C, the pinion 136, 136C may impart ratcheted-movement of the carriage 140, 140C with respect to its rack 110, 110C. In particular, rotation of the pinion 136 in a first direction may cause an outer carriage 140 to traverse along its rack 110 in a first direction and draw an attached retractor blade 120 in the first direction along its rack 110. Conversely, rotation of the pinion 136 in a second direction may cause an outer carriage 140 to traverse along its rack 110 in a second direction and draw an attached retractor blade 120 in the second direction along its rack 110. Similarly, rotation of the pinion 136C in a first direction may cause a distal end of the central rack 110C to be retracted toward the central carriage 140C and thus draw an attached retractor blade 120 toward the central carriage 140C. Conversely, rotation of the pinion 136C in a second direction may cause a distal end of the central rack 110C to be driven away from the central carriage 140C and thus extend an attached retractor blade 120 away from the central carriage 140C.

As shown, each carriage 140, 140C may include a lever 150, 150C that may be selectively moved between a ratcheted position and a disengaged position. When placed in the ratcheted position, the lever 150, 150C may position a pawl such that a distal end of the pawl is moved toward and engages rack teeth 114, 114C of its rack 110, 110C. Conversely, when placed in the disengaged position, the lever 150, 150C may position the distal end of the pawl away from the rack teeth 114, 114C and disengage the distal end of the pawl from rack teeth 114, 114C of its rack 110, 110C. Due to such disengagement of the pawls, the disengaged position may permit the carriage 140, 140C to freely slide along its rack 110, 110C.

In various embodiments, the pawl and rack teeth 114, 114C may permit ratcheted movement in a first direction when the distal end of the pawl is engaged with the rack teeth 114, 114C. Moreover, while engaged, the distal end of the pawl and rack teeth 114, 114C may prevent movement in the opposite second direction. To this end, the rack teeth 114, 114C of the rack 110, 110C in various embodiments may be uniformly-shaped and symmetrically-sloped, with leading and trailing edges having the same slope. However, the distal end of the pawl may not be symmetrically sloped. Instead, the leading edge (i.e., edge toward the compression direction of ratcheted movement) may be more moderately-sloped than the opposite trailing edge. As a result of the more moderately-sloped or less steeply-sloped leading edge, lateral movement of the carriages 140, 140C with respect to its rack 110, 110C in the retracting direction imparts an upward force upon the distal end of the pawl that is sufficient to overcome the biasing force of an associated spring and permit the distal end of the pawl to travel over the rack teeth 114, 114C. Conversely, as a result of the more steeply-sloped trailing edge, lateral movement of the carriages 140, 140C with respect to its rack 110, 110C in the opposite second direction fails to impart an upward force upon the distal end of the pawl that is sufficient to overcome the biasing force of the spring, thus preventing the distal end of the pawl from traveling over the rack teeth 114, 114C. In this manner, the carriage 140, 140C may lock or retain its position along its rack 110, 110C, thereby maintaining a desired position of the retractor blade 120 associated with the carriage 140, 140C.

As shown, a proximal portion of the central retractor arm 130C may be affixed to a distal end of the central rack 110C. Conversely, a proximal portion of the outer retractor arms 130 may be coupled to the outer carriages 140 via a joint the permits rotation of the outer retractor arms 130. In particular, a retractor arm shaft 132 of the retractor arms 130 may be coupled to an angling assembly 240 of the carriage 140. The retractor arm shaft 132 and outer carriages 140, unlike the central rack 110C and central retractor arm 130C, may cooperate to provide an axis of rotation that runs longitudinally through the outer retractor arms 130. Thus, the axis of rotation provided by the outer carriage 140 and retractor arm shaft 132 may be perpendicular to, intersect, or otherwise cross a longitudinal axis of the respective outer rack 110. For example, FIG. 1G depicts the outer retractor arms 130 angled such that lower ends of their respective retractor blades 120 are angled away from each other.

As shown, the outer carriage 140 may comprise a carriage body 142 having an opening to receive an outer rack 110. The opening may pass through lateral sides of a proximal portion of the carriage body 142. As such, the rack 110 may pass through the outer carriage 140, thus permitting the outer carriage 140 to traverse the rack 110 and position its outer retractor arm 130 and retractor blade 120.

The angling assembly 240 of each outer carriage 140 may rotate a respective outer retractor arm 130 about a longitudinal axis of the outer retractor arm 130 and lock the outer retractor arm 130 at a desired angle. To this end, the angling assembly 240 may include an adjustment screw 242 that passes vertically through a distal portion of the outer carriage 140. In the depicted embodiment, the adjustment screw 242 may include a threaded portion 244 and a head 247. The head 247 may include an opening or keyed recess sized to closely mate with a tool. Such a tool may be used to rotate the adjustment screw 242 via its head 247. Other mechanisms may be used to rotate the adjustment screw 242. For example, the adjustment screw 242 may include a thumbwheel, tab, or winding mechanism for rotating by hand. As another example, the adjustment screw 242 may include a slotted or otherwise formed head 247.

A bobbin 246 may be coupled to or integrated with a lower end of the adjustment screw 242. Moreover, threads of the threaded portion 244 may engage threads or other features of the carriage body 142. Due to such threaded engagement, rotation of the adjustment screw 242 in a first direction may extend the bobbin 246 in a downward direction. Conversely, rotation of the adjustment screw 242 in an opposite second direction may retract the bobbin 246 in upward direction.

The angling assembly 240 may include members or tines 248. Proximal ends of the tines 248 may be affixed to the retractor arm shaft 132 of each outer retractor arm 130. Distal ends of the tines 248 may protrude from the retractor arm shaft 132 and engage tapered surfaces of the bobbin 246. Due to the tines 248 engaging the tapered surfaces of the bobbin 246, the tines 248 may rotate the retractor arm shaft 132 of the respective outer retractor arm 130 in a first direction as the bobbin 246 is moved downward. Conversely, the tines 248 may rotate the retractor arm shaft 132 of the respective outer retractor arm 130 in a second direction that is opposite to the first direction as the bobbin 246 is moved upward. Thus, a person may rotate the adjustment screw 242 via a tool engaged with the head 247 to adjust a rotation of the respective outer retractor arm 130.

Through rotation of an adjustment screw 242, each outer retractor arm 130 may be rotated with respect to its respective outer carriages 140 and such rotation may translate to the retractor blades 120 coupled to the respective outer retractor arm 130. In this manner, distal ends of the retractor blades 120 may be individually angled toward each other or away from each other. Further, the bobbin 246, tines 248, and/or other aspects of the angling assembly 240 may be configured to provide a mechanical stop at either or both ends of a range of angles. Moreover, the thread pitch of the threaded portion 244 may be selected to provide a desired fineness to the adjustability of the angle.

As shown in FIGS. 3A-3H, each retractor blade 120 may comprise a retractor blade track 305 that runs longitudinally down a back side of the retractor blade 120. In various embodiments, the retractor blade track 305 may longitudinally span only a portion of the back side of the retractor blade 120. While the depicted embodiments show the retractor blade track 305 running partially down the back side of the retractor blade 120 from a proximal or upper end of the retractor blade 120, the retractor blade track 305 in other embodiments may run further along the retractor blade 120, may run fully along the retractor blade 120, may be positioned in a central portion of the retractor blade 120, and/or may be positioned in a distal portion of the retractor blade 120.

A shown, the retractor blade track 305 may comprise track catches 310 that are flanked by longitudinal retractor blade rails 320. In various embodiments, the retractor blade rails 320 are formed by longitudinal track recesses 321 in the back side of the retractor blade 120. In particular, each recess 321 may extend into the back side of the retractor blade 120 at an angle such that a distance between the opposing track recesses 321 is greater at the back side of the retractor blade 120 than at their depths into the back side of the retractor blade 120. Moreover, each recess 321 may comprise a recess upper end 322 and a recess lower end 324. The recess upper ends 322 may provide openings at the upper or proximal end of the retractor blade 120 for the retractor arms 130, 130C to enter and grasp the retractor blade rails 320. In particular, such openings may be sized and spaced to receive respective flanges or fingers 276 of the retractor arm channel 270 that runs through the distal portion of the retractor arm 130, 130C. In various embodiments, the opening of the upper ends 322 may be tapered such that the opening provided at the upper end 322 is larger than the opening or groove provided by the recess 321. Such tapering may make it easier for a person to slide the fingers 276 into the track recesses 321 and engage the retractor blade rails 320 with the fingers 276 of the retractor arms 130, 130C.

Similarly, the lower ends 324 of the track recesses 321 may provide openings for the retractor arms 130, 130C to enter and grasp the retractor blade rails 320. In particular, such openings may be sized and spaced to receive respective flanges or fingers 276 of the retractor arms 130, 130C. However, the recess lower ends 324 unlike of the recess upper ends 322 may not extend all the way to an end of the retractor blade 120. As such, the flanges or fingers 276 may not be simply inserted into openings at the distal end of the retractor blade 120. Thus, in order to permit insertion of the fingers 276 via the recess lower end 324, the retractor blade 120 may include larger recesses 325 at the recess lower ends 324, which taper toward the recess lower ends 324. These larger recesses 325 are sized to receive the fingers 276 and direct the fingers 276 into the recess lower ends 324 as the retractor blade 120 slides downward with respect to the retractor arms 130, 130C.

The fingers 276 of the retractor arms 130, 130C may be angled inward toward the retractor arm channel 270 so as to closely mate with and engage the retractor blade rails 320 via the track recesses 321 when the retractor arm channel 270 receives the retractor blade track 305. In this manner, the fingers 276 may capture the retractor blade rails 320 and position the retractor blade track 305 in its retractor arm channel 270.

As described above, the retractor arms 130, 130C may engage retractor blade rails 320 in a manner that permits the retractor arms 130, 130C to translate longitudinally along the respective retractor blade 120 while firmly coupling the retractor blade 120 to its respective rack 110, 110C. However, in other embodiments, the retractor arms 130, 130C may be implemented to utilize different techniques and/or mechanisms to couple the retractor blades 120 to the racks 110, 110C.

For example, the retractor arms 130, 130C may engage the retractor blades 120 via a male/female T-slot connection in which the retractor arms 130, 130C comprise a male T-shaped member that engages a female T-shaped slot of the retractor blades 120. Conversely, the retractor blades 120 may comprise a male T-shaped member that engages a female T-shape slot of the retractor arms 130, 130C.

Alternatively, the retractor arms 130, 130C may engage the retractor blades 120 via a cam lock mechanism that grips the retractor blade rails 320. For example, the cam lock mechanism may comprise a cam that pulls fingers of the retractor arms 130, 130C toward each other to grasp the retractor blade rails 320 in a manner similar to the above described fingers. Similarly, the retractor arms 130, 130C may operate as a crab clamp in which rotation of screw in a first direction may cause fingers of the retractor arms 130, 130C to grasp the retractor blade rails 320 of the retractor blade 120 and rotation of the screw in a second direction may cause the fingers of the retractor arms 130 to release the retractor blade rails 320 of the retractor blade 120.

In yet another embodiment, the retractor blade track 305 along the back side of a retractor blade 120 may include teeth spaced along its longitudinal length instead of track catches 310. Actuation of a lever, button, or other mechanism of the retractor arms 130, 130C may control extension/retraction of a distal end of a pawl into/from the retractor arm channel 270 through the distal end of the retractor arm 130, 130C. Extension of the pawl may cause the distal end of the pawl to engage one or more teeth of the retractor blade 120 and restrict further translation of the retractor arm 130, 130C along the retractor blade 120 until the lever, button, or other mechanism is actuated to retract the pawl and disengage a distal end of the pawl from the teeth.

As shown, the outer retractor arms 130 may include a blade release button 290. The blade release button 290 may be configured to pivot a pawl 297 about a pivot pin 292. A spring (not shown) may supply a biasing force that pivots the pawl 297 297 and biases a distal end of the pawl 297 toward a fully engaged position. In the fully engaged position, the distal end of the pawl 297 may extend from a distal end of the outer retractor arm 130 and into the retractor arm channel 270. In such an engaged position, the distal end of the pawl 297 may engage a track catch 310 of the retractor blade 120 and retain the retractor blade 120 at a specific position along the retractor blade track 305. See, e.g., FIG. 3.3. A person, however, may press the blade release button 290 to pivot the pawl 297 about the pivot pin 292 and the distal end of the pawl 297 toward the fully disengaged position. In the fully disengaged position, the distal end of the pawl 297 may move away from and disengage the track catch 310 of the retractor blade 120 so as to permit sliding the retractor blade 120 along the retractor arm channel 270. See, e.g., FIG. 3G.

As shown in FIGS. 3A-3D, the retractor blade 120 may be attached to an outer retractor arm 130 by pressing the blade release button 290 and sliding the retractor blade 120 into recess upper ends 322 at the top or proximal end of the retractor blade 120. A person may also press the blade release button 290 in order to slide the outer retractor arm 130 along the retractor blade track 305 in a back side of the retractor blade 120. Such sliding may extend the retractor blade 120 further into a surgical site or retract the retractor blade 120 from the surgical site. Further, the retractor blade 120 may be fully disengaged from the outer retractor arm 130 by reversing the process. Namely, a person may press the blade release button 290 and slide the retractor blade 120 with respect to the outer retractor arm 130 such that the retractor blade 120 slides off the outer retractor arm 130 via the recess upper ends 322 at the proximal end of the retractor blade 120.

Similarly, as shown in FIGS. 3E-3H, the retractor blade 120 may be attached to the outer retractor arm 130 by pressing the retractor blade 120 into the larger recesses 325 at the recess lower ends 324 of the retractor blade track 305. In various embodiments, the retractor blade track 305 may be configured to engage the distal end of the pawl 297 as the outer retractor arm 130 is pressed into the recess lower ends 325 via the larger recesses 325 of the retractor blade track 305. Thus, unlike attachment via the proximal end of the retractor blade track 305, a person need not (but can) press the blade release button 290 in order to attach the retractor blade 120 to the outer retractor arm 130. Further, the retractor blade 120 may be fully disengaged from the outer retractor arm 130 by reversing the process. Namely, a person may press the blade release button 290 and slide the retractor blade 120 with respect to the outer retractor arm 130 such that retractor blade 120 slides off the outer retractor arm 130 via the recess lower ends 324 of the retractor blade track 305.

Similar to the blade release button 290 of the outer retractor arms 130, the central retractor arm 130C may include a slider 290C. The slider 290C may be configured to slide longitudinally along the central retractor arm 130C. A spring 292C may supply a biasing force that biases a pawl 297C toward the retractor arm channel 270 and a fully engaged position. See, e.g., FIGS. 3P-3T. In the fully engaged position, a distal end of the pawl 297C may extend into the retractor arm channel 270 that passes through the distal end of the central retractor arm 130C. In such an engaged position, the distal end of the pawl 297C may engage a track catch 310 of the retractor blade 120 and retain the retractor blade 120 at a specific position along the retractor blade track 305. See, e.g., FIGS. 3P-3Q. A person, however, may slide the slider 290C away from the retractor blade 120 to move the slider 290C and the distal end of the pawl 297C toward the fully disengaged position. In the fully disengaged position, the distal end of the pawl 297C may disengage the track catch 310 of the retractor blade 120 so as to permit sliding the retractor blade 120 along the retractor arm channel 270. See, e.g., FIGS. 3S-3T.

As shown in FIGS. 1A-1M, the retractor system 10 may include one or more connectors 160. In particular, each outer carriage 140 may include a connector 160 on a top surface of the carriage body 142. Further, each rack 110, 110C may include a connector 160 on a top surface of the rack 110. The connectors 160 on the racks 110, 110C may prevent carriages 140, 140C from traversing past the connectors 160. As such, the connectors 160 on the outer racks 110 may be positioned toward the central carriage 140C in order to permit the outer carriages 140 to traverse a majority of the length of the rack 110. Similarly, the connector 160 on the top side of the central rack 110C may be positioned toward the distal end of the central rack 110C in order to permit the central carriage 140C to traverse a majority of the length of the central rack 110C. The central rack 110C may further include a connector 160 on a proximal end surface of the central rack 110C. While the retractor system 10 is depicted with six connectors 160 at certain locations, other embodiments may include a different number of connectors 160. Moreover, the connectors 160 may be positioned at similar locations and/or at different locations than those depicted.

In various embodiments, each connector 160 comprises a threaded bore 162 and a serrated upper surface 164. The threaded bore 162 may receive a threaded end of a knob, handle, retractor frame arm, etc. For example, FIGS. 1H-1I depict a distal end of an articulated arm 400 coupled to the connector 160 on the top surface of the central rack 110C. The articulated arm 400 may be part of a frame assembly. The frame assembly may be a freestanding floor assembly or may be mounted to an operating table via a rail or other structure of the operating table. As shown, the distal end of the articulated arm may comprise a knob 410. The knob 410 may include a head 411 coupled to a threaded shaft 412 that passes through the distal end of the articulated arm 400. The threaded shaft 412 may be sized to be inserted into the threaded bore 162 of a connector 160. Moreover, the distal end of the articulated arm 400 may include a serrated surface 402 that circumscribes the threaded shaft 412.

As such, the threaded shaft 412 may be inserted into the threaded bore 162 of a connector 160. In some embodiments, a person may turn the knob 410 by hand in order to screw the knob 410 into the connector 160 and tightly engage the serrated surface 402 of the articulated arm 400 with the serrated surface 164 of the connector 160. Such engagement between serrated surfaces 164, 402 may lock the articulated arm 400 to the connector 160 in a manner that prevents rotation of the articulated arm 400 with regard to the connector 160. While the knob 410 is shown with a head 411 suitable for turning by hand, the head of the knob 410 in some embodiments may designed for turning with a tool. For example, the head of the knob 410 may include a keyed recess or may be replaced with a head having a keyed recess sized to receive a tool. A person via the aid of such a tool may then turn the head 411 to screw the threaded shaft 412 into the threaded bore 162 and attach the articulated arm 400 to the connector 160.

Figure 1B:
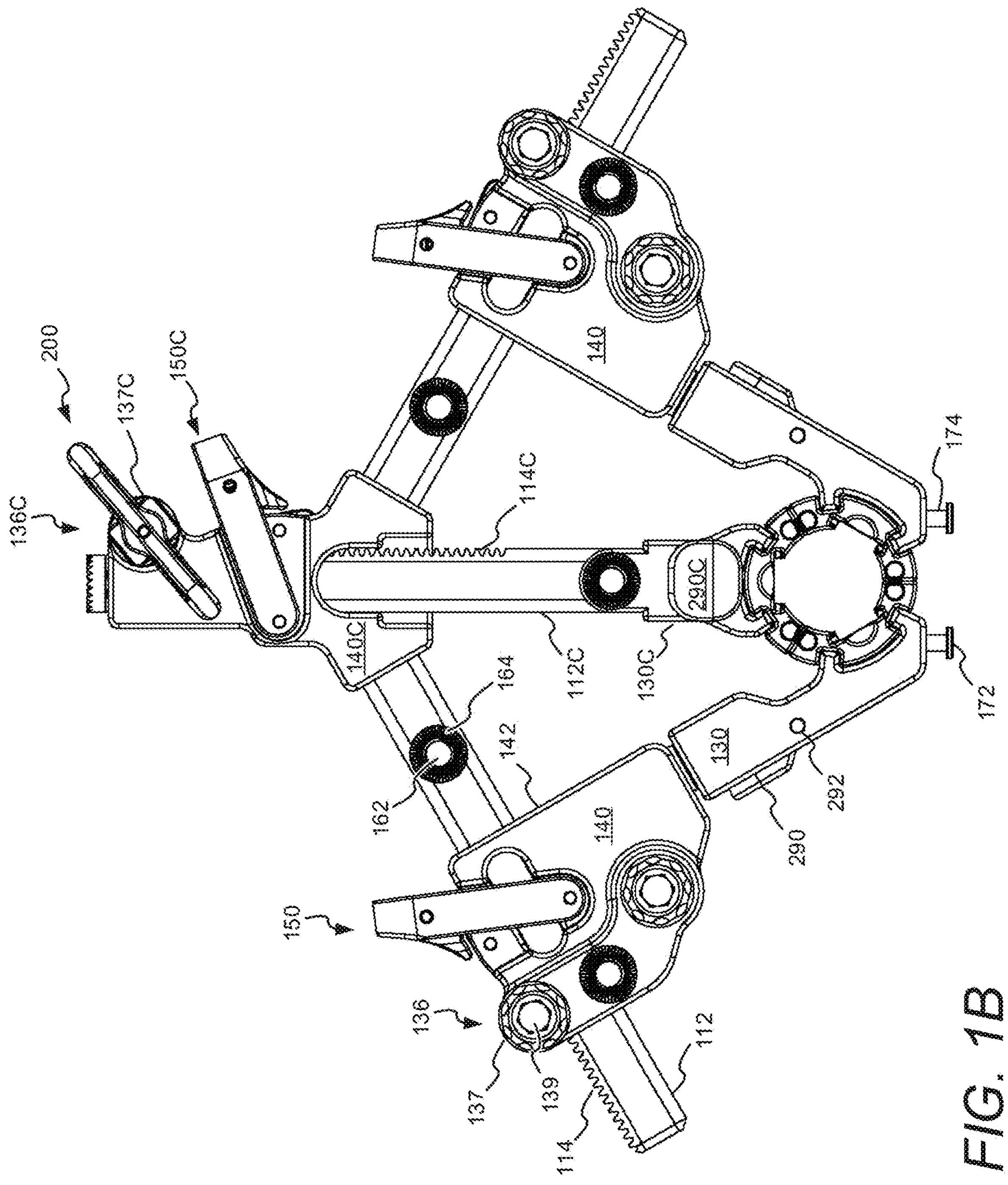
Figure 1D:
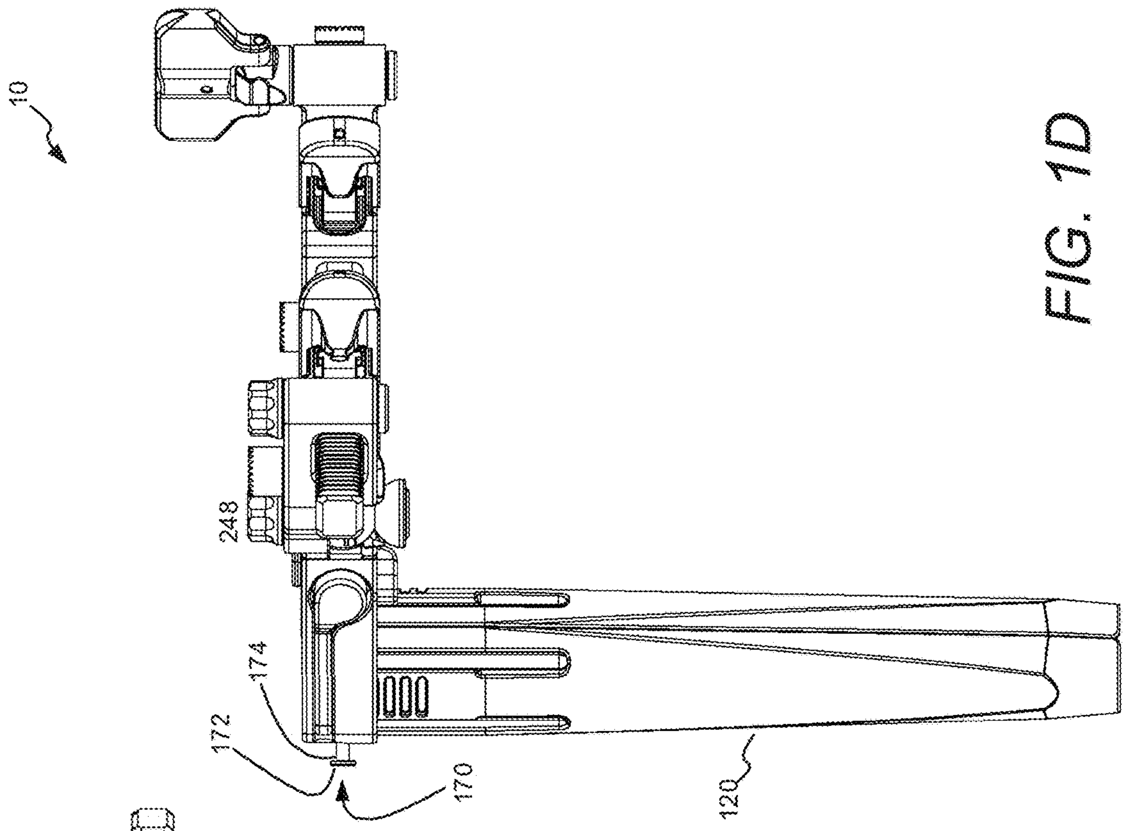
Figure 1C:
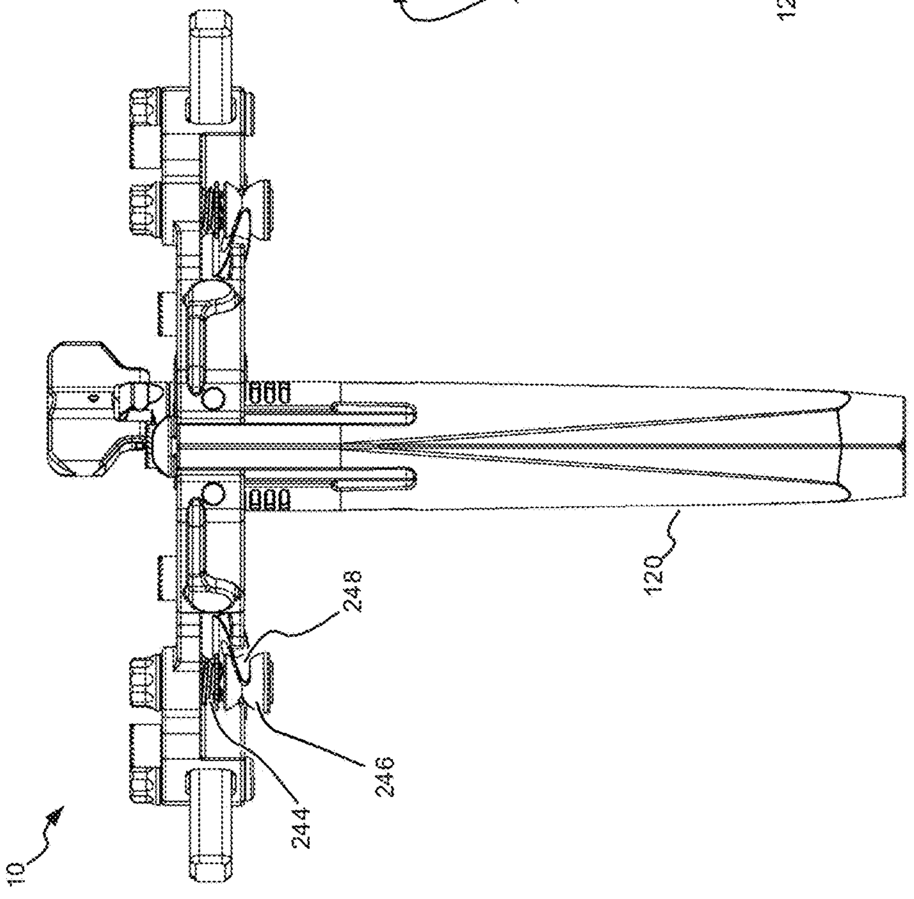
Figure 1E:
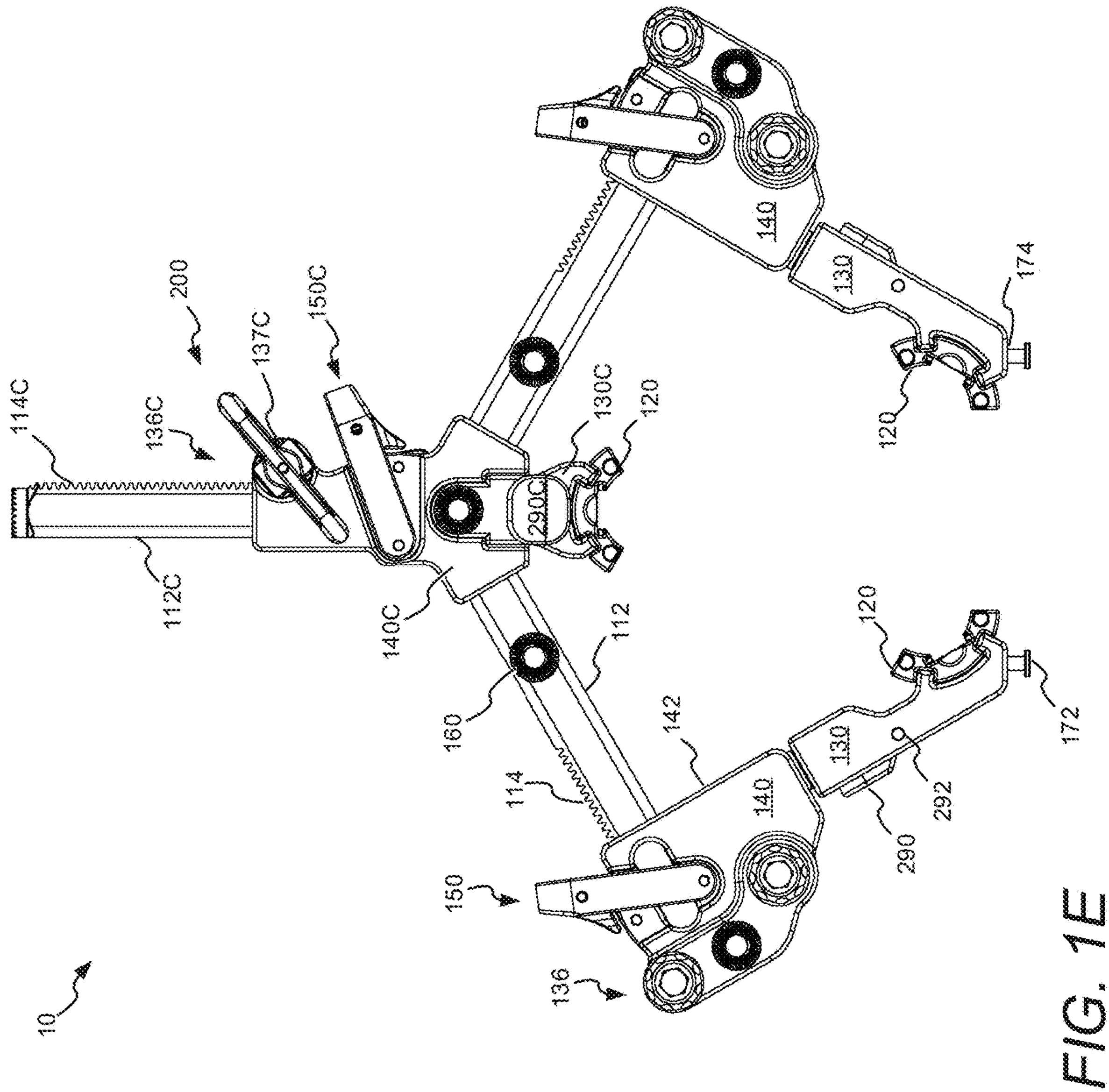
Figure 1F:
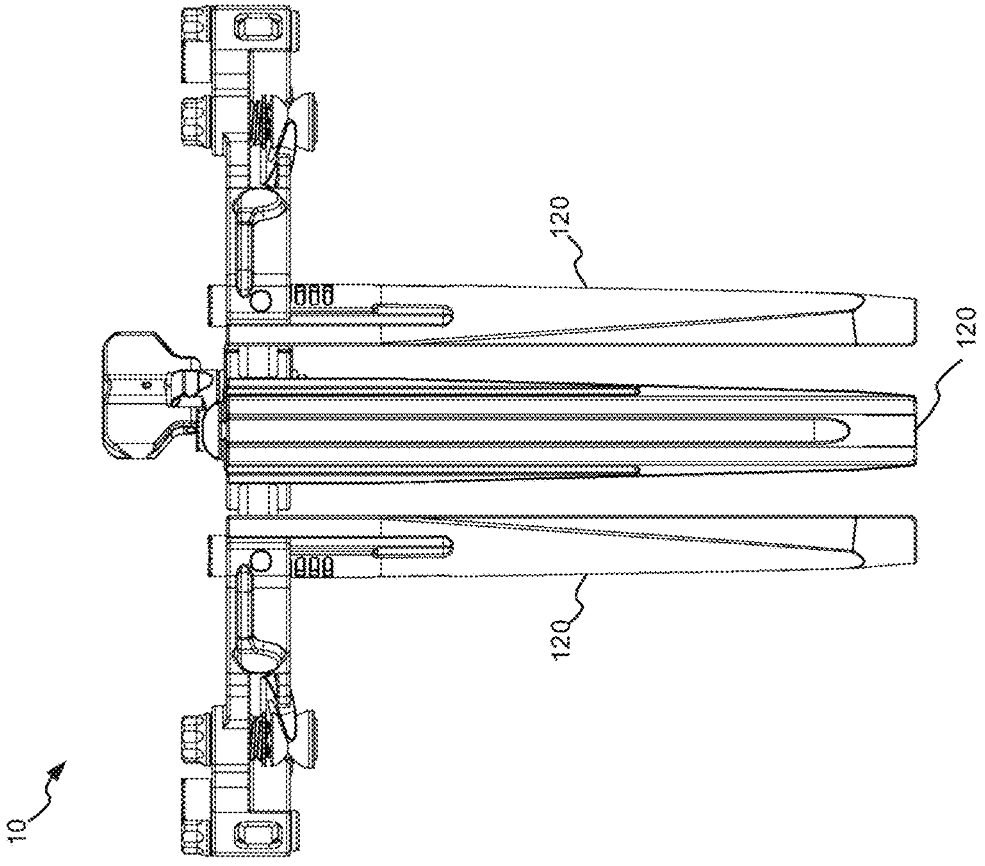
Figure 1G:
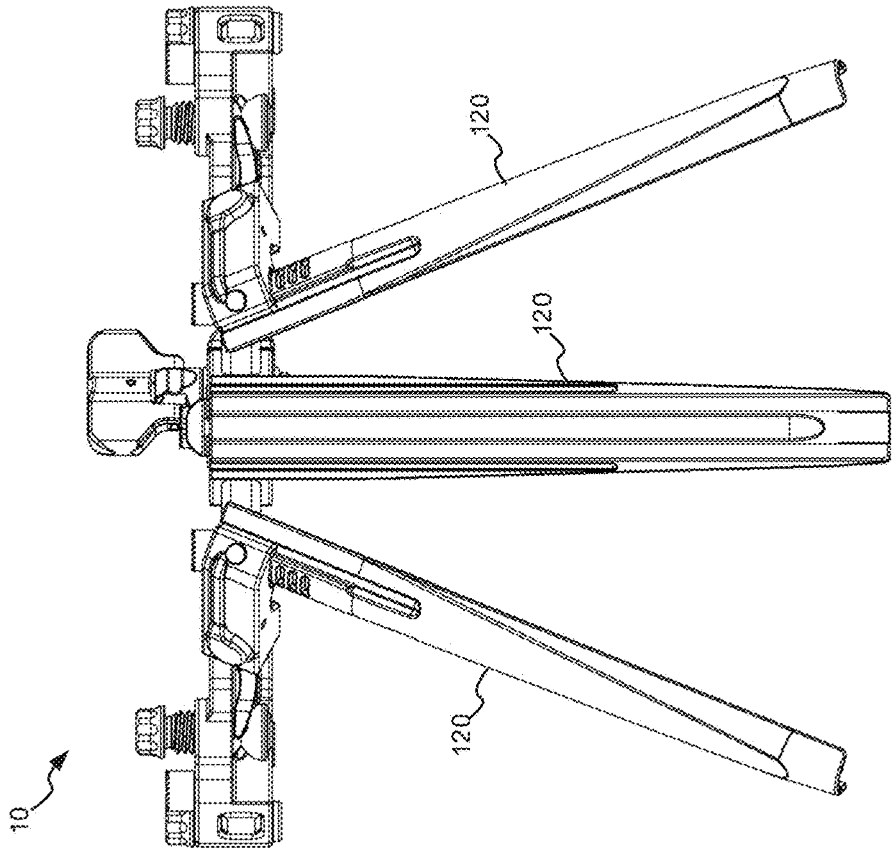
Figure 1I:
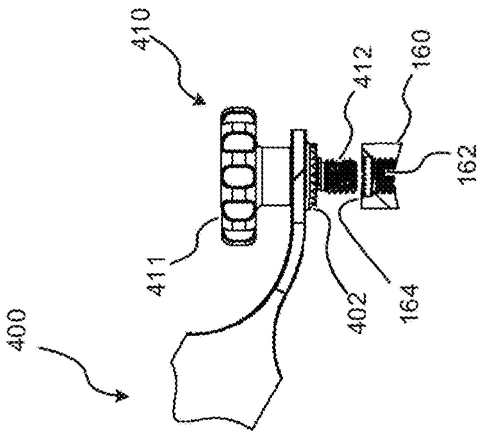
Figure 1H:
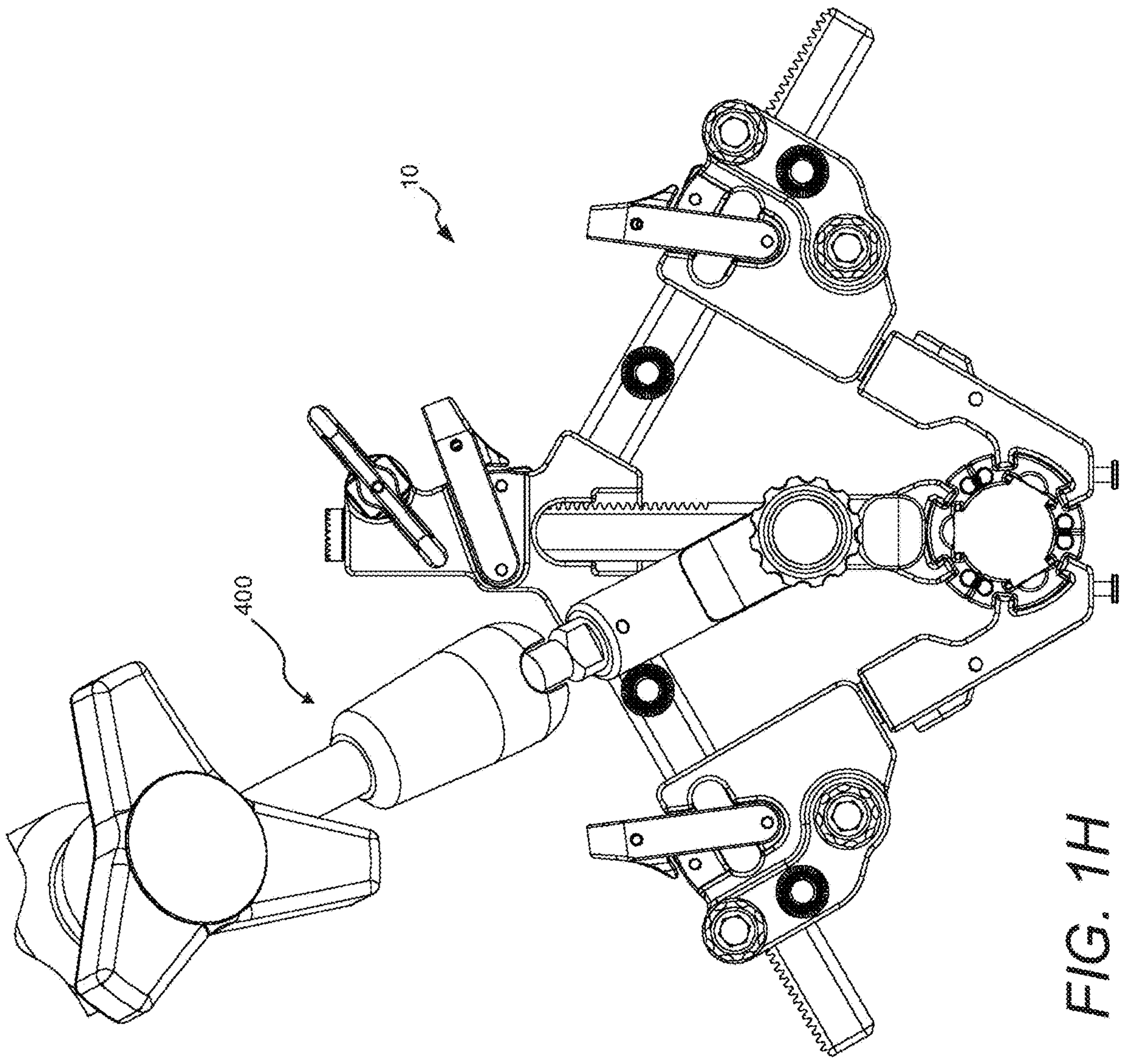
Figure 1K:
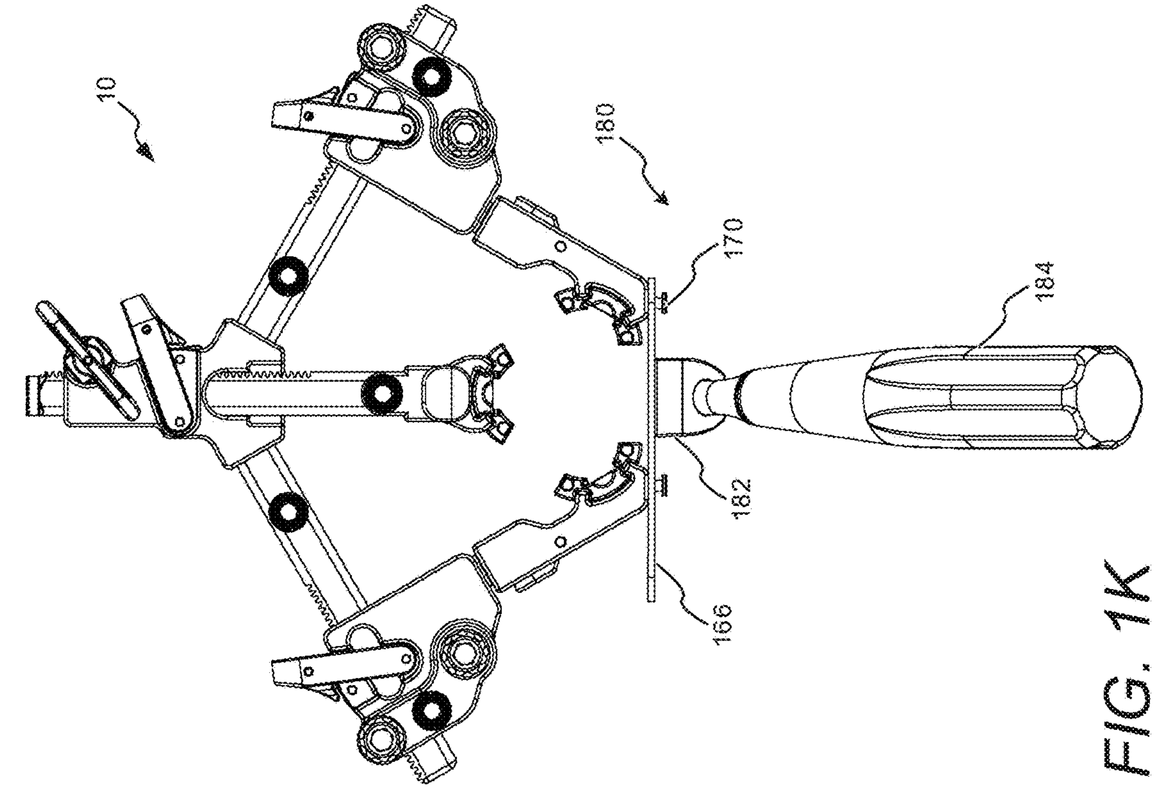
Figure 1J:
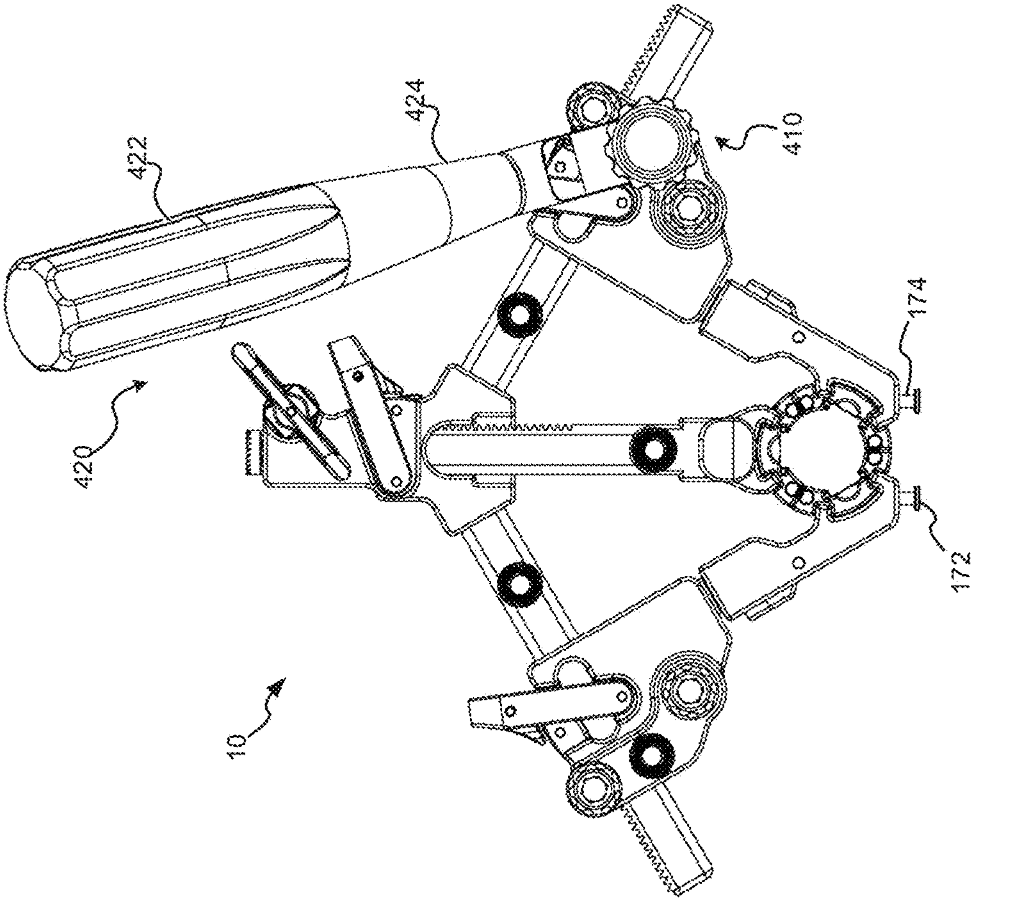

FIG. 1J depicts a distal end of a handle 420 coupled to the connector 160 on the top surface of one or the outer carriages 140. The handle 420 may aid a person in properly positioning the retractor system 10 with respect to a surgical site. The handle 420 may comprise a handle grip 422, a shaft 424, and a knob 410. The handle grip 422 may be coupled to a proximal end of the shaft 424. The threaded shaft 412 of the knob 410 may pass through a distal end of the shaft 424. Moreover, the distal end of the shaft 424 may include a serrated surface that circumscribes the threaded shaft 412.

Thus, the handle 420 may be attached to any one of the connectors 160 in a similar manner as the articulated arm 400. Namely, a person may turn the knob 410 by hand in order to screw the knob 410 into the connector 160 and tightly engage the serrated surface of the handle 420 with the serrated surface 164 of the connector 160. Such engagement between serrated surfaces may lock the handle 420 to the connector 160 in a manner that prevents rotation of the connector 160 with regard to the handle 420.

Referring now to FIGS. 4A-4K, a retractor blade 120 may include retractor blade channel 121 configured to receive an intradiscal shim 450. The intradiscal shim 450 may be inserted into the retractor blade channel 121 such that a shim distal end extends below the distal end of the retractor blade 120. To this end, the retractor blade channel 121 may include channel recesses 123 (see, e.g., FIG. 4H) that extend longitudinal along a front side of the retractor blade 120 from a proximal end of the retractor blade 120 toward a distal end of the retractor blade 120. In some embodiments, the channel recesses 123 are closed toward the distal end of the retractor blade 120 to provide a stop against which the intradiscal shim 450 may be seated. As further shown, the retractor blade channel 121 may extend through both the proximal end and the distal end of the retractor blade 120. In particular, the retractor blade channel 121 may extend through the proximal end of the retractor blade 120 in order to receive the intradiscal shim 450. The retractor blade channel 121 may extend through the distal end of the retractor blade 120 in order to permit the distal end of the intradiscal shim 450 to extend beyond the distal end of the retractor blade 120.

Each intradiscal shim 450 may include shim flanges 460 that traverses longitudinal edges of the intradiscal shim 450 and a shim threaded bore 470 in a proximal end of the intradiscal shim 450. In particular, a proximal edge of each shim flange 460 may be attached to a respective longitudinal edge of the intradiscal shim 450. As such, a distal end of each shim flange 460 may protrude from the longitudinal edge of the intradiscal shim 450. Moreover, the distal end of each shim flange 460 may be sized to closely mate with a respective channel recess 123 when inserted into the retractor blade channel 121.

The shim threaded bore 470 may receive a threaded distal end 482 of a shim insertion tool 480. In particular, the shim insertion tool 480 may comprise an insertion tool shaft 481, an insertion tool handle grip 483, an insertional tool shoulder 484, and an insertion tool collar 486. The insertion tool shaft 481 may comprise a proximal end and the threaded distal end 482. The proximal end of the insertion tool shaft 481 may be coupled to the insertion tool handle grip 483. The insertion tool shoulder 484 may be positioned toward the threaded distal end 482 of the insertion tool shaft 481. In such embodiments, the shim insertion tool 480 may be attached to the intradiscal shim 450 by screwing the threaded distal end 482 into the shim threaded bore 470 until the insertion tool shoulder 484 engages the proximal end of the intradiscal shim 450.

The insertion tool collar 486 may slide along the insertion tool shaft 481. The insertion tool collar 486 may include collar flanges 487 that engage the channel recesses 123 when inserted into the retractor blade channel 121. Moreover, the insertion tool collar 486 may include a shoulder 489 that rests upon the proximal end of the retractor blade 120 when inserted into the retractor blade channel 121. The insertion tool collar 486 may help center the insertion tool shaft 481 in the retractor blade channel 121 while the shim insertion tool 480 properly seats the intradiscal shim 450 in the distal end of the retractor blade 120. The insertion tool collar 486 may reduce risks of damaging the threaded distal end 482 of the insertion tool 480 and may reduce risks of binding the threaded distal end 482 to the intradiscal shim 450.

Thus, a person may insert the intradiscal shim 450 into the retractor blade 120 by screwing the shim insertion tool 480 into the shim threaded bore 470. Using the shim insertion tool 480, a person may insert the intradiscal shim 450 and the insertion tool collar 486 into the retractor blade channel 121 via the proximal end of the retractor blade 120. Via the shim insertion tool 480, the person may further slide the intradiscal shim 450 to the bottom of the retractor blade channel 121 such that the intradiscal shim 450 extends beyond the distal end of the retractor blade 120. After seated against the bottom of the retractor blade channel 121, the person may unscrew the shim insertion tool 480 from the shim threaded bore 470, thus detaching the shim insertion tool 480 from the intradiscal shim 450. The person may then extract the shim insertion tool 480 including the insertion tool collar 486 from the retractor blade channel 121. The process may be essentially reversed to extract the intradiscal shim 450 from a retractor blade channel 121.

Referring now to FIGS. 1A and 1B, each outer retractor arm 130 may include an attachment post 170 at its distal end. The attachment post 170 may comprise a head 172 and a shaft 174. In particular, the attachment posts 170 may extend from the outer retractor arms 130 parallel or substantially parallel to one another. Moreover, the angle α between the outer racks 110 may be set to maintain the attachment posts 170 parallel or substantially parallel to one another as the outer carriages 140 traverse the outer racks 110. See, e.g., FIGS. 1B and 1E.

Figure 1M:
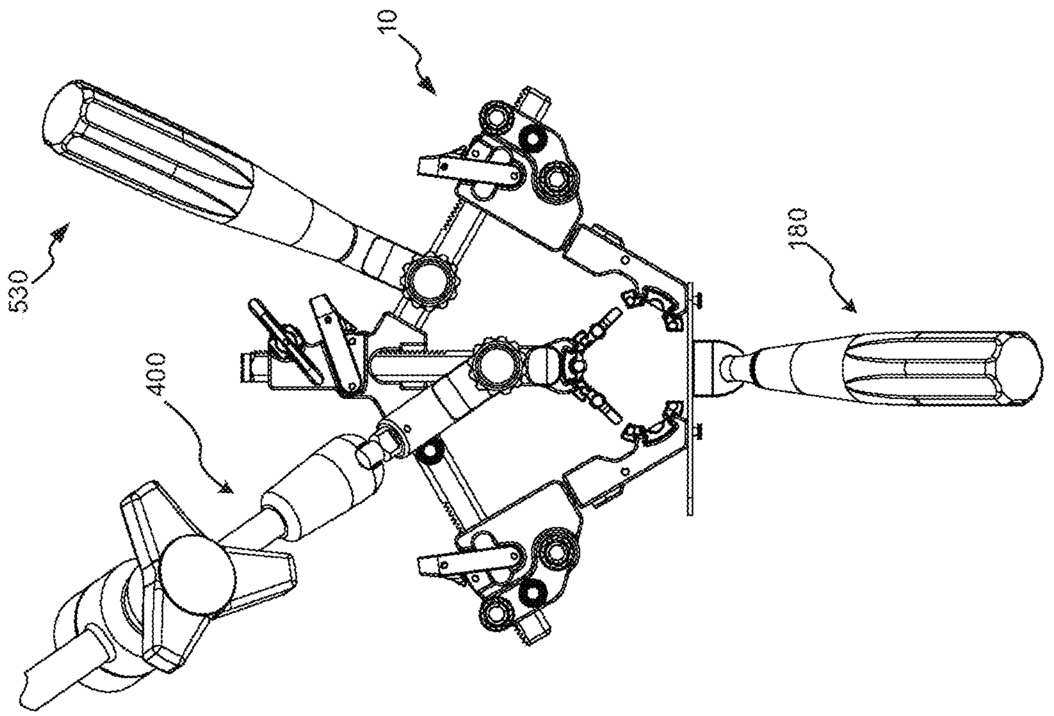
Figure 1L:
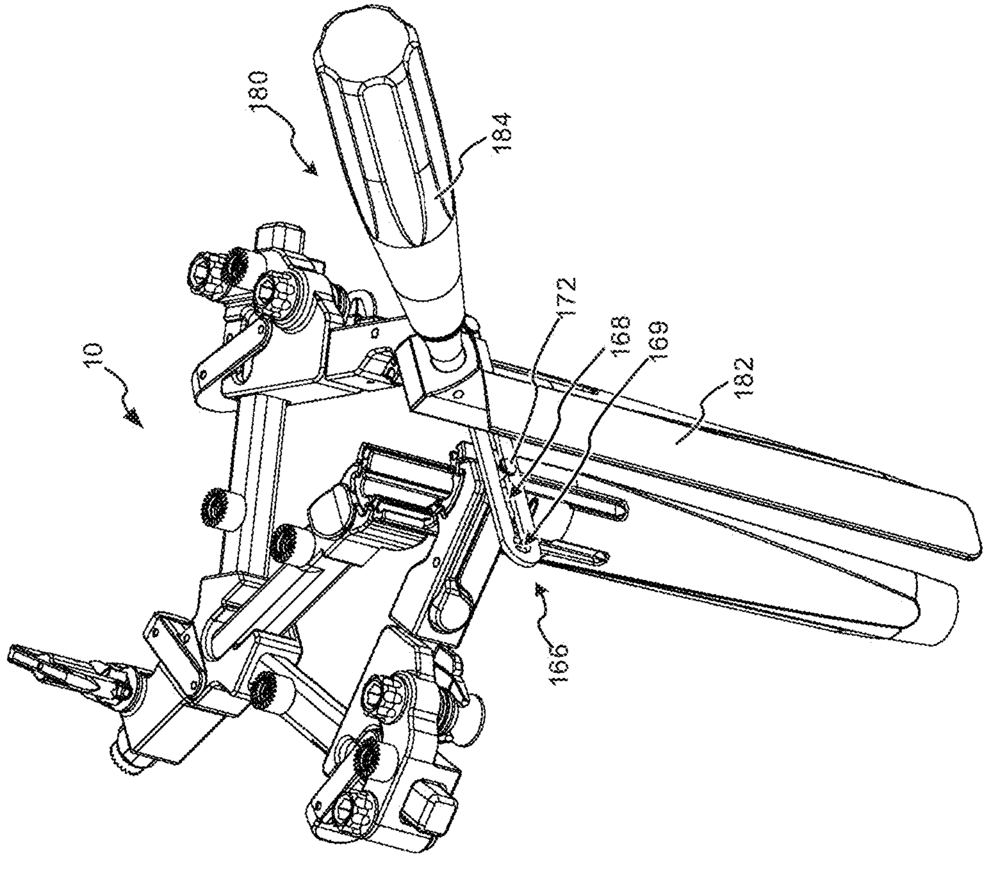

Such attachment posts 170 may permit attaching accessories such as a light, suction device, retractor blades, etc. to the distal ends of the outer retractor arms 130. For example, as shown in FIGS. 1K-1M, a retractor blade 180 may be attached to the distal ends of the outer retractor arms 130 via the attachment posts 170. As shown, the retractor blade 180 may include a blade 182 and a handle 184 coupled to a proximal end of the blade 182. Moreover, the retractor blade 180 may include an attachment plate 166 that laterally traverse a front side of the blade 182. The attachment plate 166 may include a longitudinal slot 168 that traverse a length of the attachment plate 166. Moreover, the attachment plate 166 may include a slot access 169 sized to receive an attachment post 170 and permit receipt of the attachment post 170 into the longitudinal slot 168. In some embodiments, the slot access 169 may be implemented has a hole positioned near an end of the longitudinal slot 168. However, the position of the slot access 169 may be located at other locations along the longitudinal slot 168 in other embodiments. Moreover, the slot access 169 may be implemented as a lateral slot that extends from the longitudinal slot 168 through an upper edge, lower edge, or other edge of the attachment plate 166.

In some embodiments, the slot access 169 may comprise a hole with a diameter slightly larger than the diameter of the attachment post heads 172. Moreover, the longitudinal slot 168 may have a lateral width that is slightly larger than a diameter of the attachment post shafts 174. In this manner, the retractor blade 180 may be attached to the distal ends of the retractor arms 130 by passing the attachment post heads 172 serially through the slot access 169 and sliding the attachment posts 170 along the longitudinal slot 168 with the attachment post shafts 174 in close engagement with sidewalls of the longitudinal slot 168.

Referring now to FIGS. 5A-5G, another accessory suitable for attaching to distal ends of outer retractor arms 130 is shown. In particular, a fan blade 500 is depicted. The fan blade 500 may include a stack of planar blades 510, an attachment plate 520, and a handle 530. The attachment plate 520 may include a longitudinal slot 522, a slot access 524, and a notch 526. The longitudinal slot 522 may traverse a portion of the attachment plate 520. The notch 526 may lateral extend from a lower edge of the attachment plate 520 toward a central portion of the attachment plate 520. The lateral width of the notch 526 may be greater than the diameter of an attachment post shaft 174, but less than the diameter an attachment post head 172. As such, the notch 526 may receive an attachment post shaft 174 and retain the received attachment post 170 since the attachment post head 172 is too large to pass through the notch 526.

As shown, the slot access 524 to the longitudinal slot 522 may be implemented as a hole positioned near an end of the longitudinal slot 522. However, the position of the slot access 524 may be located at other locations along the longitudinal slot 522 in other embodiments. Alternatively, the slot access 524 may be implemented as a lateral slot that extends from the longitudinal slot 522 through an upper edge, lower edge, or other edge of the attachment plate 520. In some embodiments, the slot access 524 may comprise a hole with a diameter slightly larger than the diameter of an attachment post head 172. Moreover, the longitudinal slot 522 may have a lateral width that is slightly larger than a diameter of an attachment post shaft 174. In this manner, the fan blade 500 may be attached to the distal ends of the retractor arms 130 by passing an attachment post head 172 through the slot access 524, sliding the attachment post 170 along the longitudinal slot 168 with the attachment post shaft 174 in close engagement with sidewalls of the longitudinal slot 168, placing the notch 526 over the attachment post shaft 174 of the other attachment post 170, and sliding the notch 526 over the attachment post shaft 174.

A fastener 512, such as a screw, may pass through pivot holes at a proximal end of the blades 510 and pivotally attach the blades 510 to a handle mount 532 of the handle 530. In particular, the fastener 512 may include a threaded shaft the mates with a threaded bore of the handle mount 532 and a head 514 that confines the blades 510 between the head 514 and the handle mount 532. As a result of such attachment, the blades 510 may be pivoted about the fastener 512 in order to fan out distal ends of the blades 510 as shown in FIGS. 5A-5D.

Figure 5B:
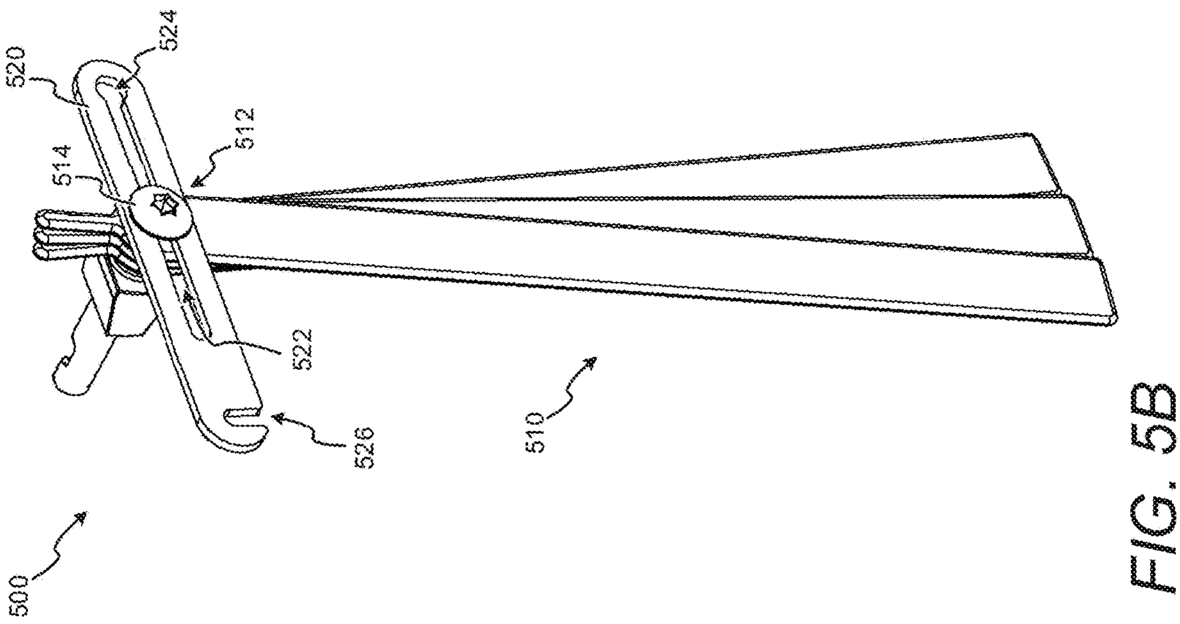
FIGS. 5A-5G provide various views of a fan blade and its attachment to a retractor system of FIGS. 1A-1M.
Figure 5A:
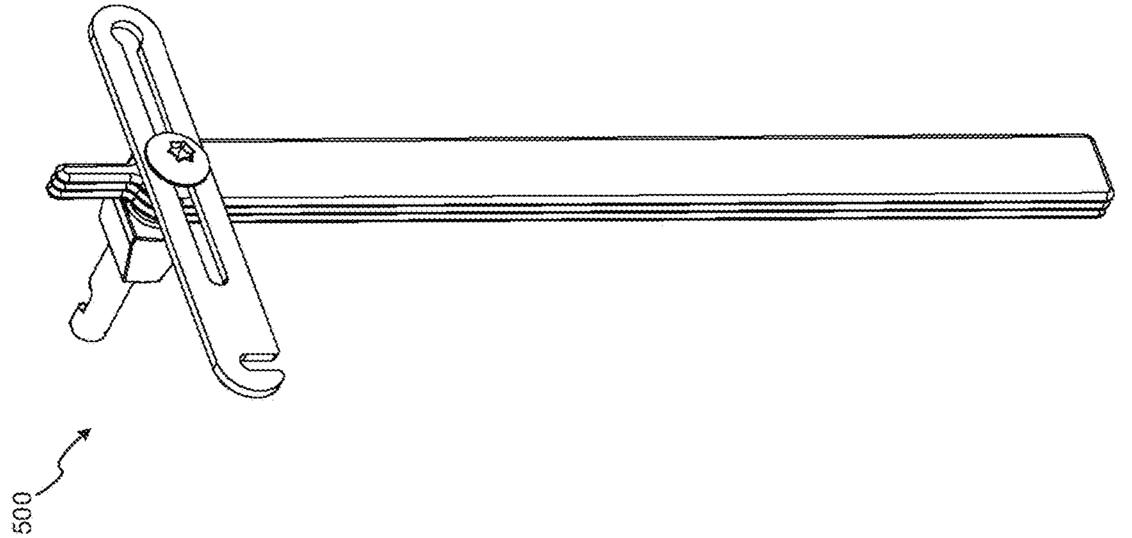
Figure 5D:
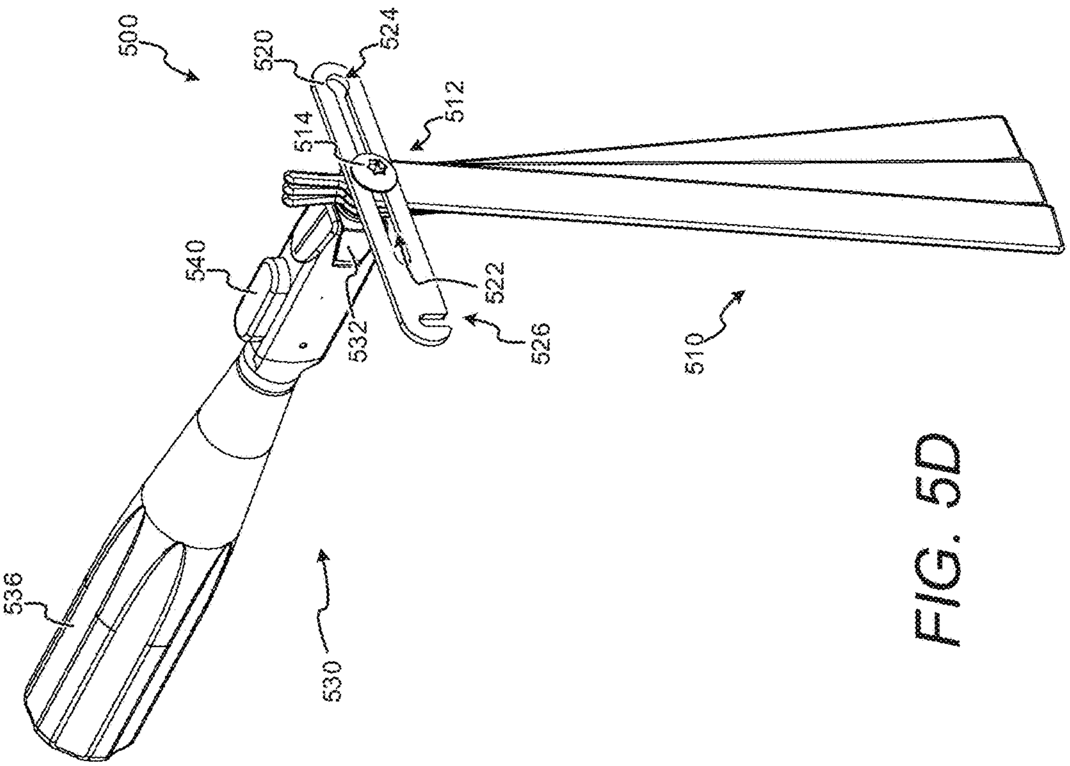
Figure 5C:
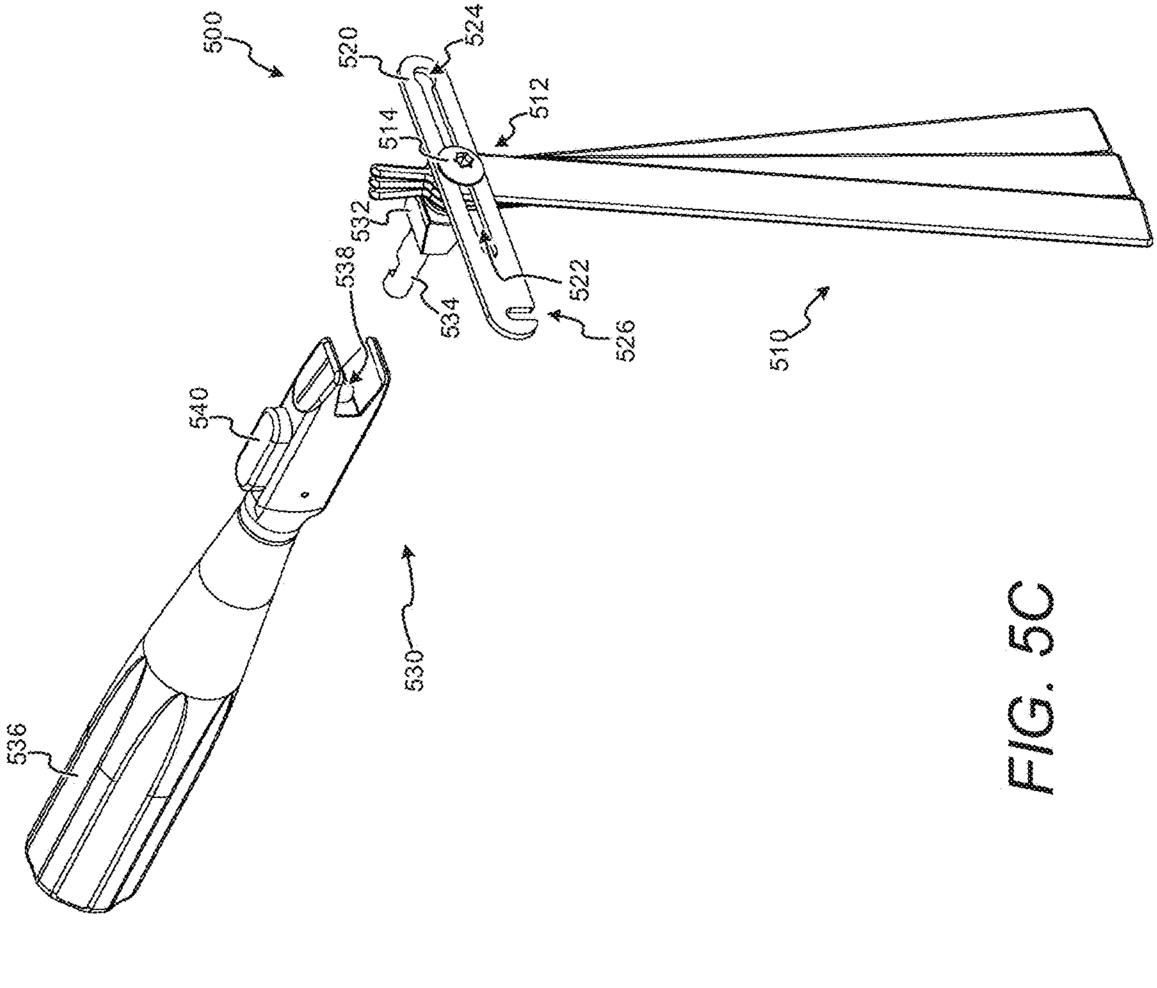
Figure 5G:
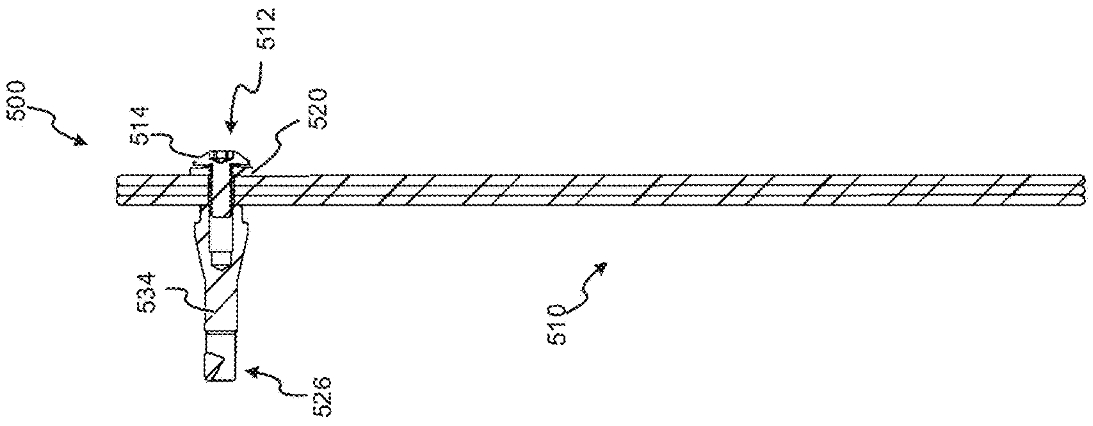
Figure 5F:
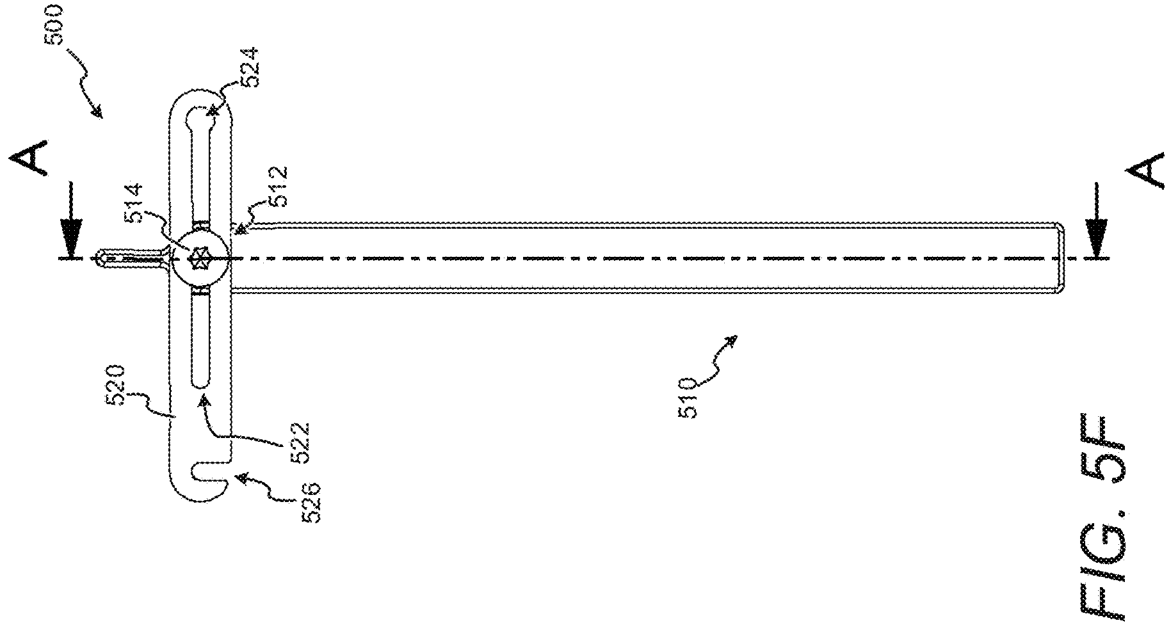
Figure 5E:
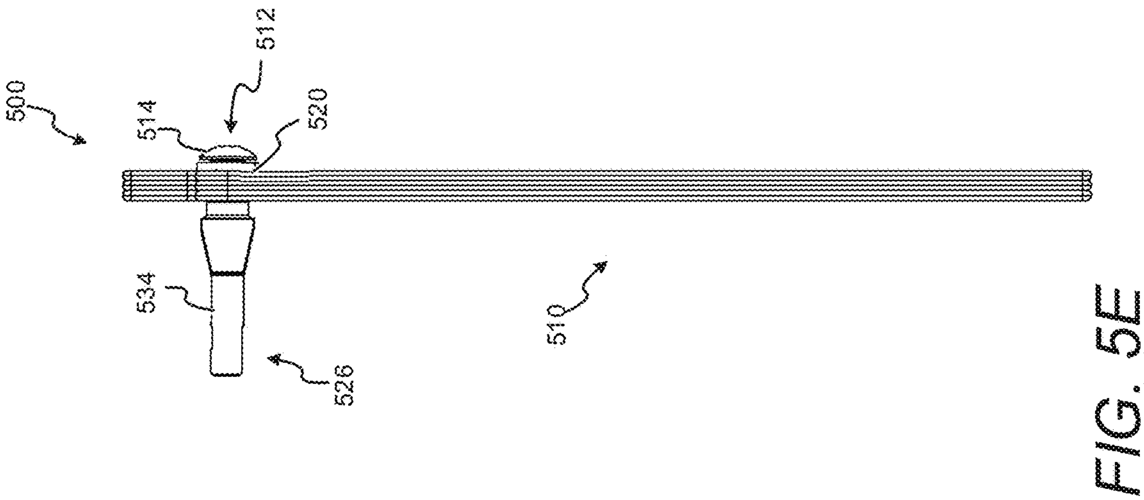
Figure 6C:
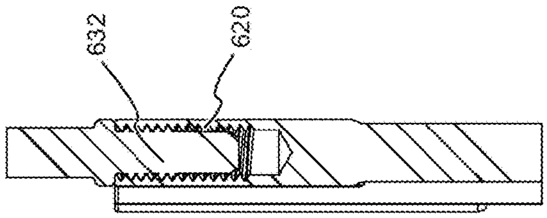
FIGS. 6A-6J provide various views of a blade fin, its attachment to a retractor blade of FIGS. 1A-1M, and a tool for attaching the blade fin.
Figure 6B:
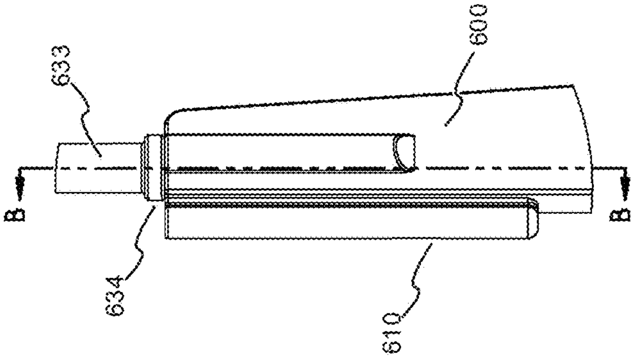
Figure 6A:
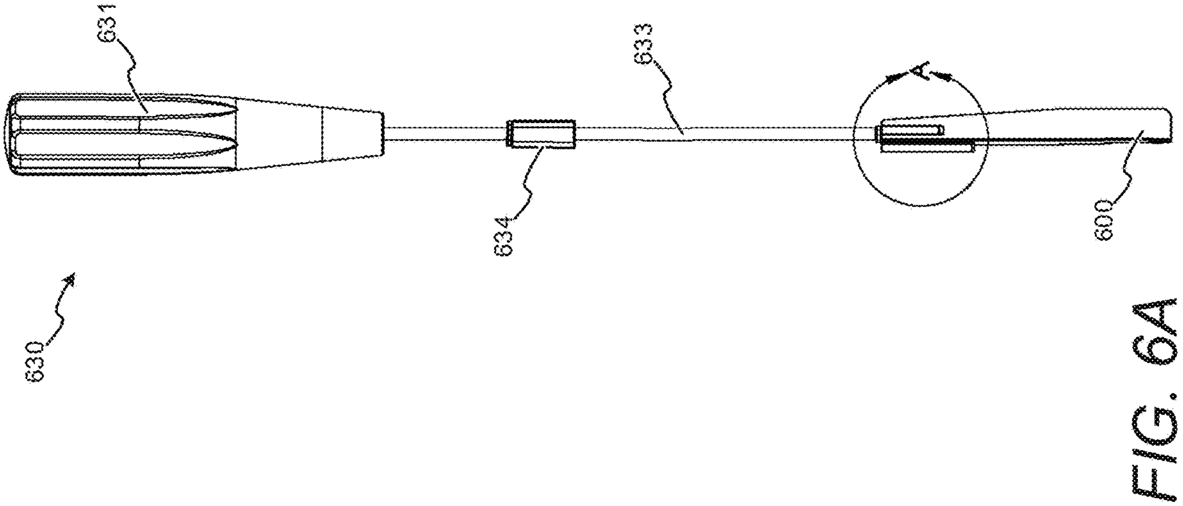
Figure 6D:
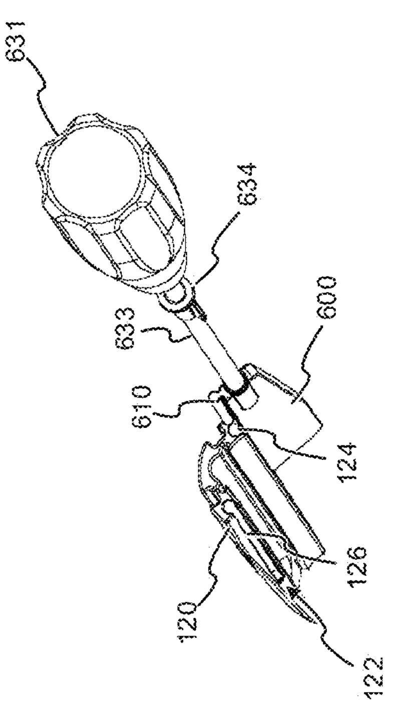
Figure 6E:
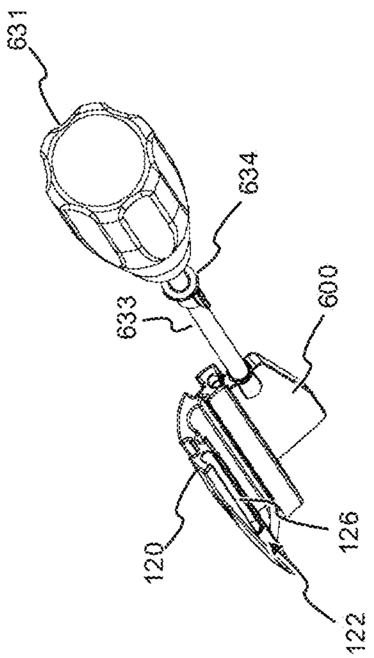
Figure 6F:
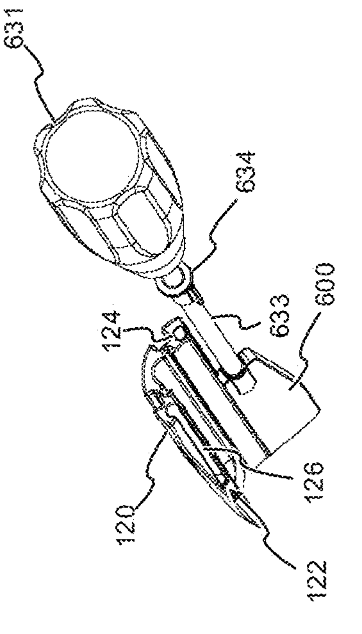
Figure 6G:
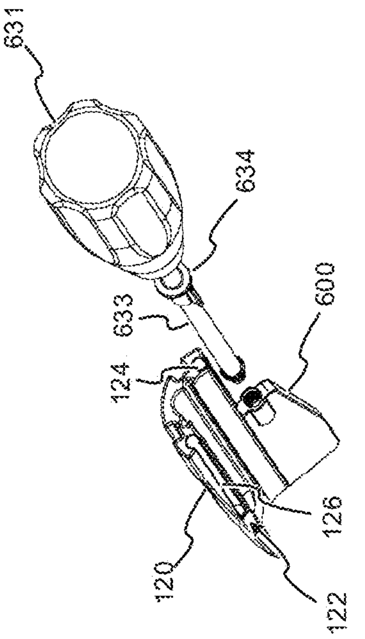
Figure 6I:
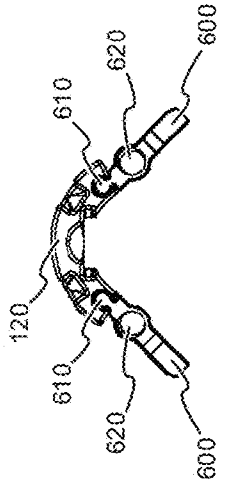
Figure 6J:
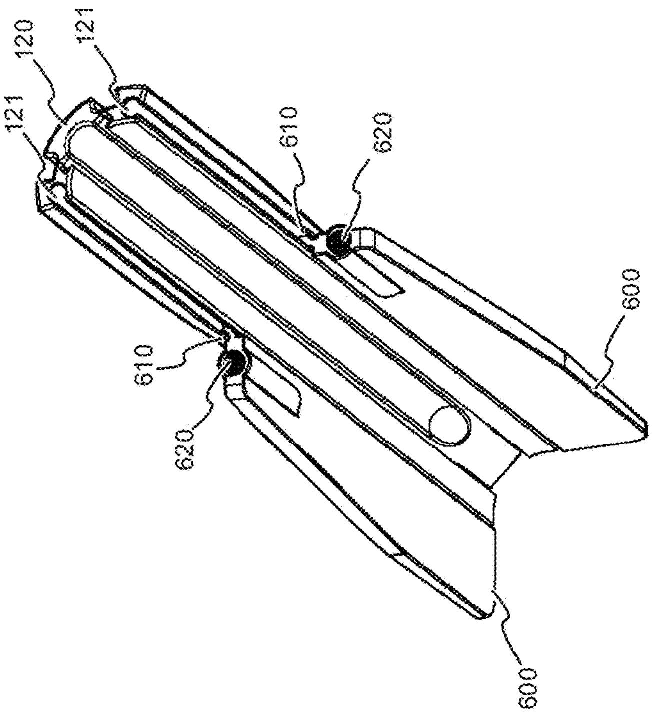
Figure 6H:
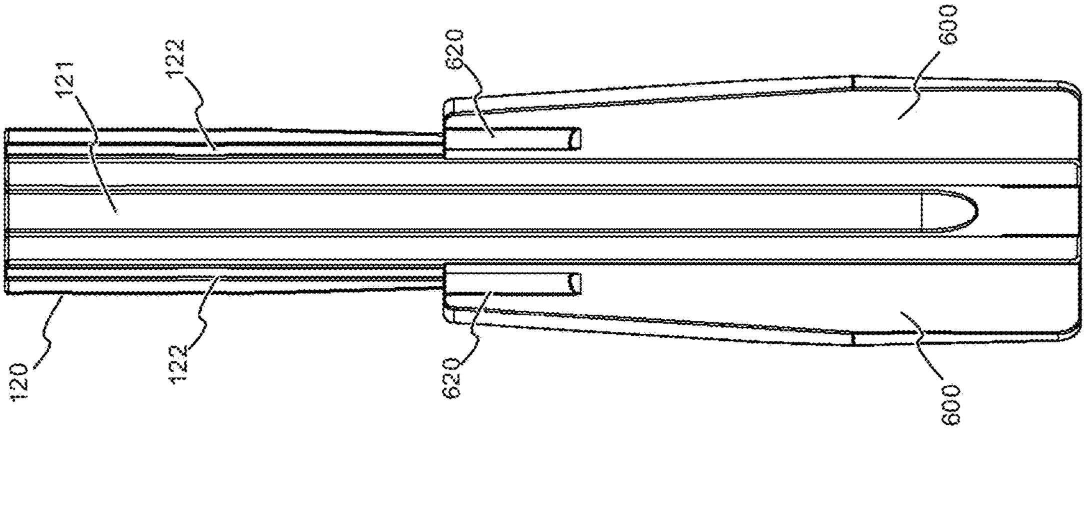

As shown in FIG. 5C, the handle 530 may comprise the handle mount 532, a handle shaft 537, and a handle grip 536. The handle mount 532 of the handle 530 may include a notched shaft 534. Moreover, the handle shaft 537 may comprise a shaft bore 538 in a distal portion of the handle shaft 537. The shaft bore 538 in the distal portion of the handle shaft 537 may be sized to receive the notched shaft 534 of the handle mount 532. The distal portion of the handle shaft 537 may include a spring-biased pawl (not shown) having a distal end that extends into the shaft bore 538 and catches the notch of the notched shaft 534 when inserted into the shaft bore 538. A handle release button 540 of the handle 530 may be pressed to retract the distal end of the pawl from the shaft bore 538 and disengage the distal end of the pawl from the notched shaft 534. Thus, by pressing the handle release button 540, a person may release the handle 530 from the handle mount 532 and remove the handle 530 from the fan blade 500.

The blades 180, 500 are shown with different attachment plates 166, 520 and different handles 184, 530. However, in various embodiments, the blades 180, 500 may be implemented using either attachment plate 166, 520 and/or handle 184, 530.

As shown in FIGS. 6A-6J, a retractor blade 120 may include fin channels 122 that are configured to receive blade fins 600. The blade fins 600 may be attached to the retractor blades 120 via the fin channels 122 to effectively extend a lateral width of the retractor blades 120. See, e.g., FIGS. 1K and 1M. To this end, each fin channel 122 may traverse a longitudinal side of a retractor blade 120. Each fin channel 122 may include a fin channel opening 124 at the proximal end of the retractor blade 120. Moreover, each fin channel 122 may include a longitudinal opening 126 that runs along at least a portion of the longitudinal side of the retractor blade 120. Each fin channel opening 124 may have a lateral width that is greater than the lateral width of the longitudinal openings 126.

Each blade fin 600 may include a blade fin flange 610 that traverses a longitudinal edge of the blade fin 600 and a blade fin threaded bore 620 in a proximal end of the blade fin 600. In particular, a proximal edge of the blade fin flange 610 is attached to the blade fin 600 along a longitudinal edge of the blade fin 600. As such, a distal end of the blade fin flange 610 protrudes from the longitudinal edge of the blade fin 600. Moreover, the distal end of the blade fin flange 610 may be keyed to closely mate with the fin channel opening 124 in the proximal end of the retractor blade 120. Further, the proximal and intermediary portions of the flange 610 may be sized to closely mate with the longitudinal openings 126 along the longitudinal edge of the retractor blade 120. Thus, the keyed distal end of the blade fin flange 610 may be enlarged with respect to the proximal and intermediary portions of the blade fin flange 610. Thus, once inserted into the fin channel 122 via the fin channel opening 124, the blade fin flange 610 may be laterally confined within the fin channel 122 since the keyed distal end is too large to be laterally removed from the fin channel 122 via the longitudinal openings 126.

The blade fin threaded bore 620 may receive a threaded end 632 of a fin insertion tool 630. In particular, the fin insertion tool 630 may include a handle grip 631 and an insertion tool shaft 633 comprising a proximal end couple to the handle grip and a distal end providing the threaded end 632 of the fin insertion tool 630. Via rotation of the handle grip 631, the threaded end 632 may be screwed into the blade fin threaded bore 620. In some embodiments, the fin insertion tool 630 may include an insertion tool shoulder 634 toward the threaded end 632. In such an embodiment, the fin insertion tool 630 may be properly seated or attached to the blade fin 600 by screwing the threaded end 632 into the fin threaded bore 620 until the insertion tool shoulder 634 engages the proximal end of the blade fin 600. In some embodiment, the shim insertion tool 480 may be used as the fin insertion tool 630.

In particular, the fin insertion tool 630 may comprise an insertion tool handle grip 631, an insertion tool shaft 633, an insertional tool shoulder 634, and an insertion tool collar 636. The insertion tool shaft 633 may comprise a proximal end and the threaded distal end 632. The proximal end of the insertion tool shaft 633 may be coupled to the insertion tool handle grip 631. The insertion tool shoulder 634 may be positioned toward the threaded distal end 632 of the insertion tool shaft 633. In such embodiments, the fin insertion tool 630 may be attached to the blade fin 600 by screwing the threaded distal end 632 into the fin threaded bore 620 until the insertion tool shoulder 634 engages the proximal end of the blade fin 600.

A person may attach a blade fin 600 to the retractor blade 120 by screwing the fin insertion tool 630 into the fin threaded bore 620. Using the fin insertion tool 630, a person may insert the keyed distal end of the blade fin flange 610 into the fin channel opening 124 in the proximal end of the retractor blade 120. Via the fin insertion tool 630, the person may further slide the blade fin 600 to the bottom of the fin channel 122. After seated against the bottom of the fin channel 122, the person may unscrew the fin insertion tool 630 from the fin threaded bore 620 and detach the fin insertion tool 630 from the blade fin 600. The process may be essentially reversed to remove a blade fin 600 from the fin channel 122 of the retractor blade 120. In some embodiment, a same insertion tool may be used as the shim insertion tool 480 and the fin insertion tool 630, thus the depiction of a collar similar to collar 486 of shim insertion tool 480 in FIG. 6A.

Figure 7B:
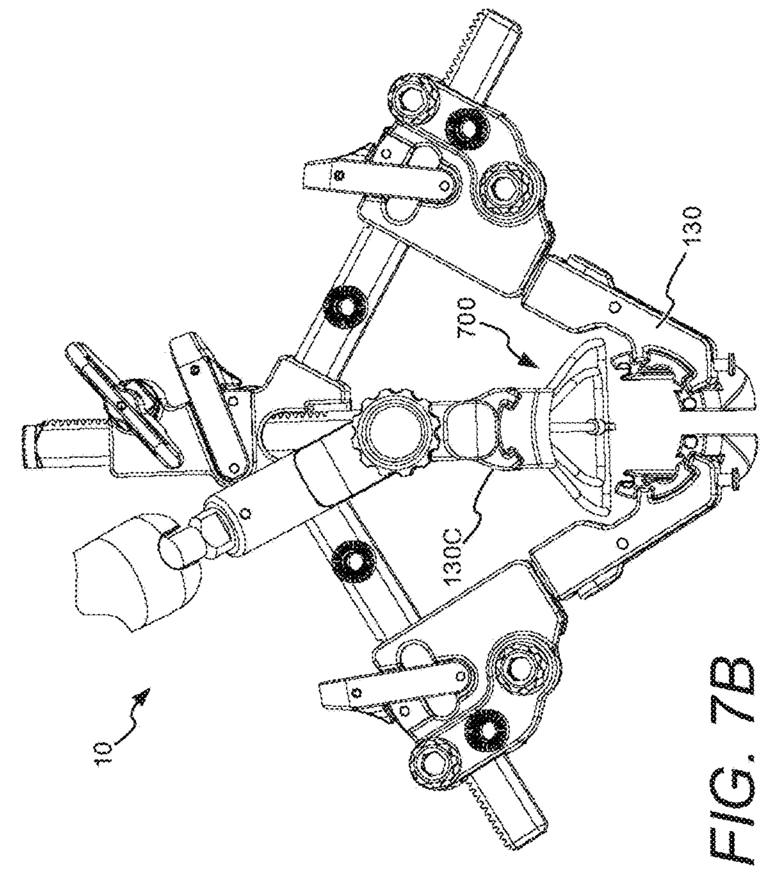
FIGS. 7A-7C provide various views depicting a lung blade and attachment of a lung blade to the retractor system of FIGS. 1A-1M.
Figure 7C:
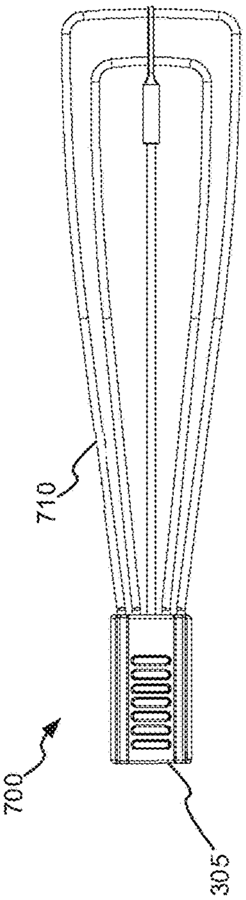
Figure 7A:
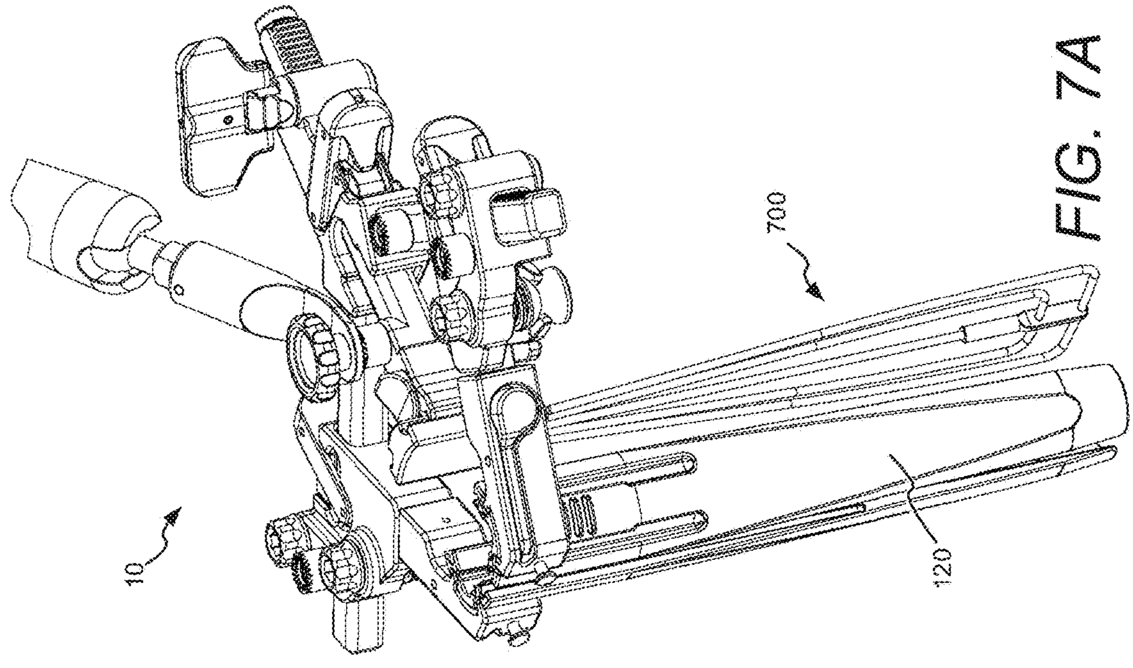

As shown in FIGS. 7A-7C, other types of blades may be used with the retractor system 10 of FIGS. 1A-1M. For example, a lung blade 700 may be attached to the central retractor arm 130C for certain procedures such a when accessing the thoracic spine. The lung blade 700, similar to the retractor blades 120, may be a telescoping blade. In particular, the lung blade 700 may include a proximal portion with a retractor blade track 305 along the back side of the lung blade 700, which engages the retractor arm channel 270 of the central retractor arm 130C or the retractor arm channel 270 of one or the outer retractor arms 130. In this manner, the central retractor arm 130C may traverse the retractor blade track 305 to adjust a vertical positioning of the lung blade 700 within the operative site. As further shown, the lung blade 700 may comprise several rods 710 that extends from the proximal portion to define a mesh-like blade. In the depicted embodiment, the front and back surfaces of the lung blade 700 are primarily open space. However, other embodiments may include additional rods 710 and/or other structures resulting in the front surface and/or the back surface having a lesser amount of open space.

Figure 8B:
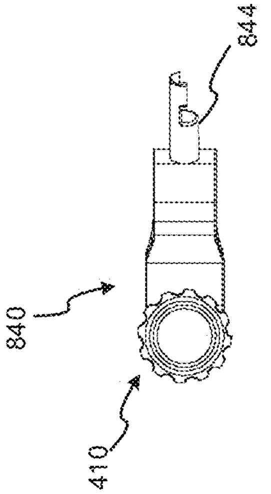
FIGS. 8A-8C provide various views of a handle and a quick connect mount for attaching the handle to the retractor system of FIGS. 1A-1M.
Figure 8C:
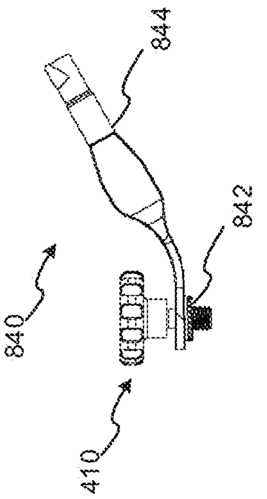
Figure 8A:
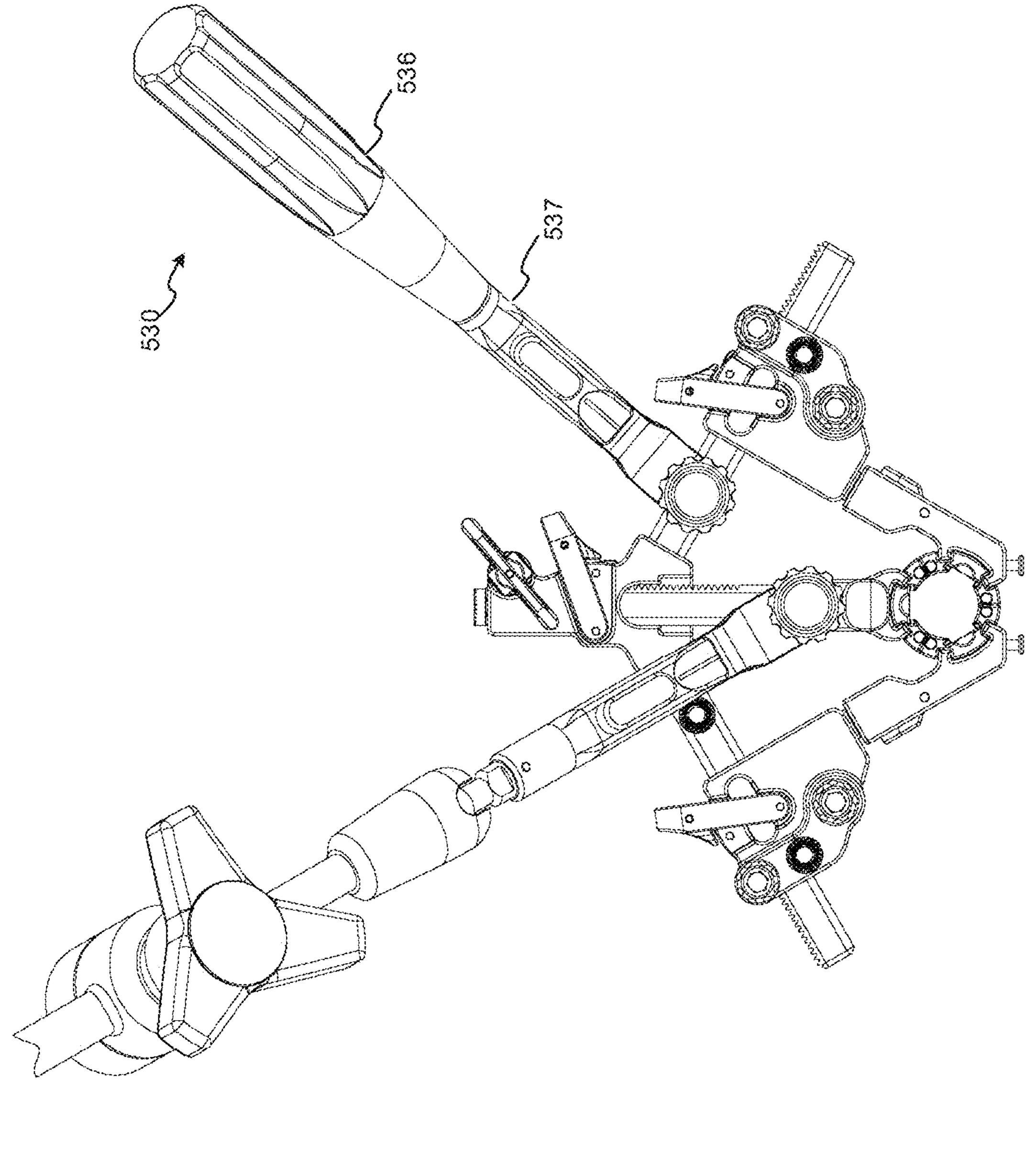

Referring now to FIG. 8A-8C, a handle 530 and quick connect mount 840 are shown. In particular, the handle 530 may be attached to a connector 160 on a top surface of an outer rack 110 via the quick connect mount 840. The handle 530 may include a handle grip 536 attached to a handle shaft 537. Moreover, a distal end of the handle shaft 537 may include a shaft bore 538 sized to receive a notched shaft 844 of the quick connect mount 840. A distal portion of the handle shaft 537 may also include a spring-biased pawl (not shown) having a distal end that extends into the shaft bore 538 and catches the notch of the notched shaft 844 when the shaft bore 538 receives the notched shaft 844. A handle release button 540 of the handle 530 may retract the pawl from the bore 538 and may disengage the pawl from the notched shaft 844 when pressed. Thus, by pressing the handle release button 540, a person may release the handle 530 from the mount 840 and remove the handle 530 from the retractor system 10 while leaving the quick connect mount 840 attached to the connector 160.

The quick connect mount 840 may include a knob 410 with a threaded shaft 412 that passes through a base portion of the quick connect mount 840. Moreover, the base portion of the quick connect mount 840 may include a serrated surface 842 that circumscribes the threaded shaft 412. Thus, the quick connect mount 840 and its notched shaft 844 may be attached to any one of the connectors 160 in a similar manner as the articulated arm 400. Namely, a person may turn the knob 410 by hand in order to screw the knob 410 into the connector 160 and tightly engage the serrated surface 842 of the quick connect mount 840 with the serrated surface 164 of the connector 160. Such engagement between serrated surfaces may lock the quick connect mount 840 to the connector 160 in a manner that prevents rotation of the quick connect mount 840 with regard to the connector 160. Once the quick connect mount 840 is secured to the connector 160, a person may quickly attach and detach the handle 530 to the retractor system 10 via the quick connect mount 840.

Figure 10B:
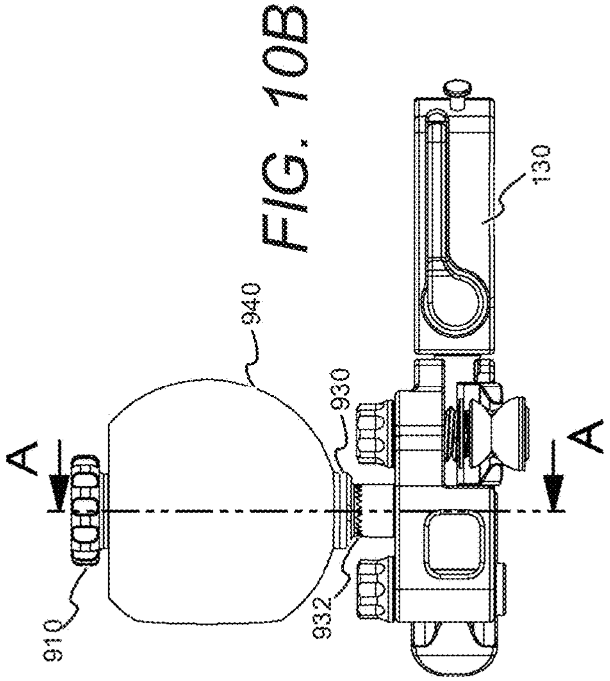
FIGS. 10A-10C provide various views for a handle and its attachment to the retractor of FIGS. 1A-1M.
Figure 10A:
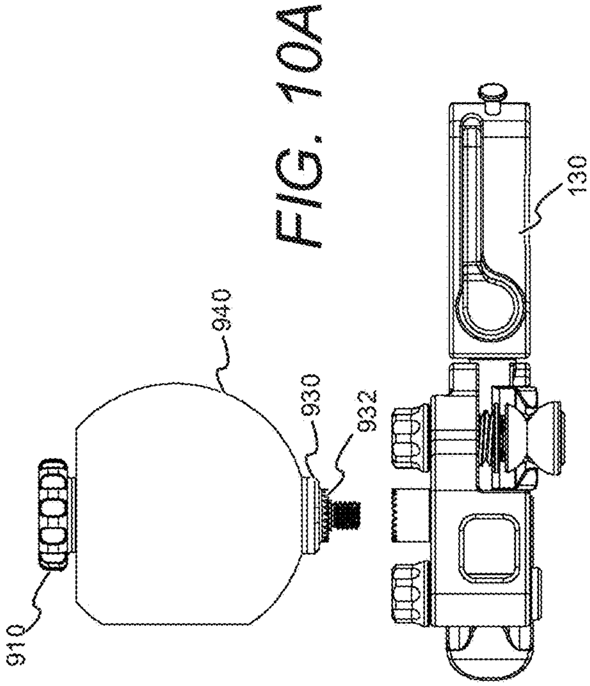
Figure 10C:
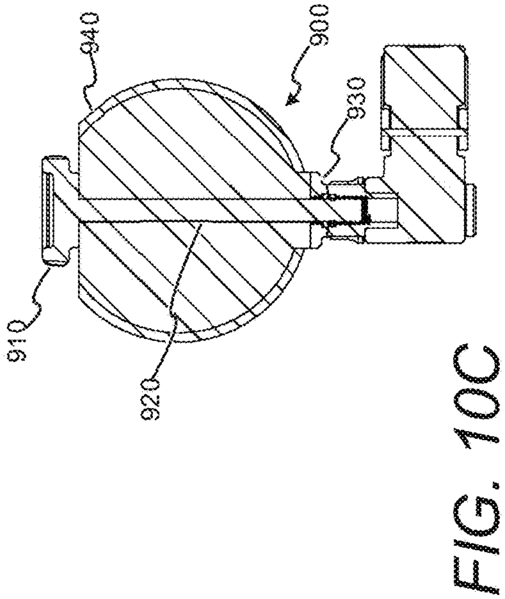

Referring now to FIG. 10A-10C, a handle 900 is shown attached to a connector 160 on a top surface of an outer carriage 140. The handle 900 may include a head 910, a threaded shaft 920, a handle base 930, and a handle grip 940. The threaded shaft 920 may pass through the handle grip 940 and handle base 930, thus confining the handle grip 940 between the head 910 and the handle base 930. A bottom side of the handle base 930 may include a serrated surface 932 that circumscribes the threaded shaft 920.

In one embodiment, the handle grip 940 is formed by over-molding the threaded shaft 920 in silicone to form a spherical handle grip. However, in some embodiments, the handle grip 940 may be formed from different materials and/or a different process. Moreover, the handle grip 940 may be formed to have different shapes (e.g., a screw driver handle grip).

Thus, the handle 900 and its handle grip 940 may be attached to any one of the connectors 160 in a similar manner as the knob 410. Namely, a person may turn the handle 900 by hand via the head 910 and/or the handle grip 940 in order to screw the threaded shaft 920 into the connector 160 and tightly engage the serrated surface 932 with the serrated surface 164 of the connector 160. Such engagement between serrated surfaces may lock the handle 900 and its handle grip 940 to the connector 160 in a manner that prevents rotation of the handle 900 and its handle grip 940 with regard to the connector 160. While the handle 900 is shown with a head 910 suitable for turning by hand, the head 910 in some embodiments may be designed for turning with a tool. For example, the head 910 may include a keyed recess or may be replaced with a head having a keyed recess sized to receive a tool. A person, via the aid of such a tool, may then turn the head 910 to attach the handle 900 to the connector 160. Once secured to the connector 160, a person may grasp the head 910 and/or handle grip 940 to position the retractor system 10.

Figure 2A:
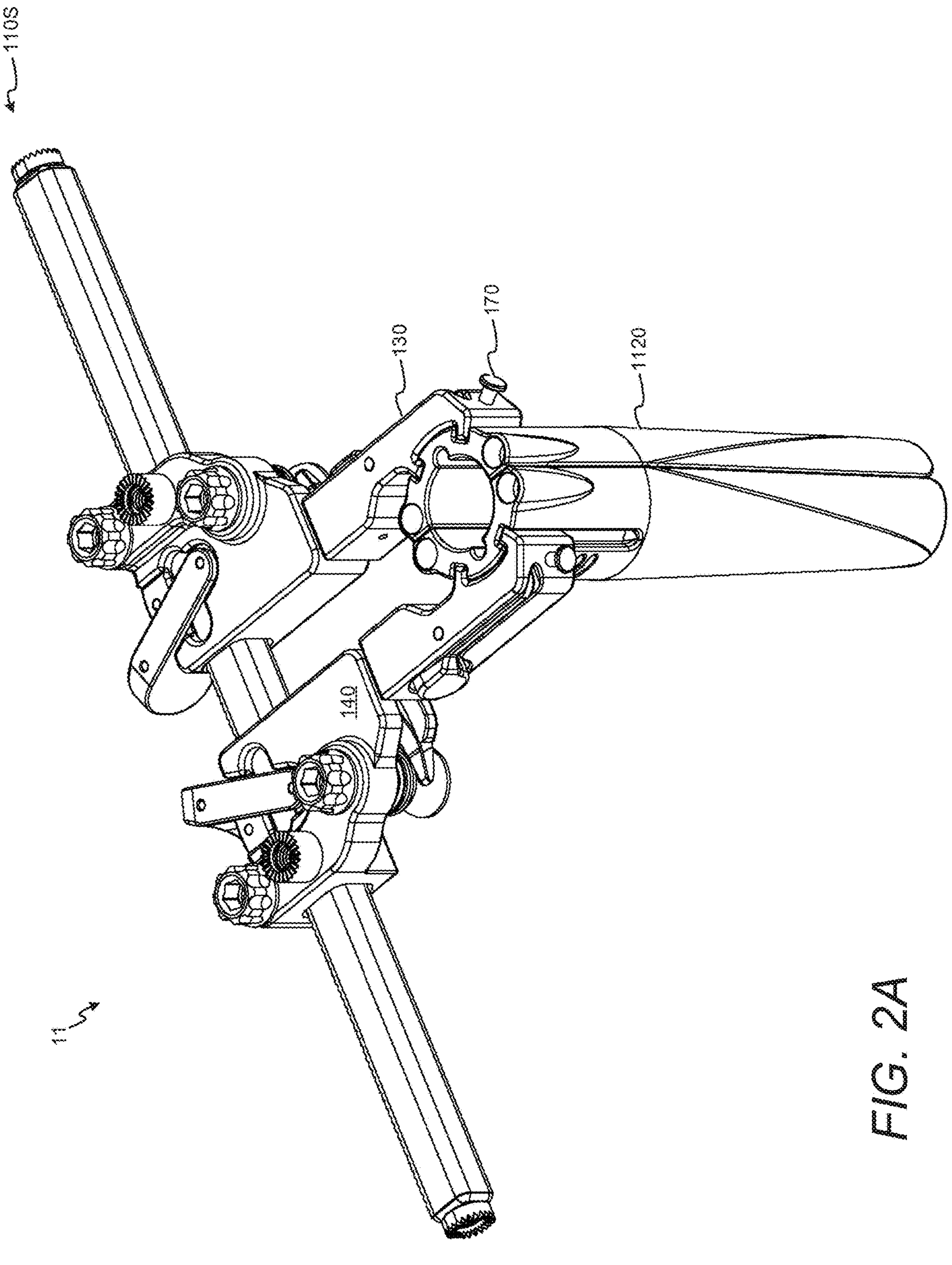
FIGS. 2A-2S provide various views of a retractor system in accordance with aspects of the present disclosure.
Figure 2B:
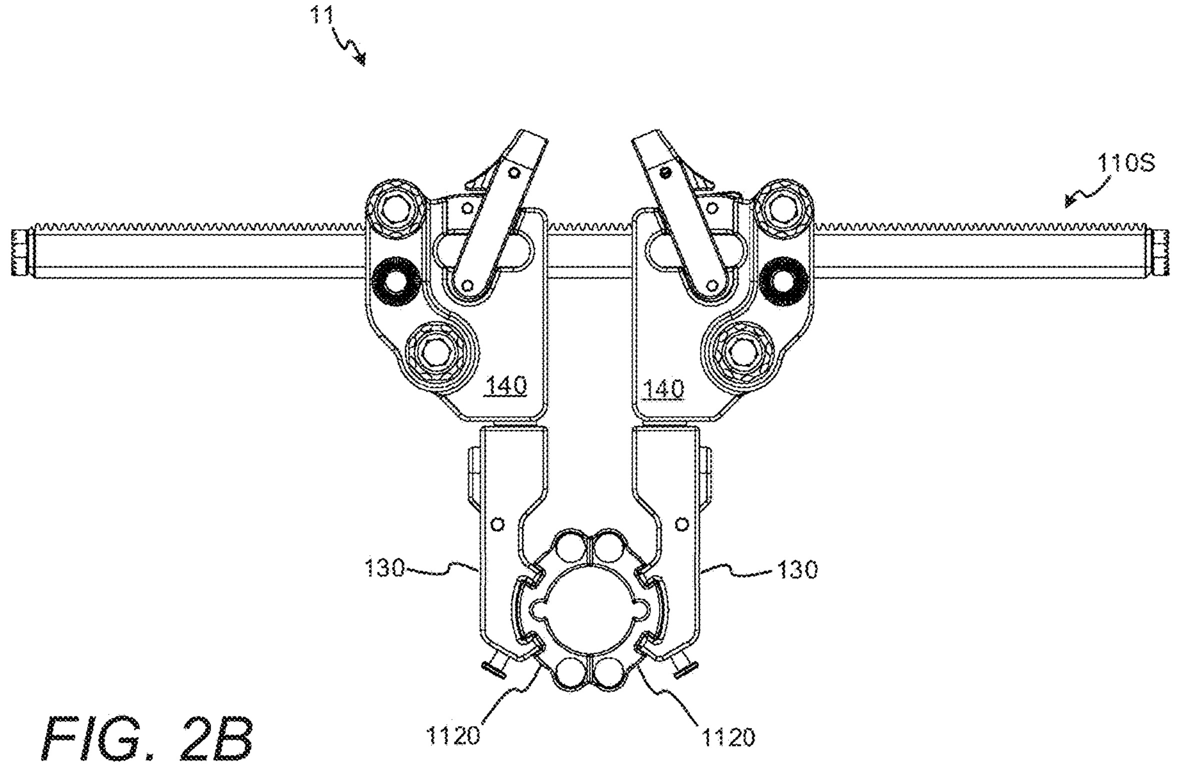
Figure 2C:
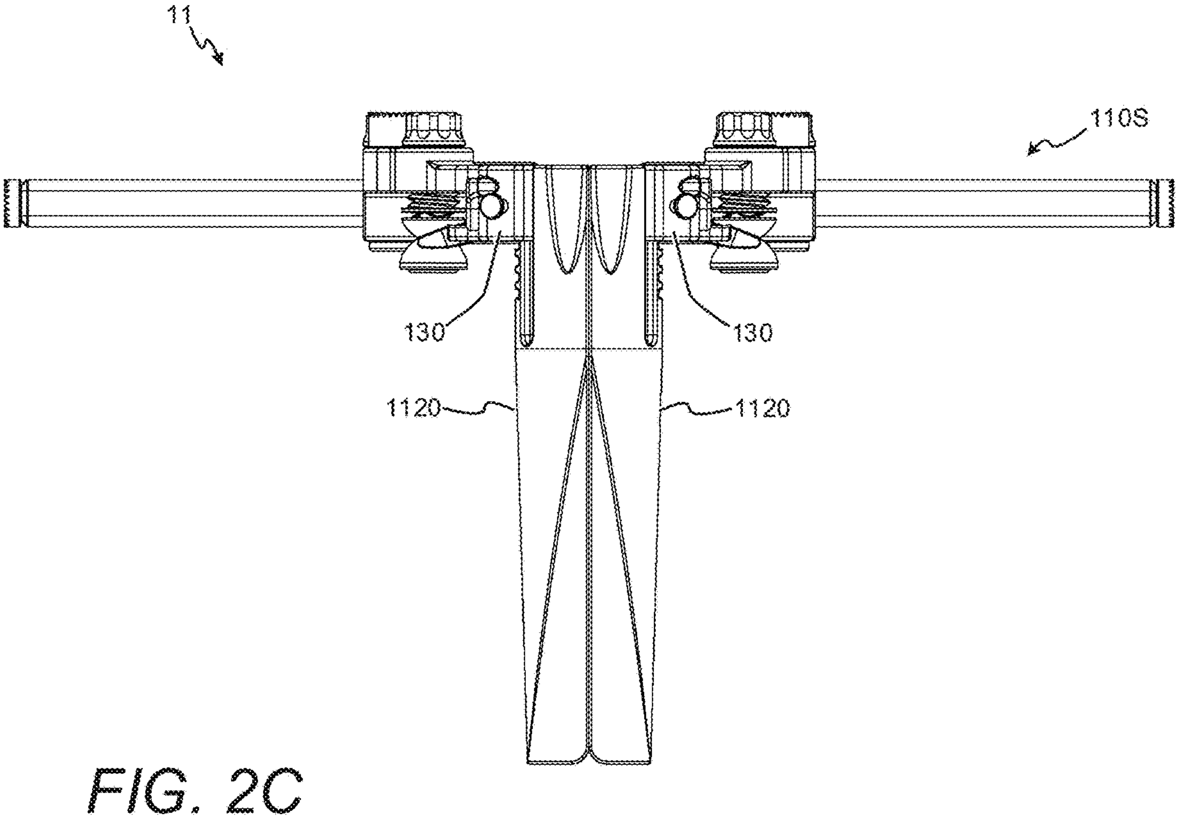
Figure 2D:
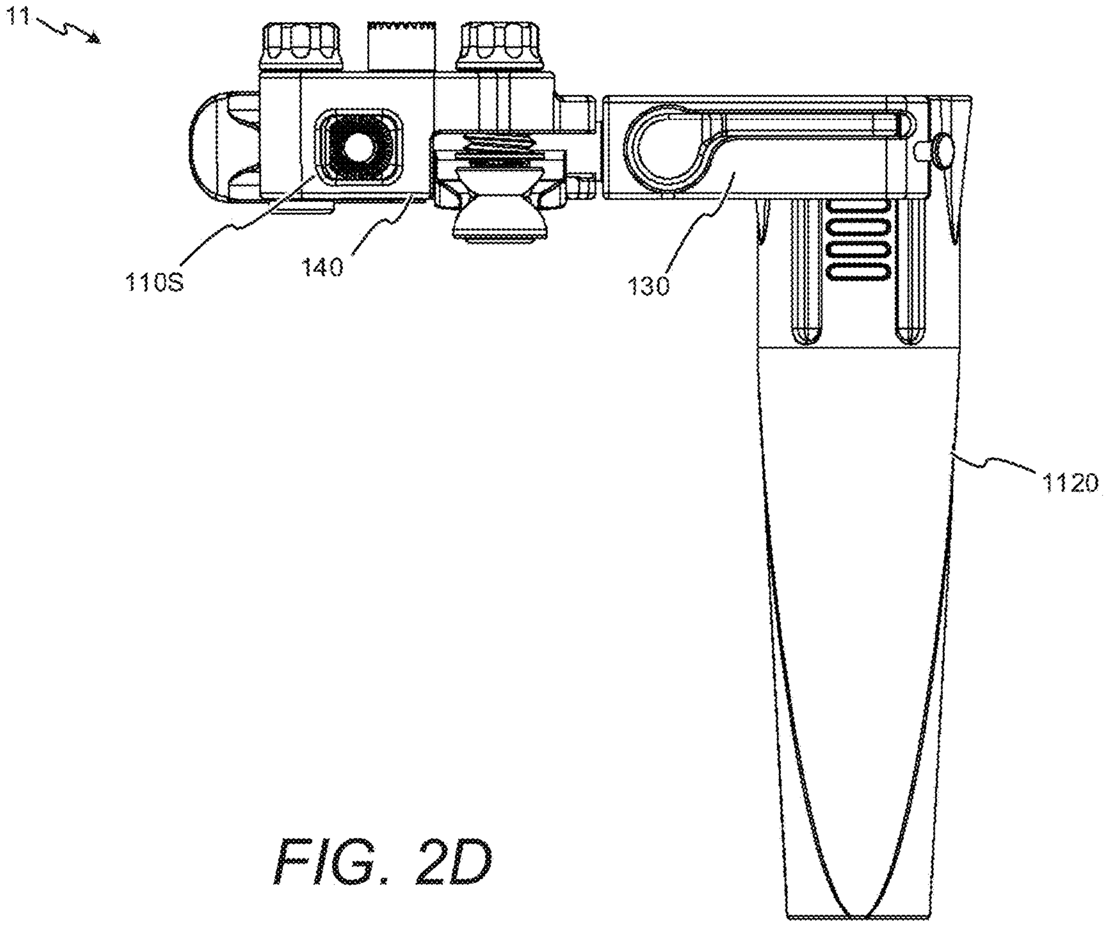
Figure 2E:
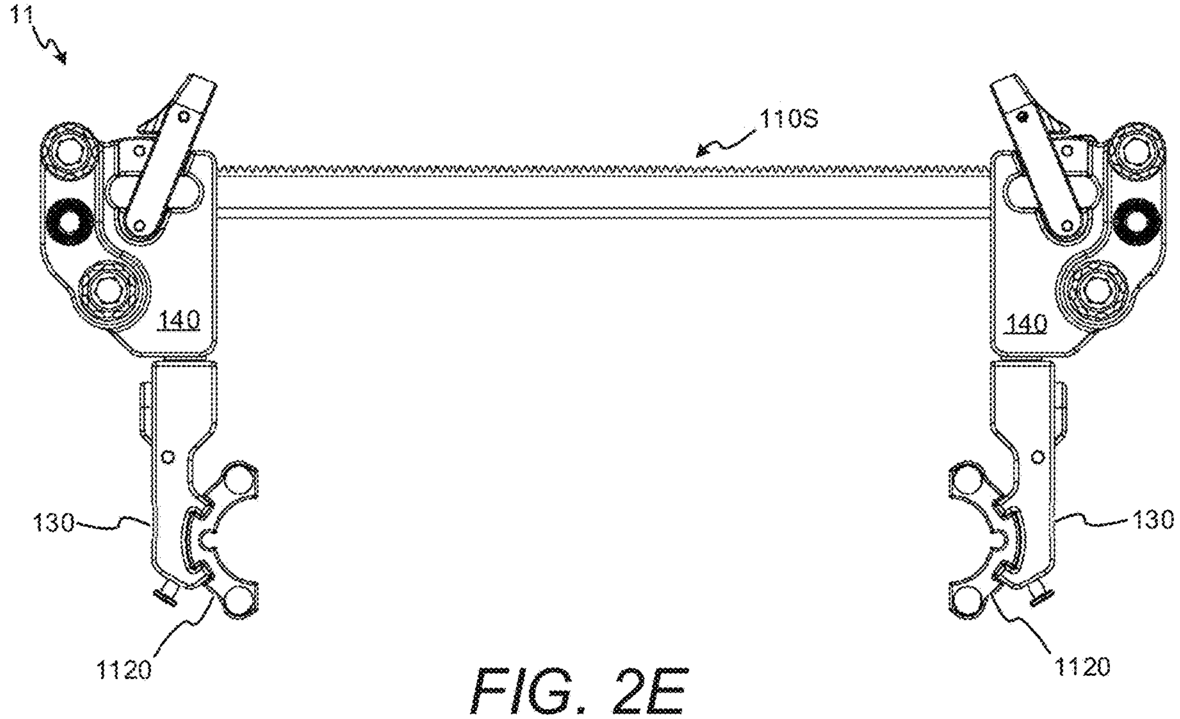
Figure 2F:
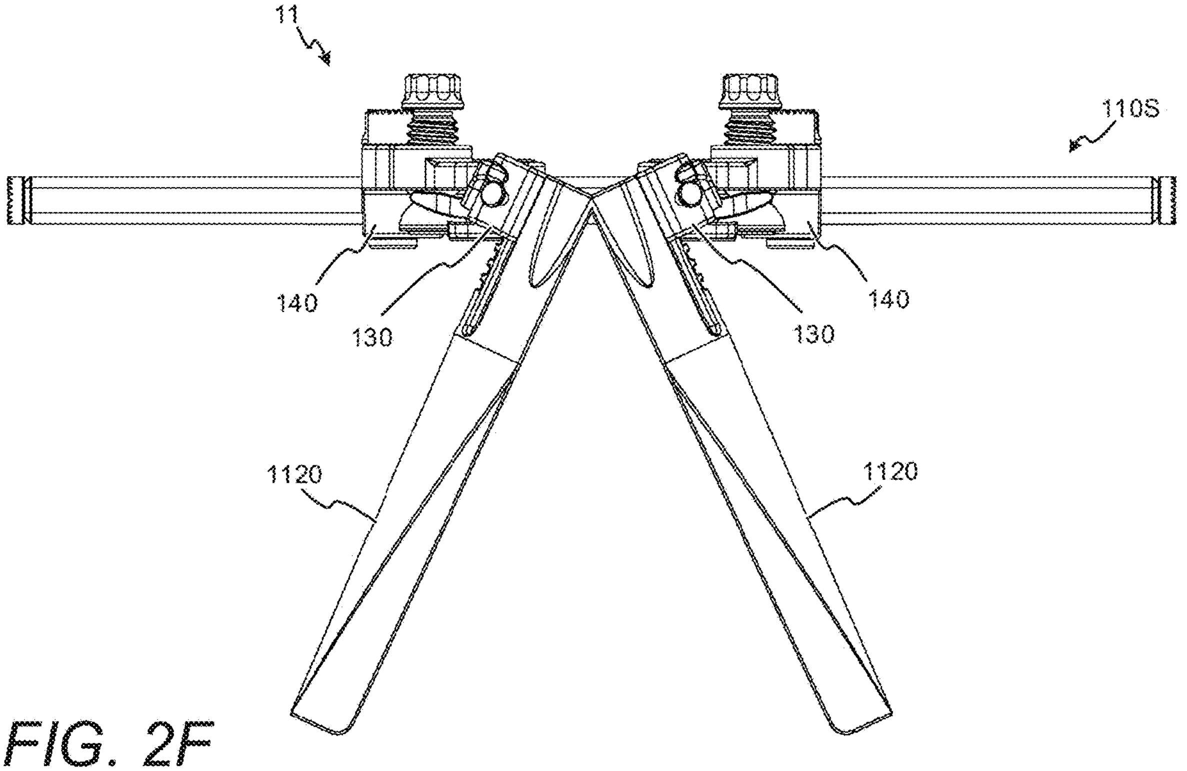
Figure 2G:
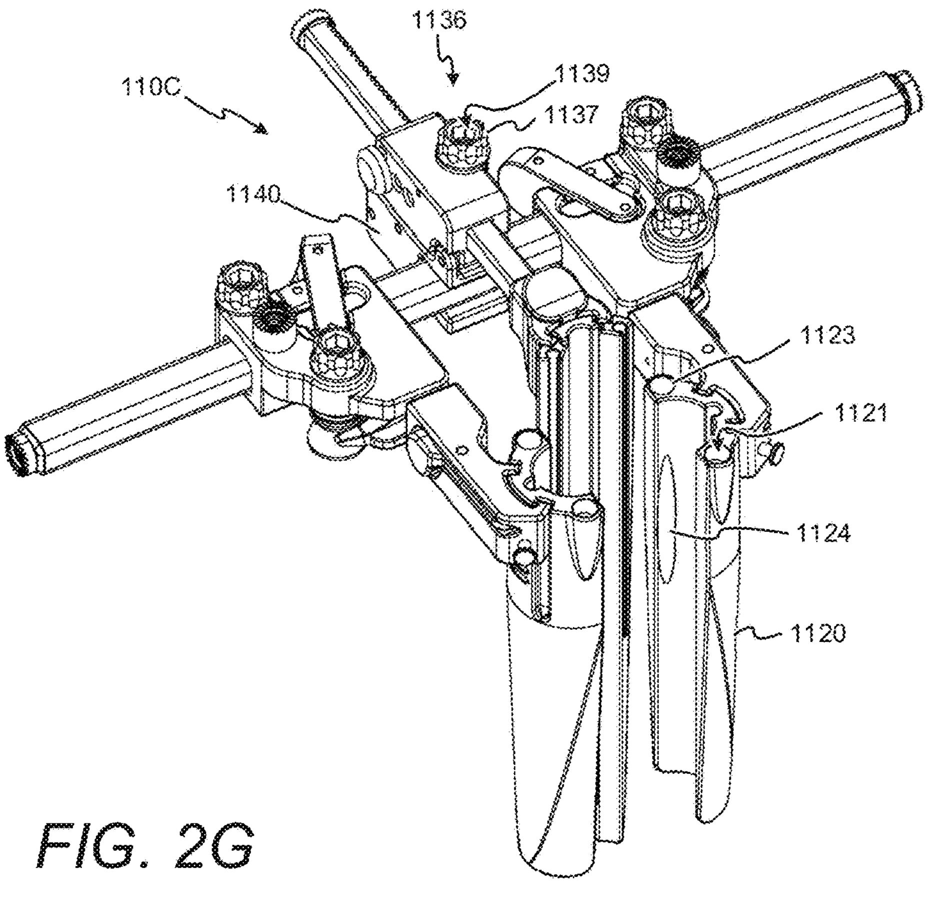
Figure 2H:
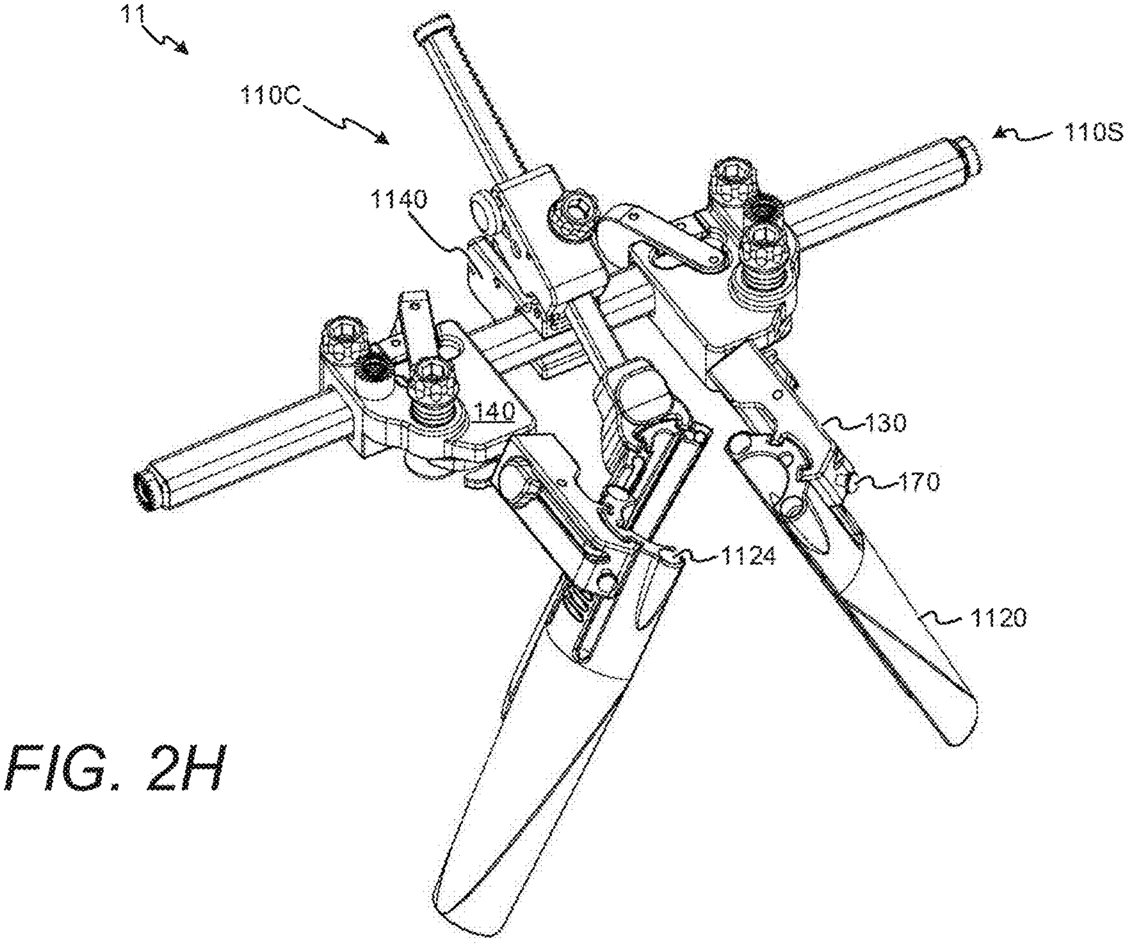
Figure 2I:
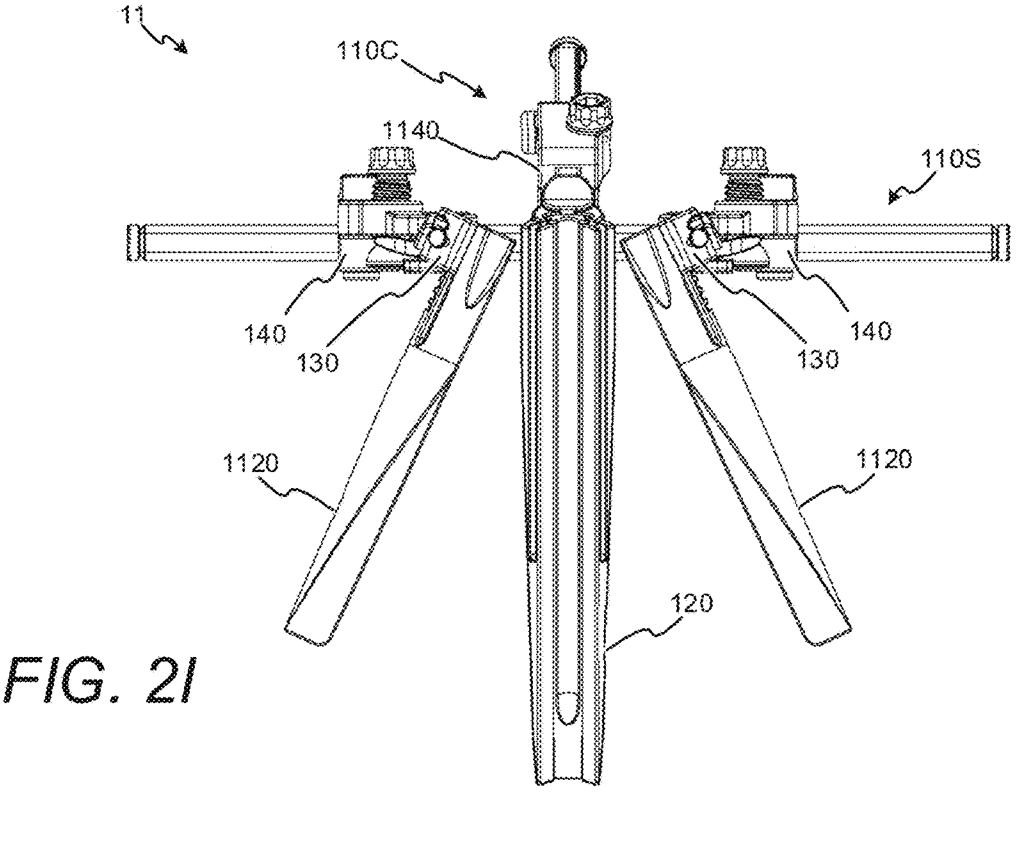
Figure 2K:
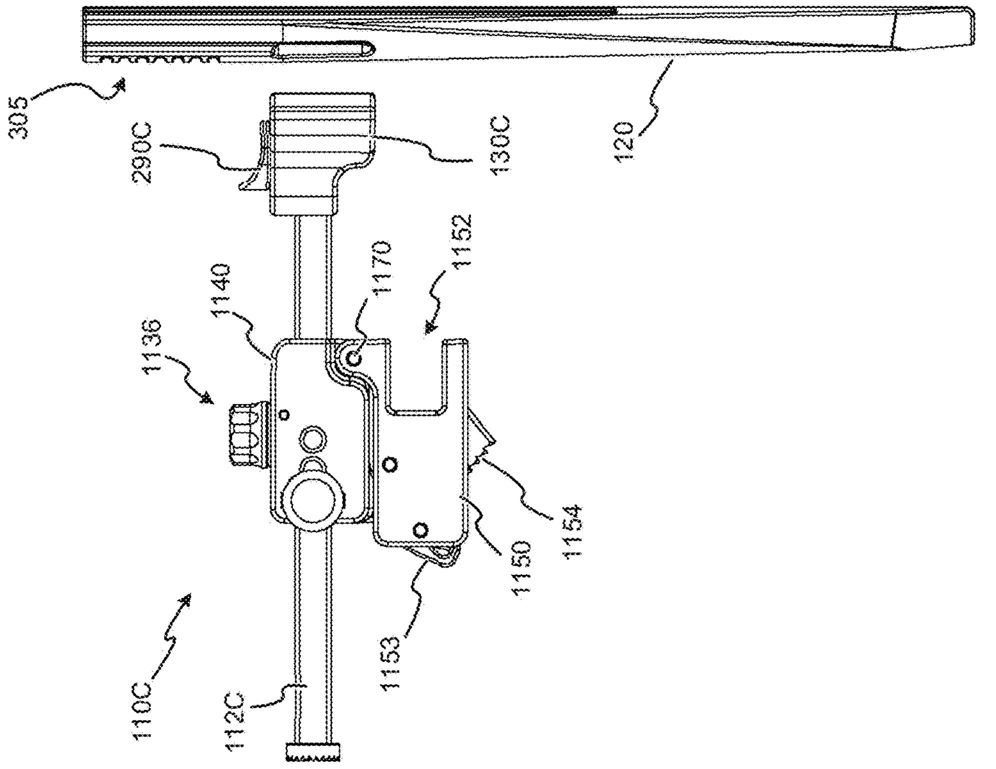
Figure 2J:
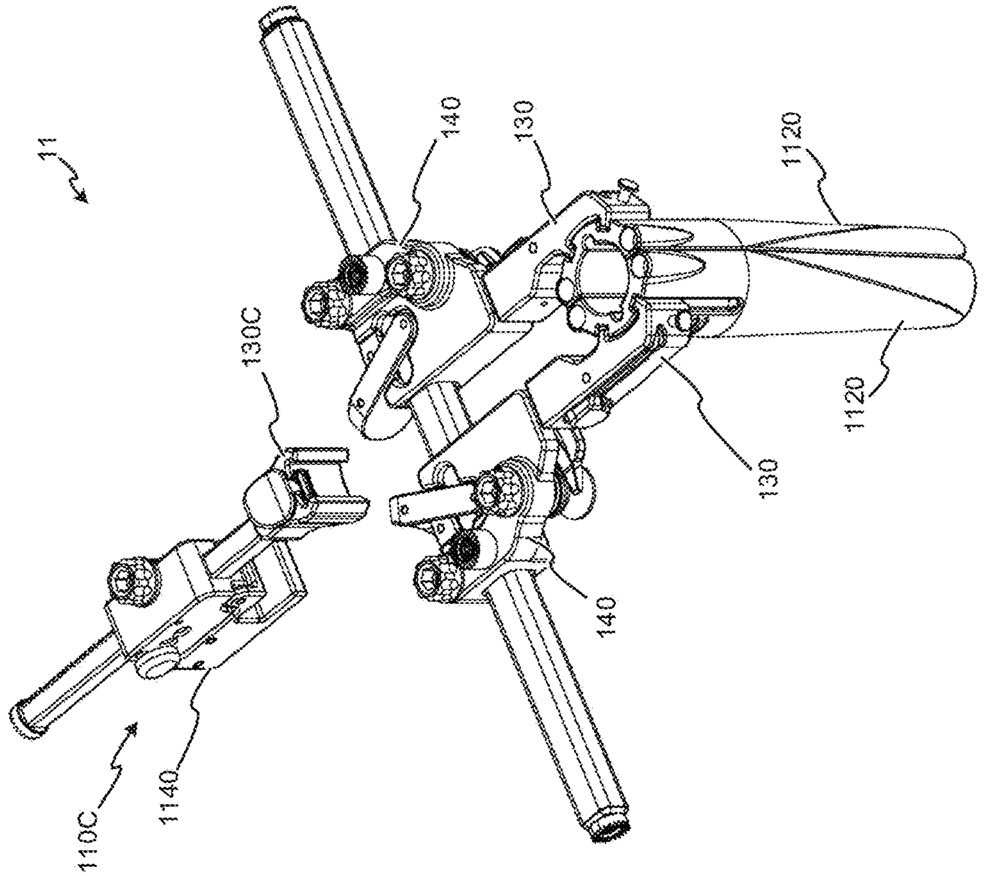
Figure 2M:
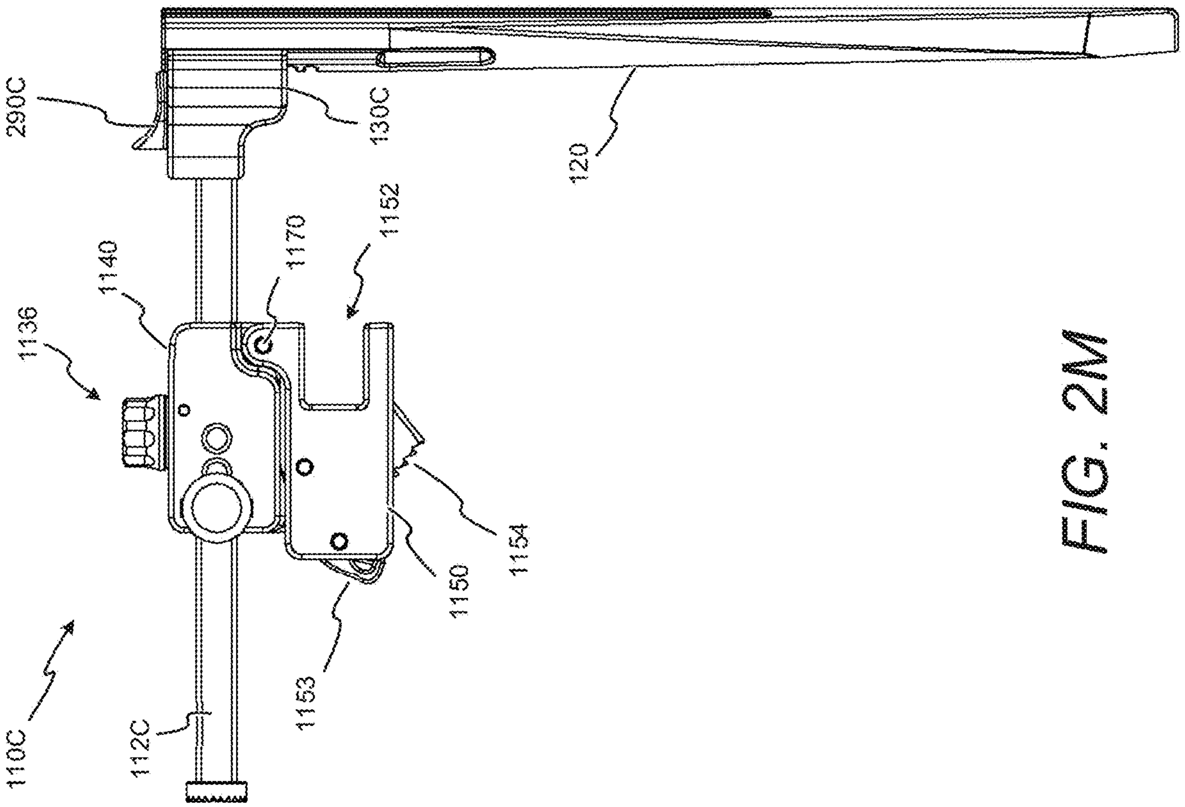
Figure 2L:
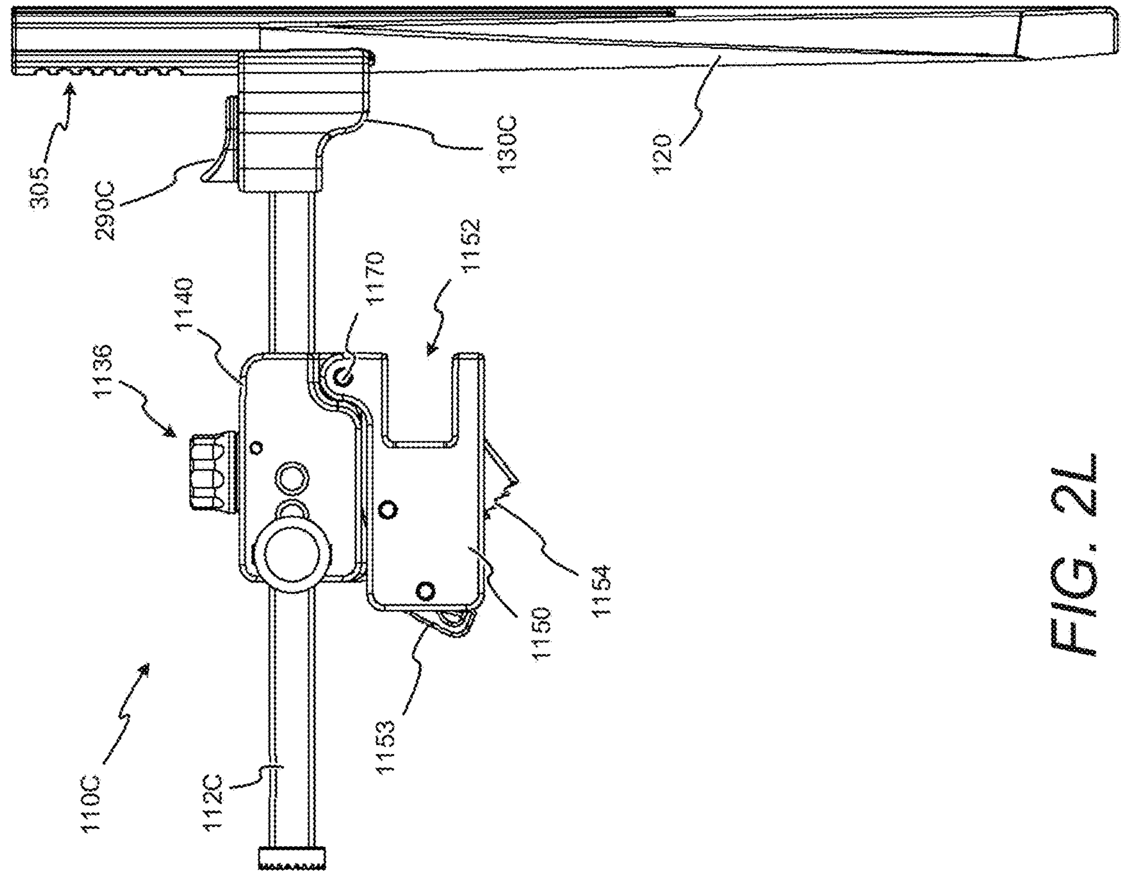
Figure 2P:
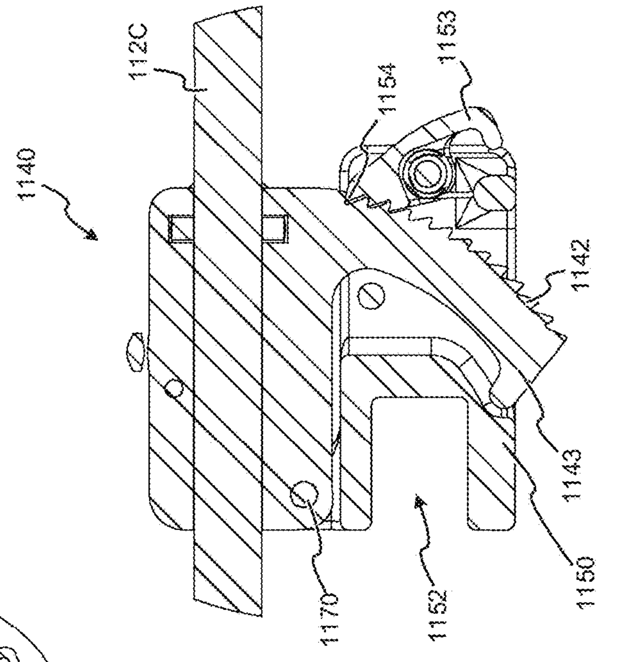
Figure 2O:
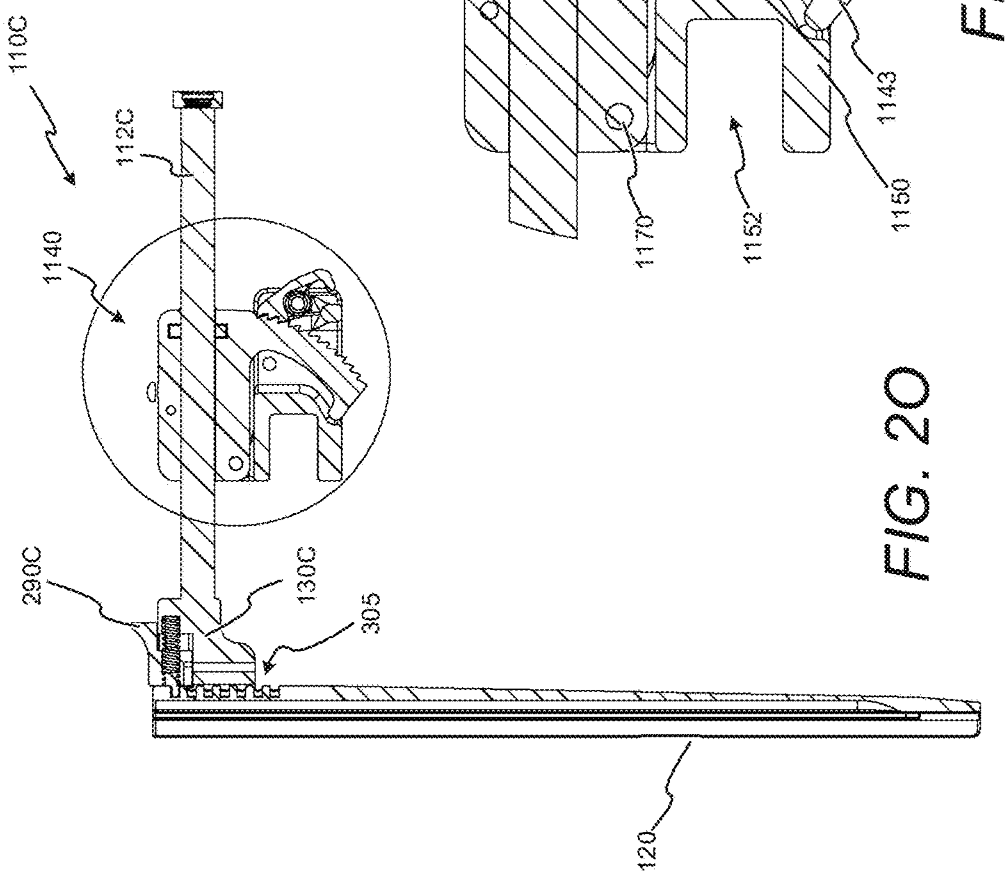
Figure 2N:
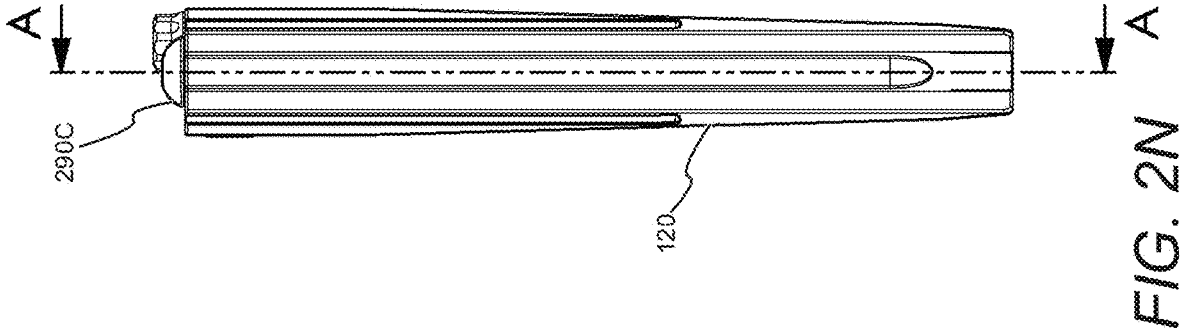
Figure 2R:
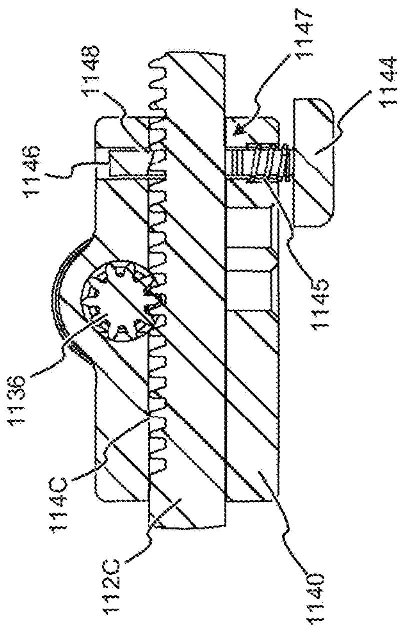
Figure 2S:
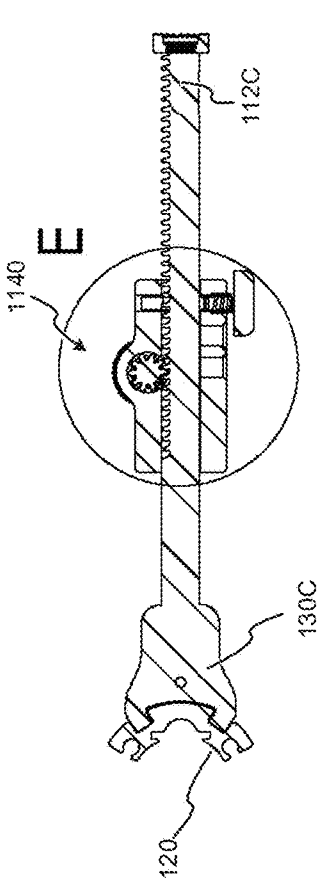
Figure 2Q:
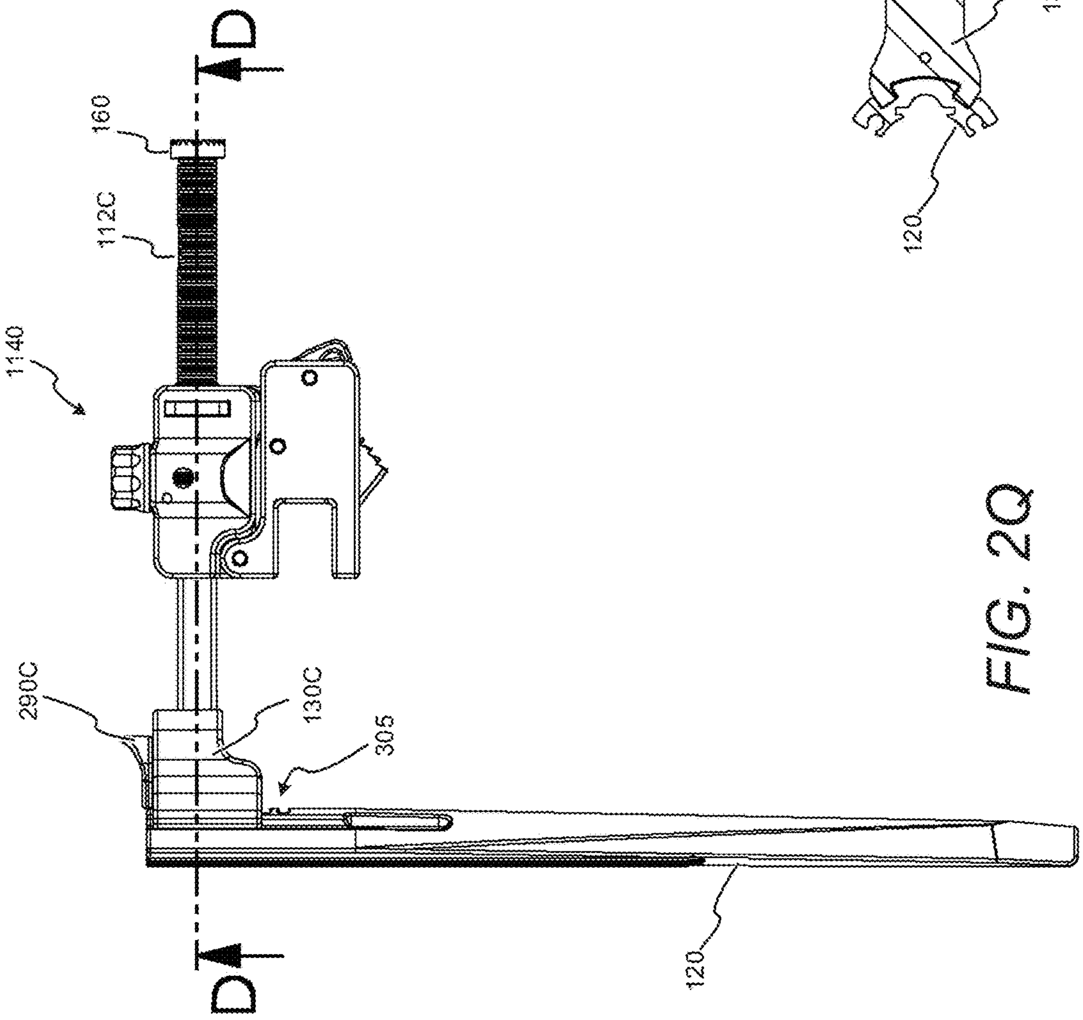
Figure 3A:
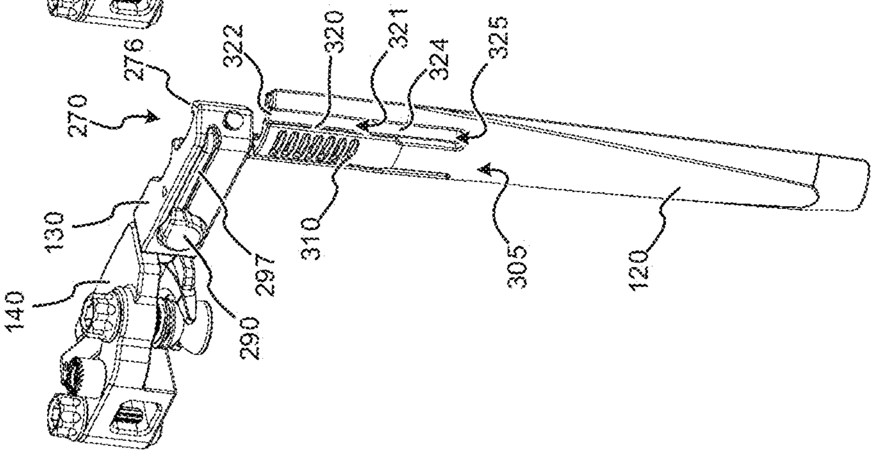
FIGS. 3A-3T provide various views depicting interactions between retractor arms of the retractor system and retractor blade tracks of the retractor blades.
Figure 3B:
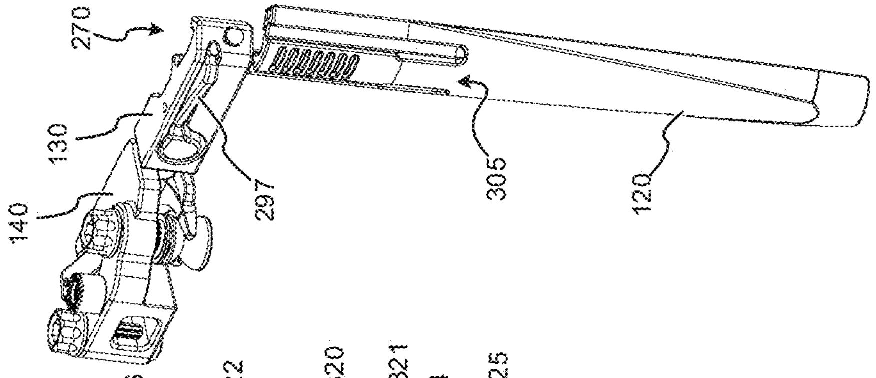
Figure 3C:
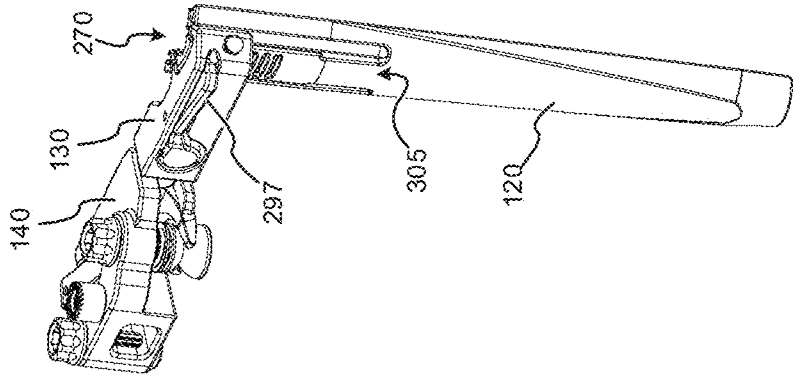
Figure 3D:
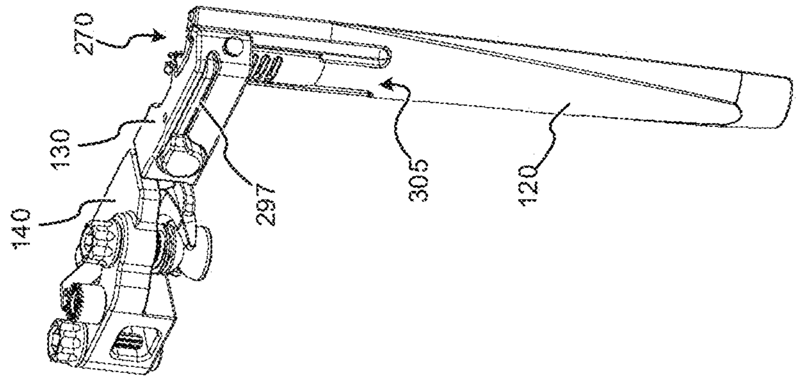
Figure 3H:
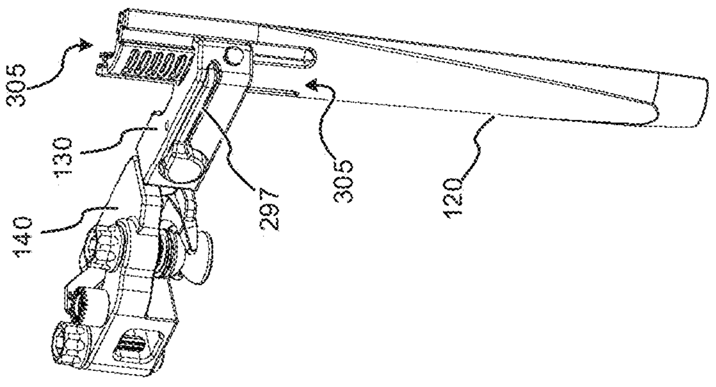
Figure 3G:
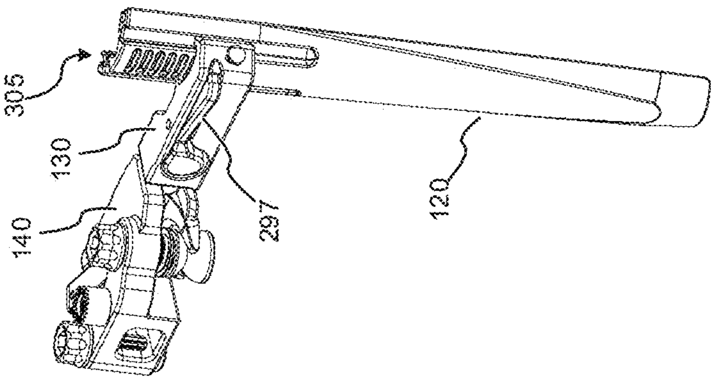
Figure 3F:
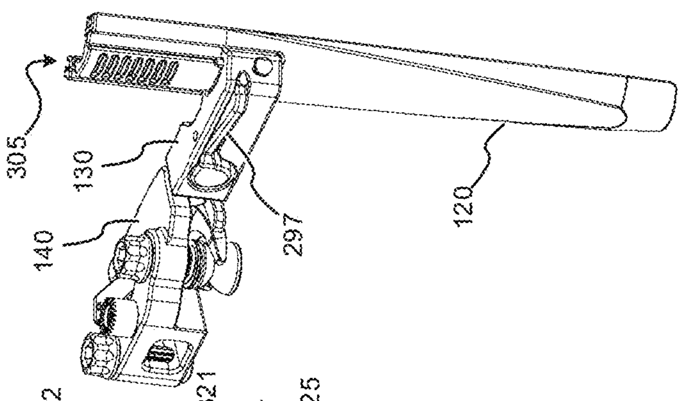
Figure 3E:
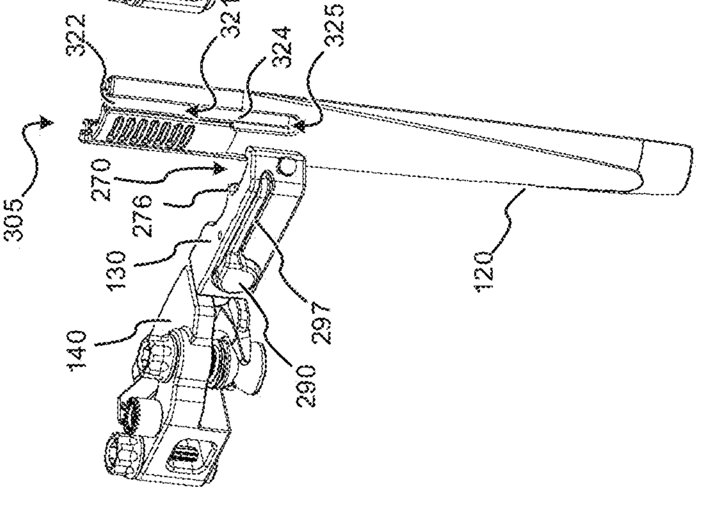
Figure 3I:
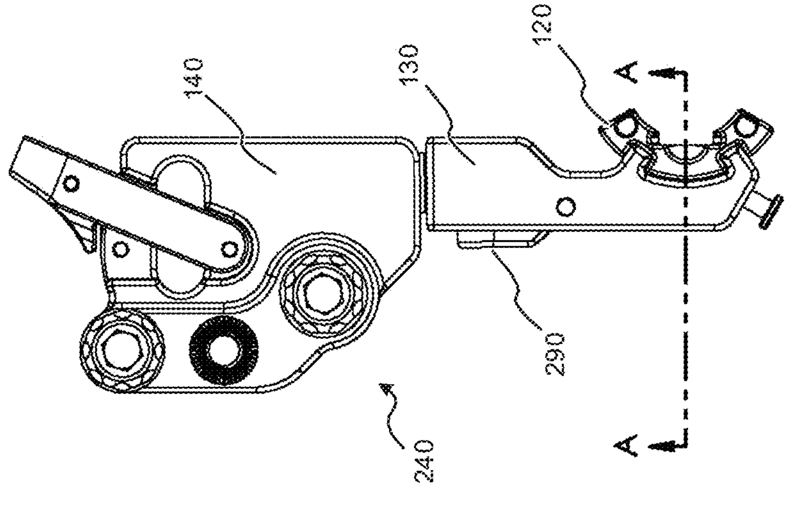
Figure 3J:
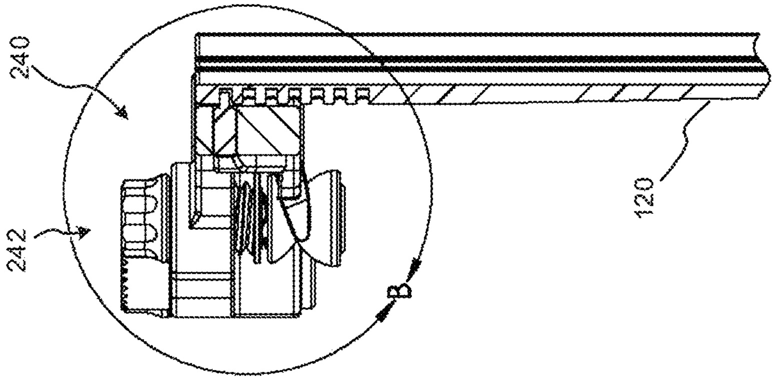
Figure 3K:
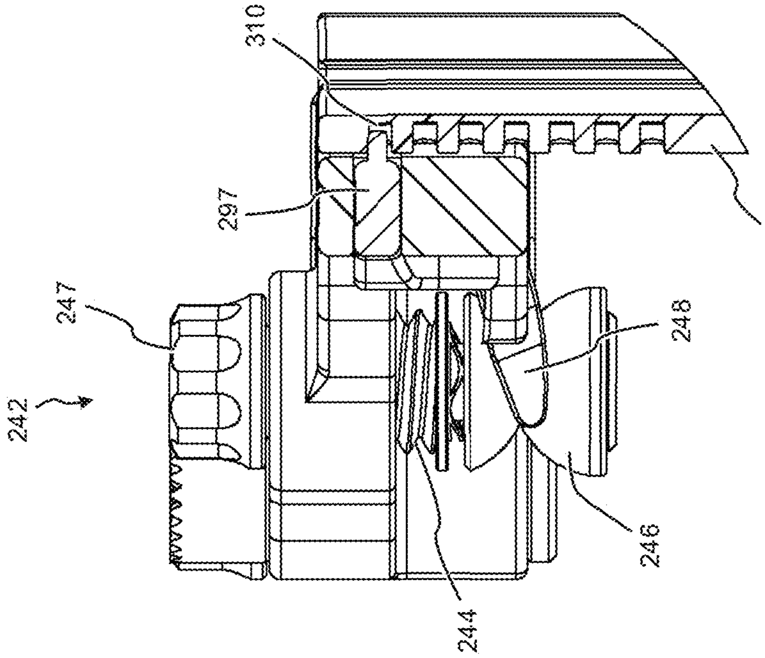
Figure 3L:
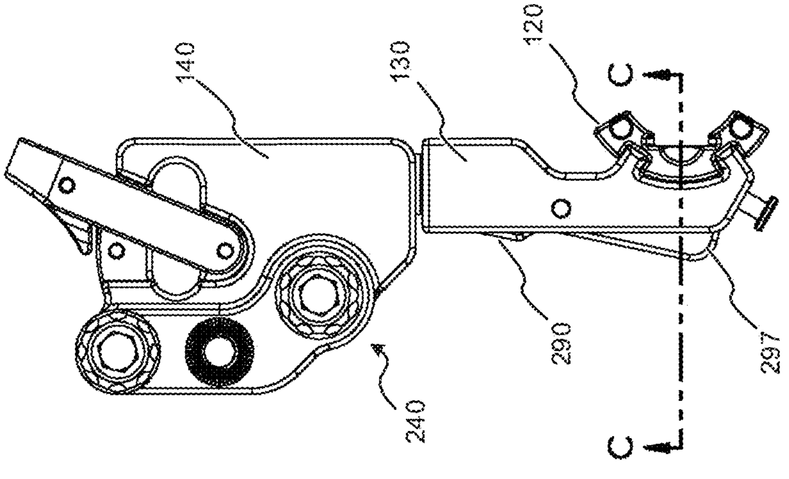
Figure 3M:
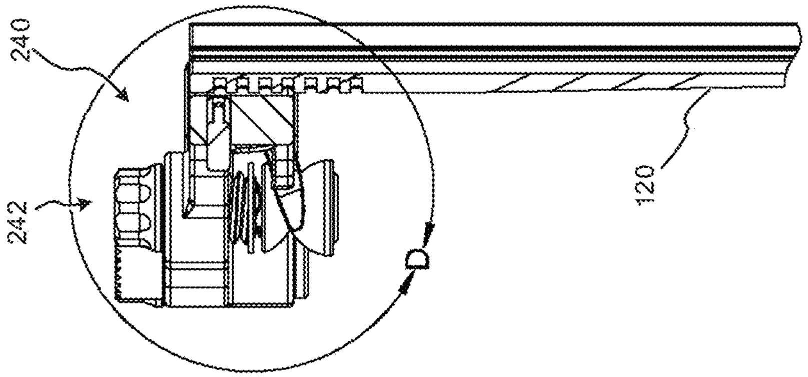
Figure 3N:
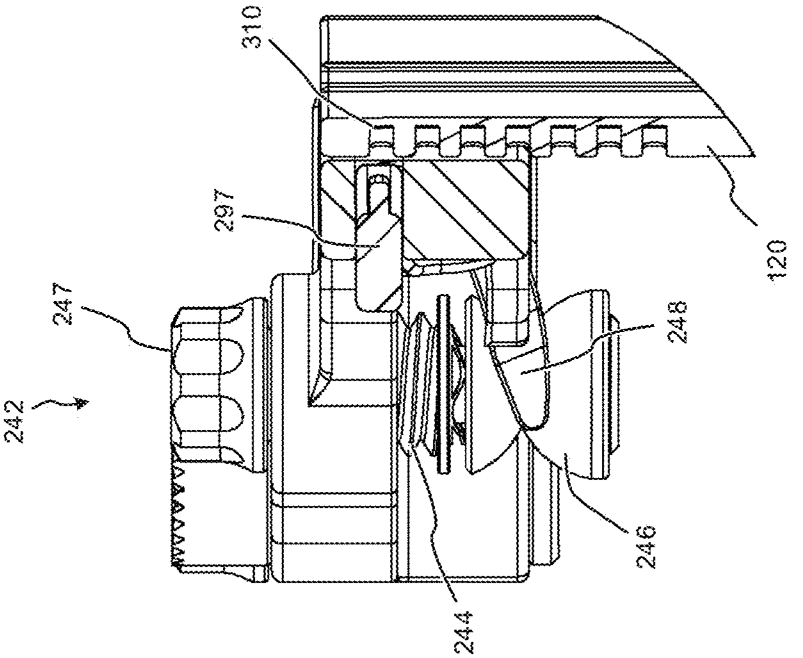
Figure 3O:
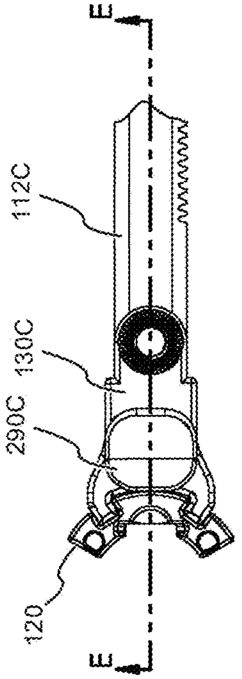
Figure 3Q:
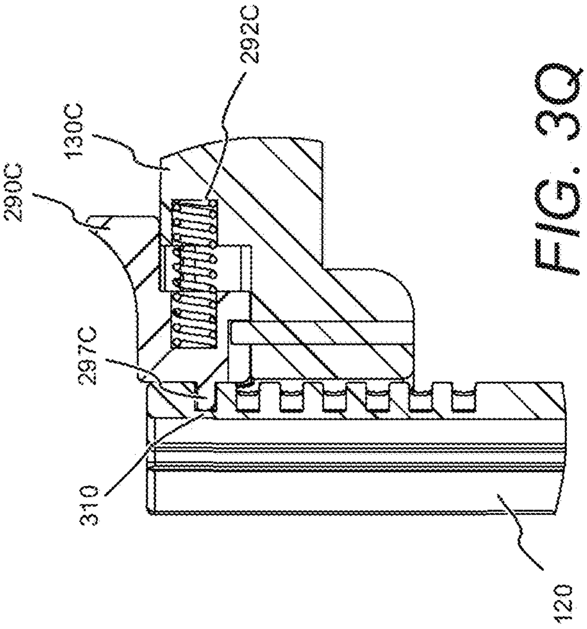
Figure 3P:
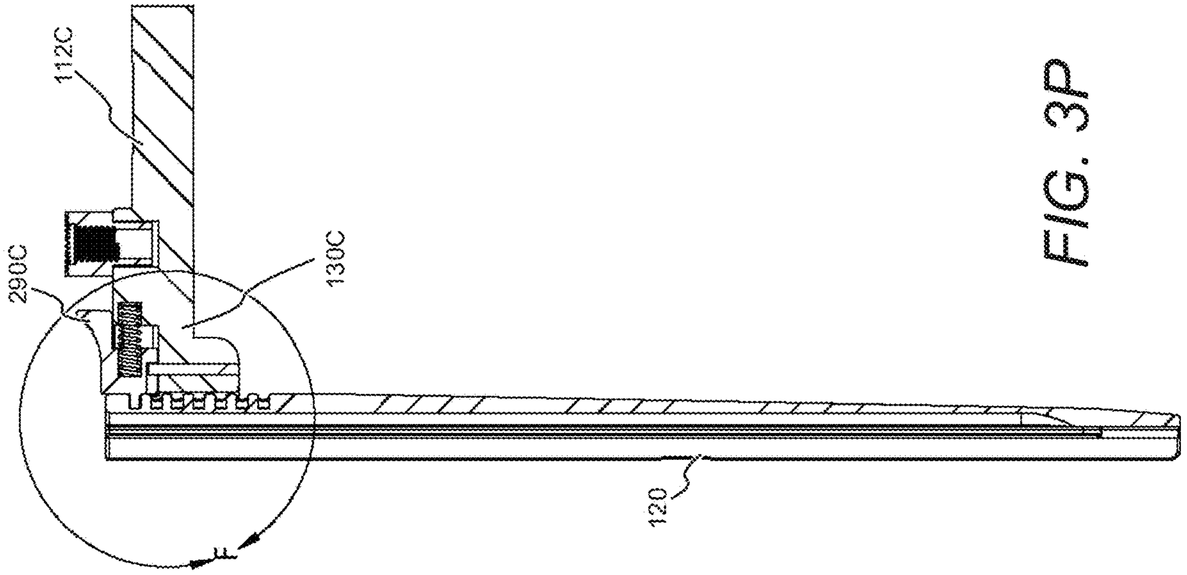
Figure 3R:
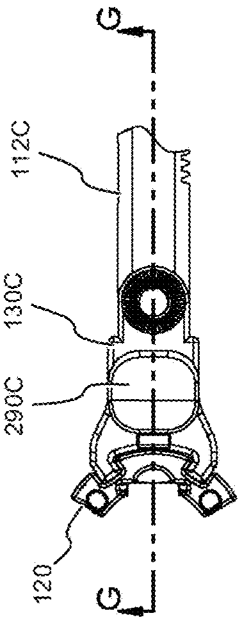
Figure 3T:
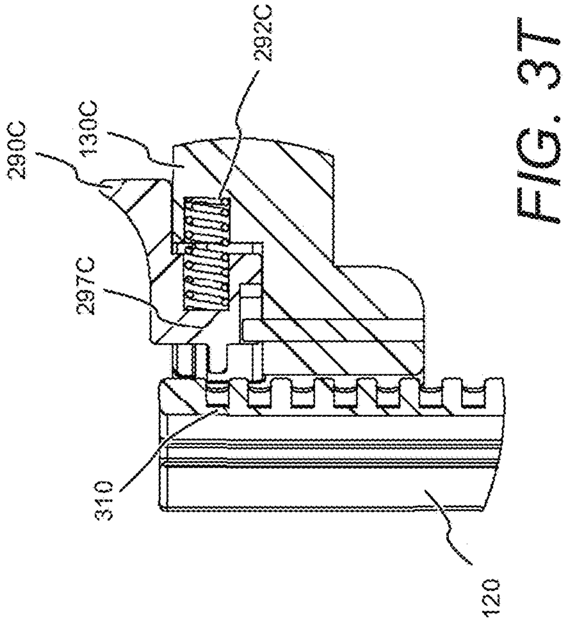
Figure 3S:
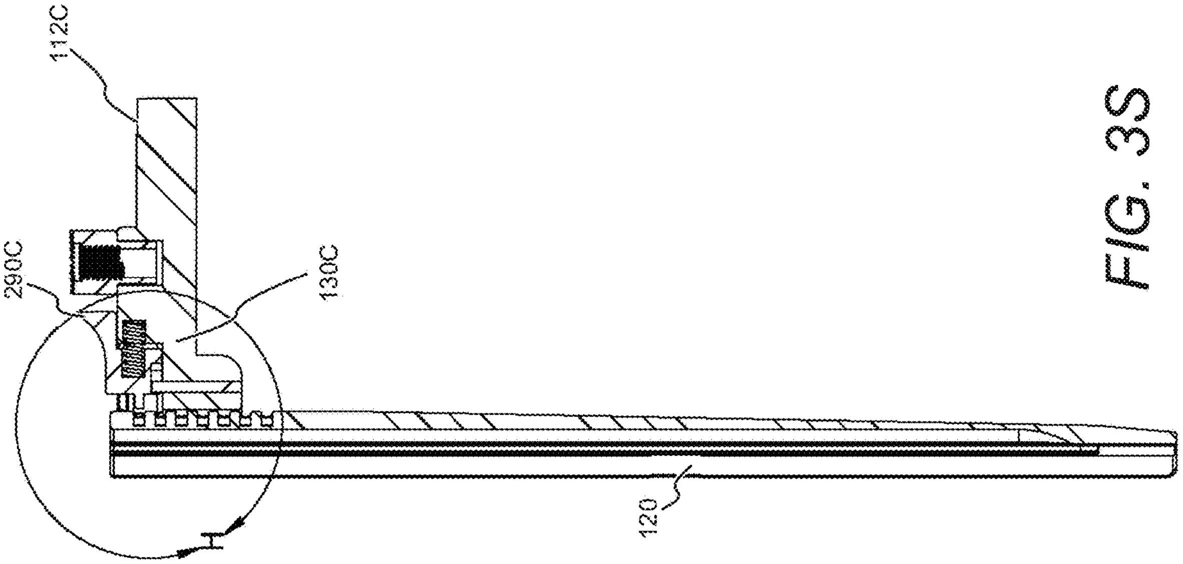
Figure 4C:
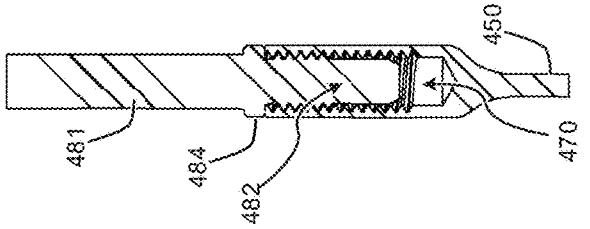
FIGS. 4A-4K provide various views depicting a intradiscal shim, its attachment to a retractor blade of FIGS. 1A-1M, and a tool for attaching the intradiscal shim.
Figure 4B:
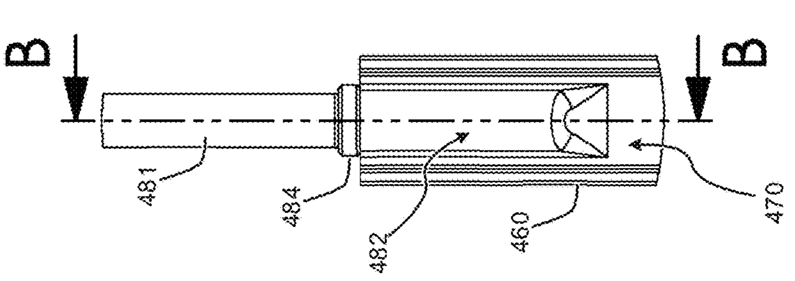
Figure 4A:
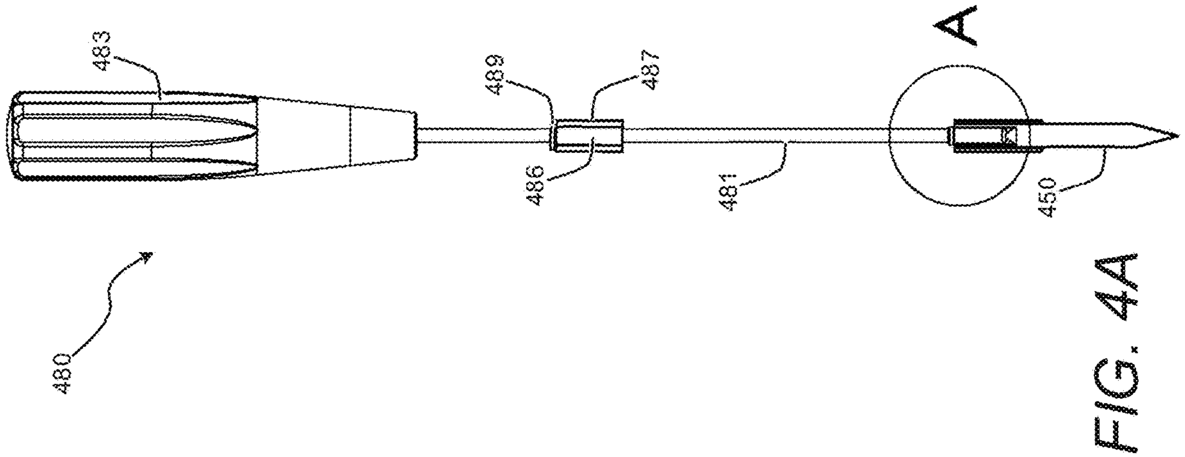
Figure 4D:
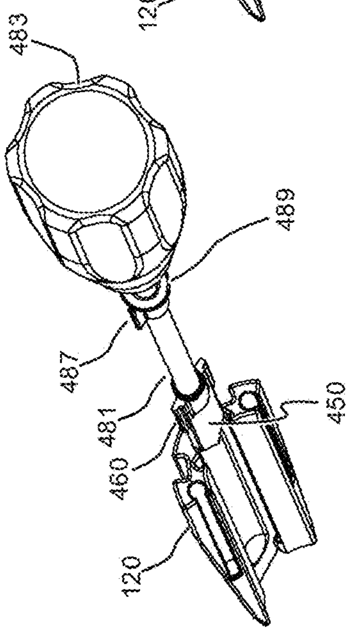
Figure 4E:
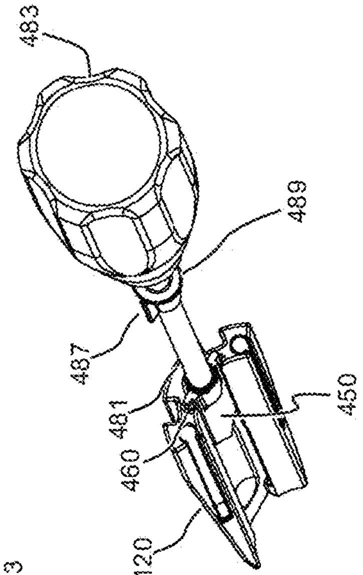
Figure 4F:
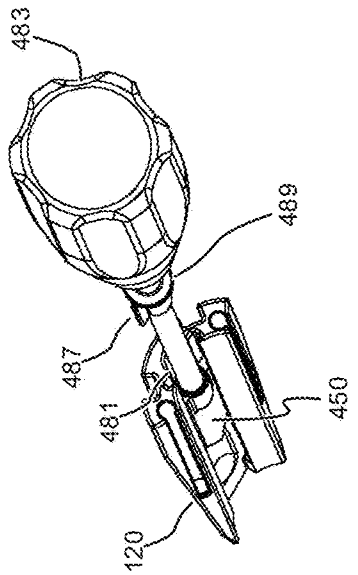
Figure 4G:
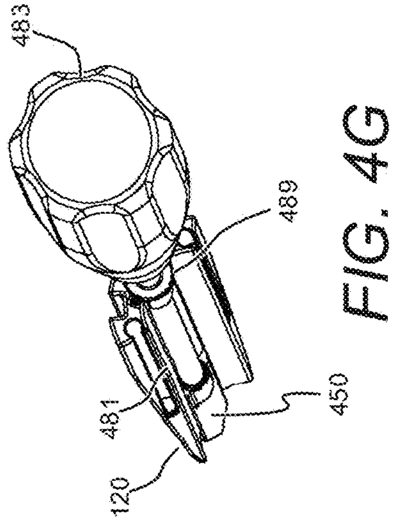
Figure 4H:
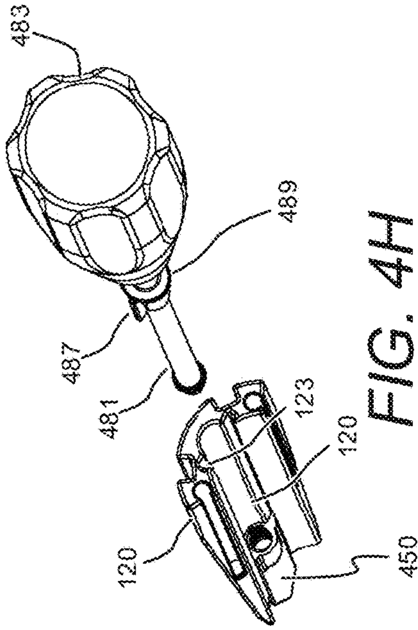
Figure 4K:
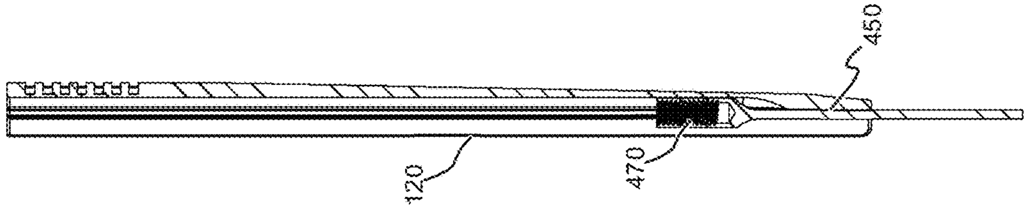
Figure 4J:
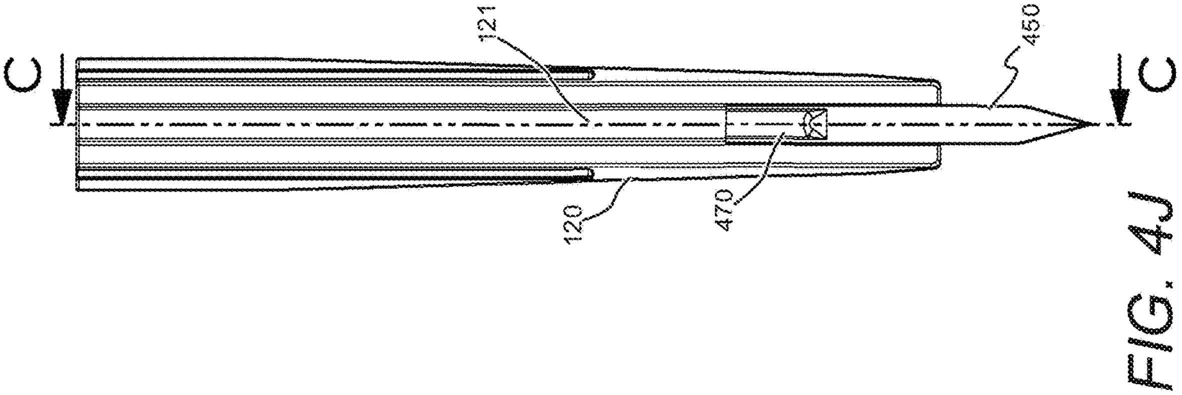
Figure 4I:
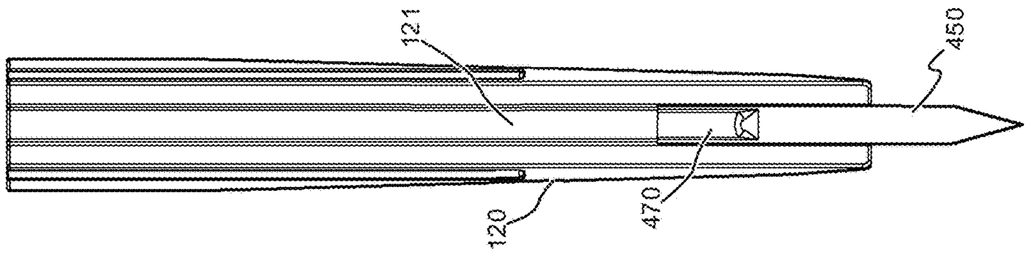

Referring now to FIGS. 2A-2S, an embodiment of a retractor system 11 is shown. As depicted, the retractor system 11 may include a single straight rack 110S to which both outer carriages 140 are coupled. The retractor system 11 may further include outer retractor arms 130 which attach retractor blades 1120 to respective outer carriages 140. In various embodiments, the outer retractor arms 130 and outer carriages 140 of the retractor system 11 may be implemented in the same manner as the outer retractor arms 130 and outer carriages 140 of the retractor system 10 shown in FIGS. 1A-1M. The retractor blades 1120, like the retractor blades 120, may each include a retractor blade track 305 along a back side of the retractor blade 1120. Similarly, retractor arm channels 270 in the outer retractor arms 130 may engage and traverse the retractor blade tracks 305 of the retractor blades 1120 in the same manner as the outer retractor arms 130 of the retractor system 10 engage and traverse the retractor blade tracks 305 of the retractor blades 120.

However, the retractor blades 1120 may have a different geometry than the retractor blades 120. In particular, the two retractor blades 1120 of retractor system 11 may be sized to form a circular cylinder when brought together as shown in FIG. 2A. The retractor system 10 of FIGS. 1A-1M, however, utilizes three retractor blades 120 to form a circular cylinder when brought together. Further, the retractor blades 1120 may lack the fin channels 122, which the retractor blades 120 use to attach blade fins. The retractor blades 1120 may also lack the retractor blade channel 121, which the retractor blades 120 use to attach an intradiscal shim 450 or the retractor blade handle 1000, 1001 of FIGS. 12A-13B. However, in some embodiments, the retractor blades 1120 may be modified to include similar fin channels 122 to permit attachment of blade fins and/or a retractor blade channel 121 to permit the attachment of an intradiscal shim 450 or retractor blade handle 1000, 1001.

Instead of or in addition to the above-noted channels 121, 122, the retractor blades 1120 may include accessory channels 1121 along the outer lateral edges for the receipt and/or attachment of accessories. Each accessory channel 1121 may include a channel upper opening 1123 toward a proximal end of the retractor blade 1120 and may extend to a channel lower opening 1124 in a front surface of the retractor blades 1120. See, e.g., FIG. 2G. Such accessory channels 1121 may permit the attachment of accessories such as lights used to illuminate the surgical site.

As shown in FIGS. 2G-2S, the retractor system 11 may further include a central rack 110C which is detachably coupled to the straight rack 110S via a central carriage 1140. The retractor system 11 also includes a central retractor arm 130C which attaches a retractor blade 120 to the central rack 110C. In various embodiments, the central rack 110C, the retractor blade 120, and the central retractor arm 130C of the retractor system 11 may be implemented in the same manner as the central rack 110C, the retractor blade 120, and the central retractor arm 130C of the retractor system 10.

Similar to the carriages 140, 140C, the central carriage 1140 may include a pinion 1136 having a head 1137 and teeth that engage the rack teeth 114C of the central rack 110C. The head 1137 may include a socket 1139 to receive a tool, which may rotate the pinion 1136. Through rotation of the pinion 1136 and its engagement with rack teeth 114C, the pinion 1136 may impart ratcheted-movement of the central carriage 1140 with respect to the central rack 110C.

However, unlike the carriages 140, 140C, the central carriage 1140 may be pivotally coupled to an attachment base 1150. The attachment base 1150 may include an attachment base channel 1152 that passes through the lateral sides of the attachment base 1150. Moreover, the back side of the attachment base channel 1152 may be closed whereas the front side of the attachment base channel 1152 may open to the front side of the attachment base 1150. The attachment base channel 1152 may be sized to closely mate with the rack 110S when the rack 110S is received by the attachment base channel 1152.

As further shown, a front lower portion of the central carriage 1140 is attached to a front upper portion of the attachment base 1150 via a pivot joint 1170. In particular, the pivot joint 1170 may include one or more pivot pins that pass through openings in the lateral sides of the central carriage 1140 and the attachment base 1150, thereby forming a pivot axis that passes through the lateral sides of the central carriage 1140 and the attachment base 1150. As a result, the central carriage 1140 may be tilted or angled with regard to the attachment base 1150 and the central rack 110C.

Furthermore, the central carriage 1140 may include a pinion body 1143 that extends from the lower surface of the central carriage 1140 and into the attachment base 1150. The attachment base 1150 may further include a button 1153 at a proximal end of a pawl 1154. The button 1153 and pawl 1154 may be spring-biased such that a distal end of the pawl 1154 is biased toward and engages rack teeth 1142 of the pinion body 1143. The distal end of the pawl 1154 and/or rack teeth 1142 of the pinion body 1143 may be angled such that the central carriage 1140 may pivot in a first direction in which the rear of the central carriage 1140 moves away from the attachment base 1150 without first disengaging the distal end of the pawl 1154 by, for example, pressing the button 1153. Conversely, the distal end of the pawl 1154 and/or the rack teeth 1142 of the pinion body 1143 may be angled such that the central carriage 1140 is prevented from pivoting in a second direction opposite the first direction without first disengaging the distal end of the pawl 1154 from the rack teeth 1142 by, for example, pressing the button 1153.

Furthermore, as shown in FIGS. 2R and 2S, the central carriage 1140 may include a button 1144 and a spring 1145 that biases the button 1144 away from the central carriage 1140. The button 1144 may include a member 1146 that extends perpendicular to an outer surface of the button 1144. The member 1146 may include an opening 1147 through which the central rack 110C passes. Moreover, the distal inner surface of the opening 1147 may include a pawl 1148. When biased away from the central carriage 1140, a distal end of the pawl 1148 may engage one or more rack teeth 114C of the central rack 110C. In one embodiment, the distal end of the pawl 1148 and/or the rack teeth 114C are angled such that, when the distal end of the pawl 1148 is engaged with the rack teeth 114C, rotation of the pinion 1136 may move the central rack 110C with respect to the central carriage 1140 in a first direction but is unable to move the central rack 110C in a second direction opposite the first direction. Thus, in order to move the central rack 110C in the second direction via rotation of the pinion 1136, a person may first press the button 1144 to disengage the distal end of the pawl 1148 from the rack teeth 114C and permit movement in the second direction.

Figure 11B:
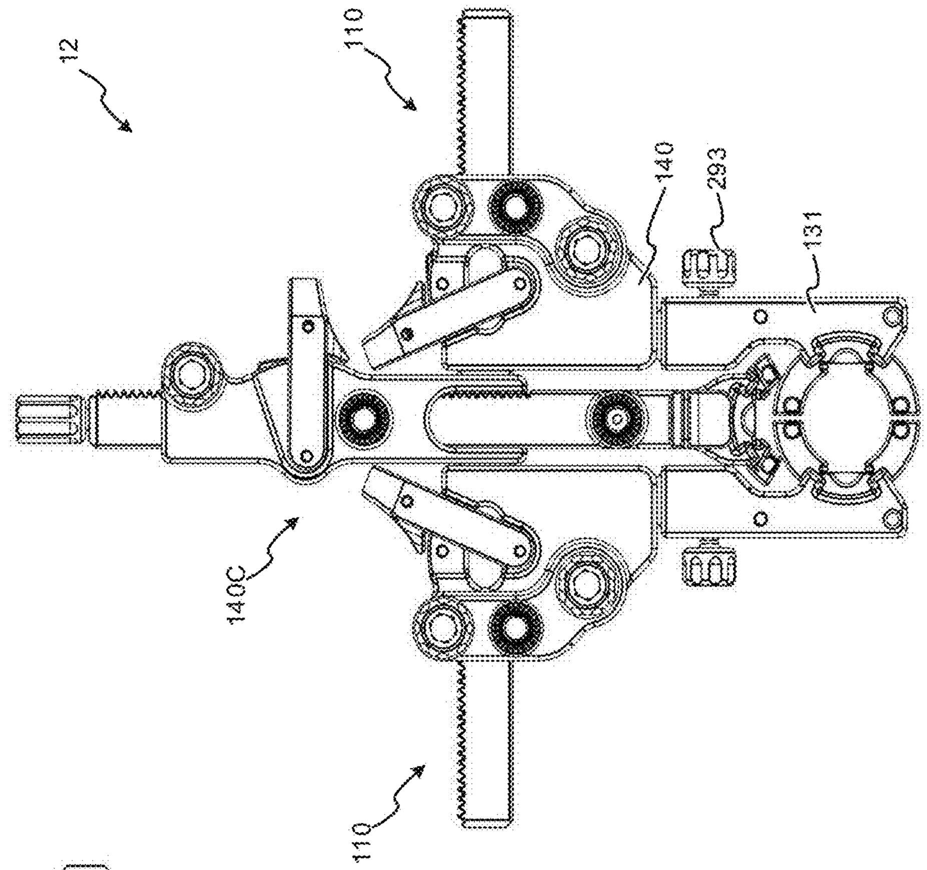
FIGS. 11A-11D provide various views of a retractor system in accordance with aspects of the present disclosure.
Figure 11A:
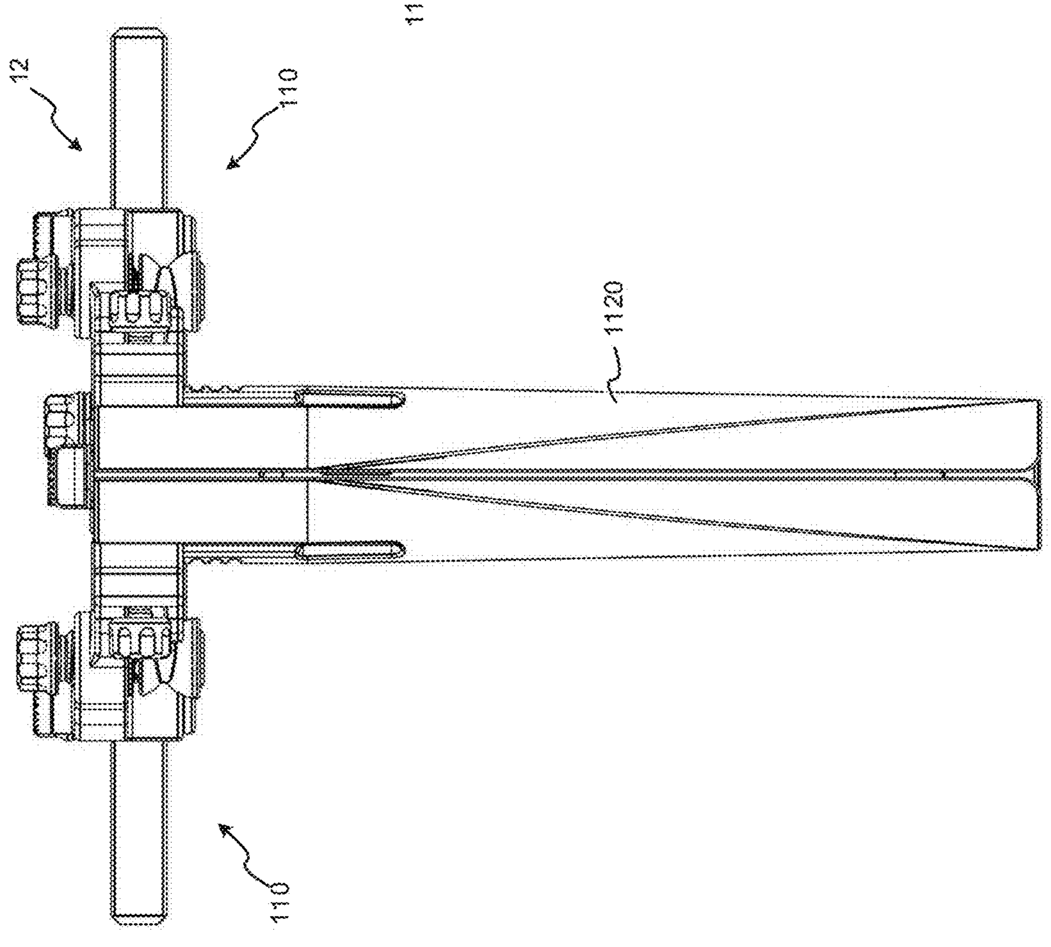
Figure 11D:
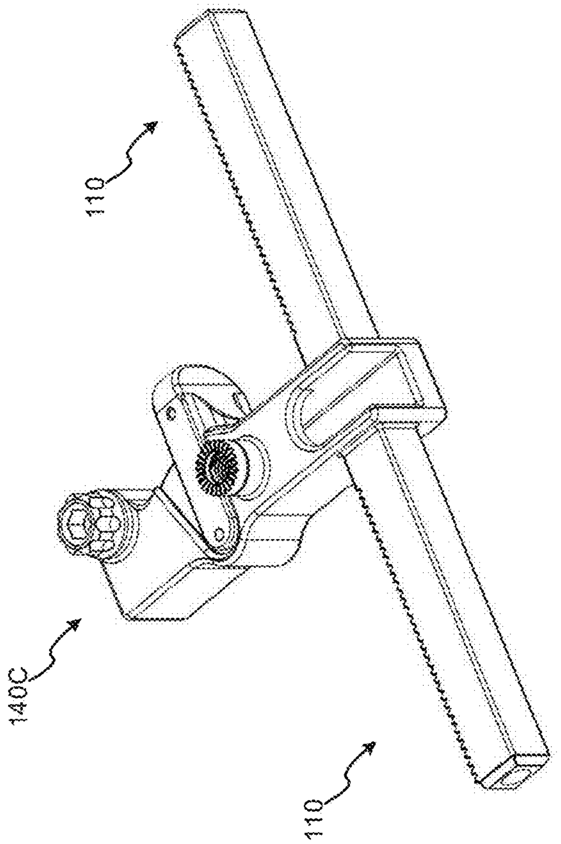
Figure 11C:
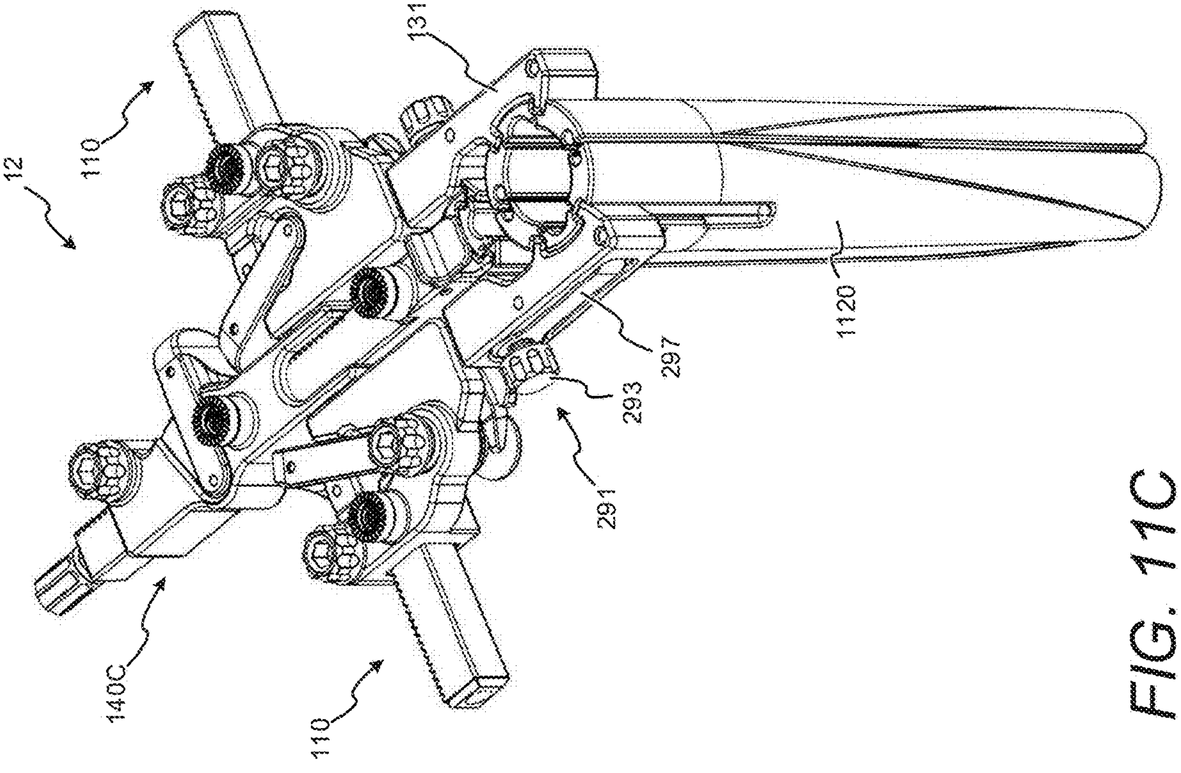

Referring now to FIGS. 11A-11B, an embodiment of a retractor system 12 is shown. As depicted, the retractor system 12 may be implemented similar to the retractor system 10 of FIGS. 1A-1M. However, as shown, proximal ends of outer racks 110 are affixed to lateral sides of the central carriage 140C such that the outer racks 110 extend from the central carriage 140C and form an internal angle $\alpha$ of 180° with respect to each other. See, e.g., FIG. 9. As such, the outer racks 110 of the rack assembly 100 may essentially provide a straight rack similar to the straight rack 110S of the retractor system 11.

Moreover, the retractor system 12 may include the retractor blades 1120 of the retractor system 11 which have a different geometry than the retractor blades 120. Namely, the two retractor blades 1120 of retractor system 12 may be sized to form a circular cylinder when brought together as shown in FIG. 11B.

As shown, the retractor system 12 may comprise outer retractor arms 131 which may be implemented in a manner similar to the retractor arms 130 of the retractor systems 10, 11. However, the outer retractor arms 131 replace the blade release button 290 of the outer retractor arms 130 with a retaining screw 291 at a proximal end of the pawl 297. The retaining screw 291 may operate in a similar manner to the blade release button 290. Namely, a person may press a head 293 of the retaining screw 291 to overcome a biasing force applied by a spring (not shown) and pivot the pawl 297 about the pivot pin 292 and the distal end of the pawl 297 toward a fully disengaged position. In the fully disengaged position, the distal end of the pawl 297 may disengage a track catch 310 (e.g., hole, slot, depression, recess, tooth, etc.) of the retractor blade 1120 so as to permit sliding the retractor blade 1120 along the retractor arm channel 270. Conversely, a person may cease pressing the head 293 of the retaining screw to a spring bias to pivot the pawl 297 about the pivot pin 292 and the distal end of the pawl toward a fully engaged position. In the fully engaged position, the distal end of the pawl 297 may extend from a distal end of the outer retractor arm 130 and into the retractor arm channel 270. In such an engaged position, the distal end of the pawl 297 may engage a track catch 310 of the retractor blade 1120 and retain the retractor blade 120 at a specific position along the retractor blade track 305.

However, unlike the blade release button 290, a person may rotate the retaining screw 291 via head 293 in a first or tightening direction. Such rotation may draw the retaining screw 291 into the proximal end of the pawl 297 and more specifically the head 293 of the retaining screw 291 toward a surface of the retractor arm 130. The person may continue to tighten the retaining screw 291 until the head 293 abuts or come into close engagement with a surface of the retractor arm 130. In such position, the head 293 may prevent a person from pressing the proximal end of the pawl 297 sufficiently into the retractor arm 130 to disengage the distal end of the pawl 297 from a track catch 310. Thus, by tightening the retaining screw 291, a person may effectively lock the retractor arm 130 to a specific location along the retractor blade 1120. Conversely, a person may rotate the retaining screw via the head 293 in a second or untightening direction to withdraw the head 293 from the surface of the retractor arm 130. When sufficient withdrawn, a person may again press the head 293 to disengage a distal end of the pawl 297 from a track catch 310.

Figure 12B:
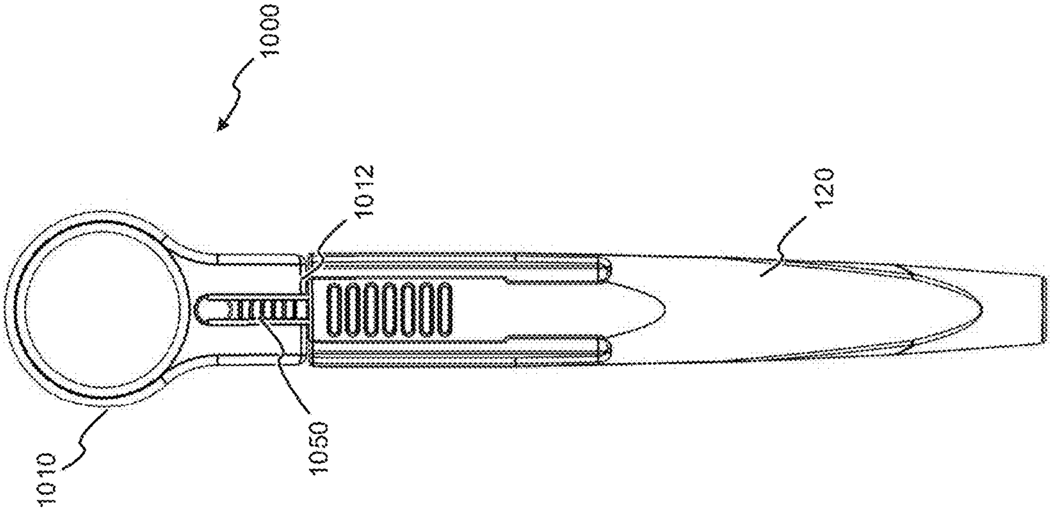
FIGS. 12A-12B provide various views for a retractor handle and its attachment to a retractor blade of FIGS. 1A-1M.
Figure 12A:
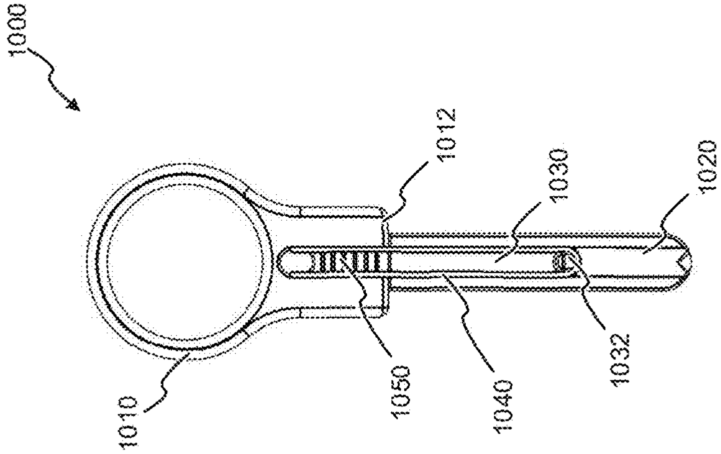

Referring now to FIGS. 12A-12B, an embodiment of a retractor blade handle 1000 is shown. As shown, the retractor blade handle 1000 may include a handle grip 1010 and a handle shaft 1020 that extends from the handle grip 1010. In particular, a proximal end of the handle shaft 1020 may be coupled to the handle grip 1010 such that the handle shaft 1020 extends longitudinally away from the handle grip 1010 and a handle shoulder 1012 extends laterally beyond the handle shaft 1020.

A distal end of the handle shaft 1020 may be rounded or tapered to ease insertion of the handle shaft 1020 into a retractor blade channel 121 of a retractor blade 120, 1120. To this end, the handle shaft 1020 may be shaped to engage the retractor blade channel 121 in a manner similar to the intradiscal shim 450. In particular, the handle shaft 1020 may include shaft flanges 1030 that traverse longitudinal edges of the handle shaft 1020 similar to how the shim flanges 460 traverse longitudinal edges of the intradiscal shim 450. A proximal edge of each shaft flange 1030 may be attached to a respective longitudinal edge of the handle shaft 1020. As such, a distal end of each shaft flange 1030 may protrude from the longitudinal edge of the handle shaft 1020. Moreover, the distal end of each shaft flange 1030 may be sized to closely mate with a respective channel recess 123 when inserted into the retractor blade channel 121.

Moreover, the retractor blade handle 1000 may include a leaf spring 1030 that extends longitudinal along the handle shaft 1020. In particular, the leaf spring 1030 may be positioned in a longitudinal slot 1040 that spans the hand grip 1010 and the handle shaft 1020. A proximal end of the leaf spring 1030 may be coupled to the handle grip 1010 at an upper end of the longitudinal slot 1040. A distal end may extend toward but remain freely detached from a lower end of the longitudinal slot 1040. Moreover, the distal end of the leaf spring 1030 may comprise a knob or detent 1032 that protrudes from the longitudinal slot 1040. The detent 1032 may engage a front side of the retractor blade 120, 1120 when the handle shaft 1020 is slid into or otherwise received by the retractor blade channel 121. In particular, the detent

1032 may deflect the leaf spring 1030 such that the detent 1032 retracts into the longitudinal slot 1040.

However, when the handle shoulder 1012 is fully seated against a proximal end of the retractor blade 120, 1120 as shown in FIG. 12B, the leaf spring 1030 may force the detent 1032 outward from the longitudinal slot 1040 such that the detent 1032 engages a catch (e.g., a hole, depression, recess, tooth, etc.) in a front side of the retractor blade 120, 1120. Such engagement of the detent 1032 with the catch may prevent the handle shaft 1020 from being extracted from the retractor blade channel 121. As such, once secured to the retractor blade 120, 1120, a person may manipulate and position the retractor blade 120, 1120 via the handle grip 1010 of the retractor blade handle 1000.

As further shown, the retractor blade handle 1000 may include a handle release button 1050 toward a proximal end of the leaf spring 1030. A person may press the handle release button 1050 to deflect the leaf spring 1030 into the longitudinal slot 1040, which may cause the detent 1032 to retract into the longitudinal slot 1040 and disengage the catch of the retractor blade 120, 1120. Once disengaged, a person may slide the handle shaft 1020 out of the retractor blade channel 121 and thus detach the retractor blade handle 1000 from the retractor blade 120, 1120.

Figure 13B:
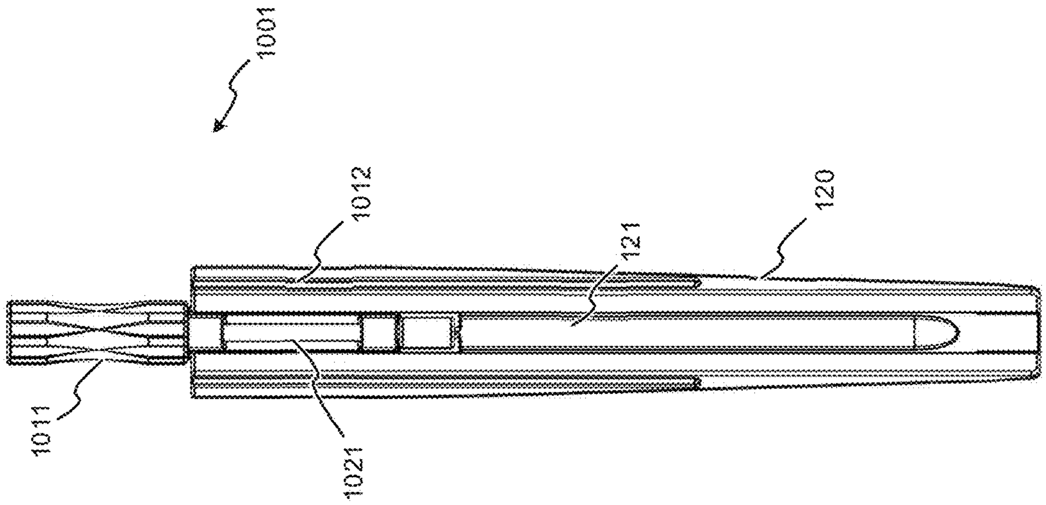
FIGS. 13A-13B provide various views for a retractor handle and its attachment to a retractor blade of FIGS. 1A-1M.
Figure 13A:
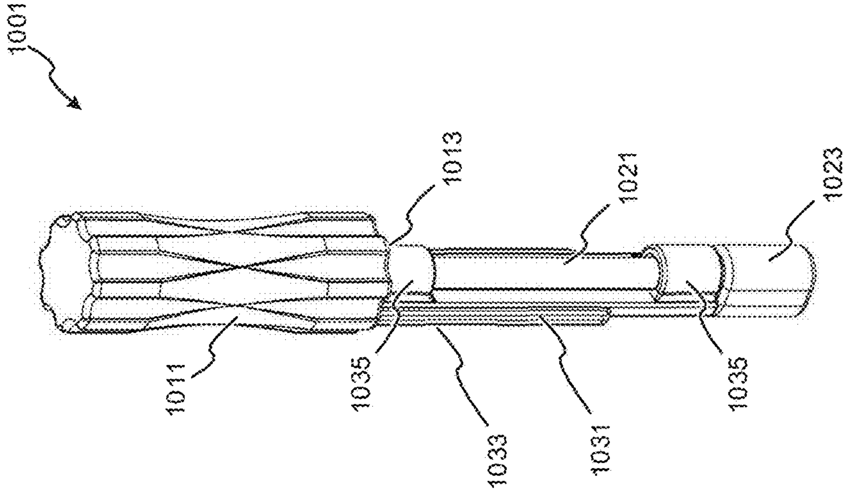

Referring now to FIGS. 13A-13B, an embodiment of a retractor blade handle 1001 is shown. As shown, the retractor blade handle 1001 may include a handle grip 1011, a handle shaft 1021, and a handle mount 1031. The handle shaft 1021 may extend from the handle grip 1011. In particular, a proximal end of the handle shaft 1021 may be coupled to the handle grip 1011 such that the handle shaft 1021 extends longitudinally away from the handle grip 1011 and the handle shoulder 1013 extend laterally beyond the handle shaft 1021. Similarly, the handle mount 1031 may extend from the handle grip 1011. In particular, a proximal end of the handle mount 1031 may be coupled to the handle shoulder 1013 such that the handle mount 1031 extends longitudinally away from the handle grip 1011 and the handle shoulder 1013.

A distal end of the handle mount 1031 may be rounded or tapered to ease insertion of the handle mount 1031 into a retractor blade channel 121 of a retractor blade 120, 1120. To this end, the handle mount 1031 may be shaped to engage the retractor blade channel 121 in a manner similar to the intradiscal shim 450. In particular, the handle mount 1031 may include handle mount flanges 1033 that traverse longitudinal edges of the handle mount 1031 similar to how the shim flanges 460 traverse longitudinal edges of the intradiscal shim 450. A proximal edge of each handle mount flange 1033 may be attached to a respective longitudinal edge of the handle mount 1031. As such, a distal end of each handle mount flange 1033 may protrude from the longitudinal edge of the handle mount 1031. Moreover, the distal end of each handle mount flange 1033 may be sized to closely mate with a respective channel recess 123 when inserted into the retractor blade channel 121.

Moreover, the handle mount 1031 may include handle mount bearings 1035 that engage longitudinal sides of the handle shaft 1021 as the handle shaft 1021 passes through the handle mount bearings 1035. In this manner, the handle mount bearings 1035 may constrain movement of the handle shaft 1021 to rotational movement about a longitudinal axis of the handle shaft 1021. A distal end of the handle shaft 1021 may include a cam 1023 configured to engage a catch of the retractor blade 120, 1120 when the handle mount 1031 is slid into or otherwise received by the retractor blade channel 121. After fully seating the handle should 313 against the proximal end of the retractor blade 120, 1120, a person may rotate handle grip 1011 to rotate the handle shaft 1021 and the cam 1023 at the distal end of the handle shaft 1021. Such rotation of the cam 1023 may cause the cam 1023 to engage the catch of the retractor blade 120, 1120 and secure the retractor blade handle 1001 to the retractor blade 120, 1120. Such engagement of the cam 1023 with the catch may prevent the handle mount 1031 and the handle shaft 1021 from being extracted from the retractor blade channel 121. As such, once secured to the retractor blade 120, 1120, a person may manipulate and position the retractor blade 120, 1120 via the handle grip 1011 of the retractor blade handle 1001.

Conversely, a person may rotate the handle grip 1011 to rotate the cam 1023 away from the catch and disengage the cam 1023 from the catch. Once disengaged, a person may slide the handle shaft 1021 and the handle mount 1031 out of the retractor blade channel 121 and thus detach the retractor blade handle 1001 from the retractor blade 120, 1120.

While the present invention has been described with reference to certain embodiments, it will be understood by those skilled in the art that various changes may be made and equivalents may be substituted without departing from the scope of the present invention. In addition, many modifications may be made to adapt a particular situation or material to the teachings of the present invention without departing from its scope. Therefore, it is intended that the present invention not be limited to the particular embodiment or embodiments disclosed, but that the present invention encompasses all embodiments falling within the scope of the appended claims.

What is claimed is:

1. A retractor system, comprising:

a first retractor arm comprising a first retractor arm proximal end, a first retractor arm distal end, and a first retractor arm channel that extends through the first retractor arm distal end; and a first retractor blade comprising a first retractor blade proximal end, a first retractor blade distal end, a first retractor blade track that runs longitudinally between the first retractor blade proximal end and the first retractor blade distal end;

wherein the first retractor arm comprises a first retractor arm pawl that selectively extends into the first retractor arm channel;

wherein the first retractor blade track comprises track catches distributed between a first retractor blade track proximal end and a first retractor blade track distal end; and wherein the first retractor arm channel is configured to engage the first retractor blade track and permit longitudinal translation of the first retractor blade with respect to the first retractor arm distal end such that the first retractor arm distal end traverses along the first retractor blade track to align the first retractor arm pawl with a selected one of the track catches and secure the first retractor blade among multiple selectable positions with respect to the first retractor arm distal end.

2. The retractor system of claim 1, comprising:

a first rack comprising a first rail and first rack teeth, wherein the first rail comprises a first rail first end and a first rail second end, and wherein the first rack teeth are distributed along the first rail between the first rail first end and the first rail second end; and a first carriage comprising a first carriage opening and a first pinion, wherein the first rail passes through the first carriage opening, and wherein the first pinion including first pinion teeth that engage the first rack teeth and move the first carriage along the first rail based on rotation of the first pinion; and wherein the first retractor arm proximal end is coupled to the first carriage and is selectively positioned along the first rail via the first carriage.

3. The retractor system of claim 2, wherein:

the first carriage comprises a first carriage lever and a first carriage pawl;

the first carriage lever selectively engages the first carriage pawl with the first rack teeth; and the first carriage pawl, when engaged with the first rack teeth, permits movement of the first carriage along the first rail in a first direction but prevents movement of the first carriage along the first rail in a second direction.

4. The retractor system of claim 2, comprising:

a second rack comprising a second rail and second rack teeth, wherein the second rail comprises a second rail first end and a second rail second end, and wherein the second rack teeth are distributed along the second rail between the second rail first end and the second rail second end;

a second carriage comprising a second carriage opening and a second pinion, wherein the second rail passes through the second carriage opening, and wherein the second pinion includes second pinion teeth that engage the second rack teeth and move the second carriage along the second rail based on rotation of the second pinion; and a second retractor arm comprising a second retractor arm proximal end, a second retractor arm distal end, and a second retractor arm channel that extends through the second retractor arm distal end, wherein the second retractor arm proximal end is coupled to the second carriage and is selectively positioned along the second rail via the second carriage.

5. The retractor system of claim 4, comprising:

a second retractor blade comprising a second retractor blade proximal end, a second retractor blade distal end, a second retractor blade track that runs longitudinally between the second retractor blade proximal end and the second retractor blade distal end; and wherein the second retractor arm channel is configured to engage the second retractor blade track and selectively position the second retractor arm distal end along the second retractor blade track.

6. The retractor system of claim 4, comprising:

a central rack comprising a central rail and central rack teeth, wherein the central rail comprises a central rail proximal end and a central rail distal end, and wherein the central rack teeth are distributed along the central rail between the central rail proximal end and the central rail distal end;

a central retractor arm comprising a central retractor arm proximal end coupled to the central rail distal end, a central retractor arm distal end, and a central retractor arm channel that extends through the central retractor arm distal end; and a central carriage comprises a central carriage opening and a central carriage pinion, wherein the central rail passes through the central carriage opening, and wherein the central carriage pinion includes central carriage pinion teeth that engage the central rack teeth and move the central carriage along the central rail based on rotation of the central carriage pinion; and wherein the first rail first end is coupled to a first lateral side of the central carriage and second rail second end is coupled to a second lateral side of the central carriage.

7. The retractor system of claim 6, comprising:

a second retractor blade comprising a second retractor blade proximal end, a second retractor blade distal end, a second retractor blade track that runs longitudinally between the second retractor blade proximal end and the second retractor blade distal end, wherein the second retractor arm channel is configured to engage the second retractor blade track and selectively position the second retractor arm distal end along the second retractor blade track; and a central retractor blade comprising a central retractor blade proximal end, a central retractor blade distal end, a central retractor blade track that runs longitudinally between the central retractor blade proximal end and the central retractor blade distal end, wherein the central retractor arm channel is configured to engage the central retractor blade track and selectively position the central retractor arm distal end along the central retractor blade track.

8. The retractor system of claim 2, comprising:

a second carriage comprising a second carriage opening and a second pinion, wherein the first rail passes through the second carriage opening, and wherein the second pinion includes second pinion teeth that engage the first rack teeth and move the second carriage along the first rail based on rotation of the second pinion; and a second retractor arm comprising a second retractor arm proximal end, a second retractor arm distal end, and a second retractor arm channel that extends through the second retractor arm distal end, wherein the second retractor arm proximal end is coupled to the second carriage and is selectively positioned along the first rail via the second carriage.

9. The retractor system of claim 8, comprising:

a central rack comprising a central rail and central rack teeth, wherein the central rail comprises a central rail proximal end and a central rail distal end, and wherein the central rack teeth are distributed along the central rail between the central rail proximal end and the central rail distal end; and a central carriage coupled to the first rail between the first rail first end and the first rail second end, wherein the central carriage comprises a central carriage opening and a central carriage pinion, wherein the central rail passes through the central carriage opening, and wherein the central carriage pinion includes central carriage pinion teeth that engage the central rack teeth and move the central carriage along the central rail based on rotation of the central carriage pinion.

10. The retractor system of claim 9, comprising:

a central retractor arm comprising a central retractor arm proximal end, a central retractor arm distal end, and a central retractor arm channel that extends through the central retractor arm distal end; and wherein the central retractor arm proximal end is coupled to the central rail distal end.

11. The retractor system of claim 2, wherein the first retractor arm proximal end is coupled to the first carriage via a joint that permits rotation of the first retractor arm about an axis that extends longitudinally along the first retractor arm.

12. The retractor system of claim 1, wherein:

the first retractor arm channel comprises fingers that engage rails of the first retractor blade track;

the rails of the first retractor blade track are formed by a pair of longitudinal track recesses in a back side of the first retractor blade;

each longitudinal track recess runs from the first retractor blade proximal end toward the first retractor blade distal end; and openings in the back side of the first retractor blade permit engaging the fingers of the first retractor arm with the rails of the first retractor blade track via a lower end of each longitudinal track recess.

13. The retractor system of claim 1, comprising a spring that biases the first retractor arm pawl into the first retractor arm channel and into engagement with the track catches of the first retractor blade track.

14. The retractor system of claim 1, comprising:

a second retractor arm comprising a second retractor arm proximal end and a second retractor arm distal end; and a second retractor blade coupled to the second retractor arm distal end;

wherein the first retractor arm distal end comprises a first retractor arm attachment post; and wherein the second retractor arm distal end comprises a second retractor arm attachment post.

15. The retractor system of claim 14, comprising an accessory coupled to the first retractor arm and the second retractor arm via the first retractor arm attachment post and the second retractor arm attachment post.

16. The retractor system of claim 14, comprising a third retractor blade coupled to the first retractor arm and the second retractor arm via the first retractor arm attachment post and the second retractor arm attachment post.

17. The retractor system of claim 1, wherein:

the first retractor blade comprises a first retractor blade front side, a first retractor blade back side, and a first retractor blade channel;

the first retractor blade track runs along the first retractor blade back side; and the first retractor blade channel runs along the first retractor blade front side between the first retractor blade proximal end and the first retractor blade distal end.

18. The retractor system of claim 17, comprising an intradiscal shim inserted in the first retractor blade channel such that an intradiscal shim distal end protrudes beyond the first retractor blade distal end.

19. The retractor system of claim 17, comprising a retractor blade handle secured to the first retractor blade via insertion into the first retractor blade channel.

20. The retractor system of claim 1, wherein the first retractor blade comprises:

a fin channel along a first retractor blade longitudinal side; and a blade fin affixed to the first retractor blade via the fin channel such that the blade fin extends a lateral width of the first retractor blade.

* * * * *